(12) United States Patent
Toscano et al.

(10) Patent No.: US 10,683,491 B2
(45) Date of Patent: *Jun. 16, 2020

(54) SUBTILASE VARIANTS AND POLYNUCLEOTIDES ENCODING SAME

(71) Applicant: NOVOZYMES A/S, Bagsvaerd (DK)

(72) Inventors: Miguel Duarte Guilherme Pereira Toscano, Greve (DK); Leonardo De Maria, Bagsvaerd (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/532,568

(22) PCT Filed: Dec. 3, 2015

(86) PCT No.: PCT/EP2015/078586
§ 371 (c)(1),
(2) Date: Jun. 2, 2017

(87) PCT Pub. No.: WO2016/087617
PCT Pub. Date: Jun. 9, 2016

(65) Prior Publication Data
US 2017/0335307 A1    Nov. 23, 2017

(30) Foreign Application Priority Data

Dec. 4, 2014 (EP) .................................. 14196298
Mar. 27, 2015 (EP) .................................. 15161514
(Continued)

(51) Int. Cl.
*C12N 9/56* (2006.01)
*C12N 15/00* (2006.01)
(Continued)

(52) U.S. Cl.
CPC ................ *C12N 9/54* (2013.01); *C11D 3/386* (2013.01); *C11D 3/38681* (2013.01); *C12N 15/00* (2013.01); *C12Y 304/21062* (2013.01)

(58) Field of Classification Search
None
See application file for complete search history.

(56) References Cited

U.S. PATENT DOCUMENTS 5,677,272 A    10/1997  Ghosh
2009/0238923 A1  9/2009  Shaw
(Continued)

FOREIGN PATENT DOCUMENTS

WO    91/000345 A1    1/1991
WO    94/23053 A1    10/1994
(Continued)

OTHER PUBLICATIONS

Studer (Residue mutations and their impact on protein structure and function: detecting beneficial and pathogenic changes. Residue mutations and their impact on protein structure and function: detecting beneficial and pathogenic changes. Biochem. J. (2013) 449, 581-594.*

(Continued)

*Primary Examiner* — Yong D Pak
(74) *Attorney, Agent, or Firm* — David Fazzolare

(57) ABSTRACT

The present invention relates to subtilase variants suitable for use in, e.g., cleaning or detergent compositions, such as laundry detergent compositions and dish wash compositions, including automatic dish wash compositions. The present invention also relates to isolated DNA sequences
(Continued)

```
BLSAVI_SEQ01    1   AQSVPWGISRVQAPAAHNRGLTGSGVKVAVLDTGI-STHPDLNIRGGASF  49
                    ||||:|:|:::|||.|::|.|||.|||||:|:||  |:||||.:.||||.
BASBPN_SEQ02    1   AQSVPYGVSQIKAPALHSQGYTGSNVKVAVIDSGIDSSHPDLKVAGGASM  50

BLSAVI_SEQ01   50   VPGEPST-QDGNGHGTHVAGTIAALNNSIGVLGVAPSAELYAVKVLGASG  98
                    ||.|.:. ||.|.|||||||:||||||||||||||||.||||||||.|
BASBPN_SEQ02   51   VPSETNPFQDNNSHGTHVAGTVAALNNSIGVLGVAPSASLYAVKVLGADG 100

BLSAVI_SEQ01   99   SGSVSSIAQGLEWAGNNGMHVANLSLGSPSPSATLEQAVNSATSRGVLVV 148
                    ||..|.|..|:|||..|.|.|.|:|||.||.|||.|:.||:.|.:.||:||
BASBPN_SEQ02  101   SGQYSWIINGIEWAIANNMDVINMSLGGPSGSAALKAAVDKAVASGVVVV 150

BLSAVI_SEQ01  149   AASGNSG----AGSISYPARYANAMAVGATDQNNNRASFSQYGAGLDIVA 194
                    ||:||.|    :.::.||.:|.:.:|||.|:|.||||||.|.:||::|
BASBPN_SEQ02  151   AAAGNEGTSGSSSTVGYPGKYPSVIAVGAVDSSNQRASFSSVGPELDVMA 200

BLSAVI_SEQ01  195   PGVNVQSTYPGSTYASLNGTSMATPHVAGAAALVKQKNPSWSNVQIRNHL 244
                    ||:::|||.||.|.:.|||||||:|||||||:..|:|:|:|:|::|.|
BASBPN_SEQ02  201   PGVSIQSTLPGNKYGAYNGTSMASPHVAGAAALILSKHPNWTNTQVRSSL 250

BLSAVI_SEQ01  245   KNTATSLGSTNLYGSGLVNAEAATR         269
                    :||.|.||.:..||.||:|.:||.:
BASBPN_SEQ02  251   ENTTTKLGDSFYYGKGLINVQAAAQ         275
``` encoding the variants, expression vectors, host cells, and methods for producing and using the variants of the invention.

26 Claims, 1 Drawing Sheet

Specification includes a Sequence Listing.

(30) Foreign Application Priority Data

Nov. 12, 2015 (EP) .................................. 15194217
Nov. 25, 2015 (EP) .................................. 15196306

(51) Int. Cl.
*C12N 1/20* (2006.01)
*C12P 21/06* (2006.01)
*C12P 21/04* (2006.01)
*C11D 3/386* (2006.01)
*C07H 21/04* (2006.01)
*C12N 9/54* (2006.01)

(56) References Cited

U.S. PATENT DOCUMENTS

| | | |
|---|---|---|
| 2010/0192985 A1 | 8/2010 | Aehle |
| 2011/0251073 A1* | 10/2011 | Cascao-Pereira .......................... C11D 3/38681 506/2 |

FOREIGN PATENT DOCUMENTS

| | | |
|---|---|---|
| WO | 95/10615 A1 | 4/1995 |
| WO | 2003/054127 A2 | 7/2003 |
| WO | 2009/149200 A2 | 12/2009 |
| WO | 2016/001449 A1 | 1/2016 |
| WO | 2016/001450 A2 | 1/2016 |
| WO | 2016/097405 A1 | 6/2016 |

OTHER PUBLICATIONS

Kudo et al, 2014, Genome Announcements 2(3), e00622-14.
Noguchi et al, 2014, UniProt accession No. A0A061N1G1.
Singer et al, 1998, Genes and genomes 1, 63-64—English Translation.

* cited by examiner

```
BLSAVI_SEQ01      1 AQSVPWGISRVQAPAAHNRGLTGSGVKVAVLDTGI-STHPDLNIRGGASF  49
                    ||||:|:|:::|||.::|.|||.|||||:|:||  |:|||||..:.||||.
BASBPN_SEQ02      1 AQSVPYGVSQIKAPALHSQGYTGSNVKVAVIDSGIDSSHPDLKVAGGASM  50

BLSAVI_SEQ01     50 VPGEPST-QDGNGHGTHVAGTIAALNNSIGVLGVAPSAELYAVKVLGASG  98
                    ||.|.:. ||.|.||||||||:|||||||||||||||.||||||||.|
BASBPN_SEQ02     51 VPSETNPFQDNNSHGTHVAGTVAALNNSIGVLGVAPSASLYAVKVLGADG 100

BLSAVI_SEQ01     99 SGSVSSIAQGLEWAGNNGMHVANLSLGSPSPSATLEQAVNSATSRGVLVV 148
                    ||..|.|..|:|||..|.|.|.|:|||.||.||.|::..||:.|..||:||
BASBPN_SEQ02    101 SGQYSWIINGIEWAIANNMDVINMSLGGPSGSAALKAAVDKAVASGVVVV 150

BLSAVI_SEQ01    149 AASGNSG----AGSISYPARYANAMAVGATDQNNNRASFSQYGAGLDIVA 194
                    ||:||.|     :.::.||.:|.:.:|||||.|.:|.|||||..|..||::|
BASBPN_SEQ02    151 AAAGNEGTSGSSSTVGYPGKYPSVIAVGAVDSSNQRASFSSVGPELDVMA 200

BLSAVI_SEQ01    195 PGVNVQSTYPGSTYASLNGTSMATPHVAGAAALVKQKNPSWSNVQIRNHL 244
                    |||::|||.||:.|.:.||||||:||||||||||:...|:|:|:|.|:..|
BASBPN_SEQ02    201 PGVSIQSTLPGNKYGAYNGTSMASPHVAGAAALILSKHPNWTNTQVRSSL 250

BLSAVI_SEQ01    245 KNTATSLGSTNLYGSGLVNAEAATR    269
                    :||.|.||.:...||.||:|.:||.:
BASBPN_SEQ02    251 ENTTTKLGDSFYYGKGLINVQAAAQ   275
```

SUBTILASE VARIANTS AND POLYNUCLEOTIDES ENCODING SAME

CROSS-REFERENCE TO RELATED APPLICATIONS

This application is a 35 U.S.C. 371 national application of PCT/EP2015/078586 filed Dec. 3, 2015, which claims priority or the benefit under 35 U.S.C. 119 of European application nos. 14196298.5, 15161514.3, 15194217.4 and 15196306.3, filed Dec. 4, 2014, Mar. 27, 2015, Nov. 12, 2015 and Nov. 25, 2015, respectively, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to subtilase variants suitable for use in, e.g., cleaning or detergent compositions, such as laundry detergent compositions and dish wash compositions, including automatic dish wash compositions. The present invention also relates to isolated DNA sequences encoding the variants, expression vectors, host cells, and methods for producing and using the variants of the invention.

Description of the Related Art

In the detergent industry, enzymes have for many decades been implemented in washing formulations. Enzymes used in such formulations comprise amylases, cellulases, lipases, mannosidases, and proteases, as well as other enzymes or mixtures thereof. Commercially the most important enzymes are proteases.

An increasing number of commercially used proteases are protein engineered variants of naturally occurring wild type proteases Everlase®, Relase®, Ovozyme®, Polarzyme®, Liquanase®, Liquanase Ultra® and Kannase® (Novozymes A/S), Purafast®, Purafect OXP®, FN3® and FN4® (Genencor International, Inc.). Further, a number of protease variants are described in the art, such as WO 91/00345 (Novozymes A/S) and WO 94/23053 (Novozymes A/S) describes, e.g., mutations in position 262. The variants are suitable for use in, e.g., cleaning or detergent compositions.

A number of useful subtilase variants have been described many of which have provided improved activity, stability, and solubility in different detergents However, various factors make further improvement of the proteases advantageous. The washing conditions such as temperature and pH changes over time and many stains are still difficult to completely remove under conventional washing conditions. Further, in wash conditions can result in inactivation of the enzymes (due to, e.g., pH, temperature or chelation instability) resulting in loss of wash performance during the wash cycle. Thus despite the intensive research in protease development there remains a need for new and improved proteases that have improved stability, in particular improved in wash stability and/or storage stability, and preferably similar or improved wash performance compared to the parent subtilase.

SUMMARY OF THE INVENTION

The present invention relates to subtilase variants having protease activity and comprising the substitutions X9E+X206L+X262E, e.g., S9E+Q206L+L262E, wherein the positions correspond to the positions of the polypeptide of SEQ ID NO: 2.

The present invention further relates to polynucleotides encoding the subtilase variants; compositions, preferably detergent compositions, comprising a subtilase variant; use of the compositions in a cleaning process and methods for obtaining a subtilase variant and for removing a stain from a surface.

BRIEF DESCRIPTION OF THE FIGURES

FIG. 1 is an alignment of the amino acid sequences of subtilisin 309 (SEQ ID NO: 1) and subtilisin BPN' (SEQ ID NO: 2), using the Needleman-Wunsch algorithm (Needleman and Wunsch, 1970, *J. Mol. Biol.* 48: 443-453).

DEFINITIONS

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

The term "detergent component" is defined herein to mean the types of chemicals which can be used in detergent compositions. Examples of detergent components are surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers. The detergent composition may comprise of one or more of any type of detergent component.

The term "detergent composition" includes, unless otherwise indicated, all forms of detergent compositions such as gel, granulate, liquid, paste, powder, spray or tablet compositions including heavy-duty liquids (HDL), fine-fabric liquid detergents, liquid and/or solid laundry detergents and fine fabric detergents; hard surface cleaning formulations for, e.g., glass, wood, ceramic and metal counter tops and windows; carpet cleaners; oven cleaners; fabric fresheners; fabric softeners; textile and laundry pre-spotters, as well as dish wash detergents such as hand dishwashing agents, light duty dishwashing agents, machine dishwashing agents; all-purpose or heavy-duty washing agents, liquid, gel or paste-form all-purpose washing agents, liquid cleaning and disinfecting agents, including antibacterial hand-wash types, cleaning bars, mouthwashes, denture cleaners, car or carpet shampoos, bathroom cleaners; hair shampoos and hair-rinses; shower gels, foam baths; metal cleaners; as well as cleaning auxiliaries such as bleach additives and "stain-stick" or pre-treat types.

In addition to containing a subtilase variant of the invention, the detergent formulation may contain one or more additional enzymes (such as amylases, catalases, cellulases (e.g., endoglucanases), cutinases, haloperoxygenases, lipases, mannanases, pectinases, pectin lyases, peroxidases, proteases, xanthanases, and xyloglucanases, or any mixture thereof), and/or components such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxidoreductases, bluing agents and fluorescent dyes, antioxidants, and solubilizers.

The term "dish wash" refers to all forms of washing dishes, e.g., by hand or automatic dish wash. Washing dishes includes, but is not limited to, the cleaning of all forms of crockery such as plates, cups, glasses, bowls, all forms of cutlery such as spoons, knives, forks and serving utensils as well as ceramics, plastics such as melamine, metals, china, glass and acrylics.

The term "dish washing composition" refers to all forms of compositions for cleaning hard surfaces. The present invention is not restricted to any particular type of dish wash composition or any particular detergent.

The term "expression" includes any step involved in the production of a variant including, but not limited to, transcription, post-transcriptional modification, translation, post-translational modification, and secretion.

The term "expression vector" means a linear or circular DNA molecule that comprises a polynucleotide encoding a variant and is operably linked to control sequences that provide for its expression.

The term "hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, and cutlery such as spoons, knives, forks, serving utensils, ceramics, plastics such as melamine, metals, china, glass and acrylics.

The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

The term "improved property" means a characteristic associated with a subtilase variant that is improved compared to the parent subtilase. Such improved properties include, but are not limited to, wash performance, protease activity, thermal activity profile, thermostability, pH activity profile, pH stability, substrate/cofactor specificity, improved surface properties, substrate specificity, product specificity, increased stability, improved stability under storage conditions, and chemical stability.

The term "stability" includes storage stability and stability during use, e.g., during a wash process and reflects the stability of the subtilase variant according to the invention as a function of time, e.g., how much activity is retained when the subtilase variant is kept in solution in particular in a detergent solution. The stability is influenced by many factors, e.g., pH, temperature, detergent composition, e.g., amount of builder, surfactants etc. The term "improved stability" or "increased stability" is defined herein as a variant subtilase displaying an increased stability in solution, relative to the stability of the parent subtilase. The terms "improved stability" and "increased stability" includes "improved chemical stability", "detergent stability" or "improved detergent stability."

The term "improved chemical stability" is defined herein as a variant subtilase displaying retention of enzymatic activity after a period of incubation in the presence of a chemical or chemicals, either naturally occurring or synthetic, which reduces the enzymatic activity of the parent enzyme. Improved chemical stability may also result in variants being more able to catalyze a reaction in the presence of such chemicals. In a particular aspect of the invention the improved chemical stability is an improved stability in a detergent, in particular in a liquid detergent. The term "detergent stability" or "improved detergent stability" is in particular an improved stability of the protease activity when a subtilase variant of the present invention is mixed into a liquid detergent formulation, and then stored at a temperature between 15 and 50° C., e.g., 20° C., 30° C. or 40° C.

The term "improved thermal activity" means a variant displaying an altered temperature-dependent activity profile at a specific temperature relative to the temperature-dependent activity profile of the parent. The thermal activity value provides a measure of the variant's efficiency in enhancing catalysis of a hydrolysis reaction over a range of temperatures. A more thermo active variant will lead to an increase in enhancing the rate of hydrolysis of a substrate by an enzyme composition thereby decreasing the time required and/or decreasing the enzyme concentration required for activity. Alternatively, a variant with a reduced thermal activity will enhance an enzymatic reaction at a temperature lower than the temperature optimum of the parent defined by the temperature-dependent activity profile of the parent.

The term "improved wash performance" is defined herein as a subtilase variant according to the invention displaying an improved wash performance relative to the wash performance of the parent protease, e.g., by increased stain removal. The term "wash performance" includes wash performance in laundry but also, e.g., in dish wash. The wash performance may be quantified as described under the definition of "wash performance" herein.

The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

The term "laundering" relates to both household laundering and industrial laundering and means a process of treating textiles and/or fabrics with a solution containing a detergent composition of the present invention. The laundering process can for example be carried out using, e.g., a household or an industrial washing machine or can be carried out by hand.

The term "mature polypeptide" means a polypeptide in its final form following translation and any post-translational modifications, such as N-terminal processing, C-terminal truncation, glycosylation, phosphorylation, autocatalytic activation etc. In one aspect, the mature polypeptide is amino acids 1 to 269 of SEQ ID NO: 1 and 1 to 275 of SEQ ID NO: 2. It is known in the art that a host cell may produce a mixture of two of more different mature polypeptides (i.e., with a different C-terminal and/or N-terminal amino acid) expressed by the same polynucleotide.

The term "mature polypeptide coding sequence" means a polynucleotide that encodes a mature polypeptide having protease activity.

The term "mutant" means a polynucleotide encoding a variant.

The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

The term "operably linked" means a configuration in which a control sequence is placed at an appropriate position relative to the coding sequence of a polynucleotide such that the control sequence directs expression of the coding sequence.

The term "parent" means a protease to which an alteration is made to produce the enzyme variants of the present invention. It will be understood that in the present context the expression "having identical amino acid sequence" relates to 100% sequence identity. In a particular embodiment the parent is a protease with at least 60% identity, such as at least 65%, at least 70%, at least 75%, at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% identity to a polypeptide of SEQ ID NO: 1, 2, 3, 4, 5, 6, 7, 8, 9, 10, or 11.

The term "protease" is defined herein as an enzyme that hydrolyzes peptide bonds. It includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1-5 published in *Eur. J. Biochem.* 1223: 1-5 (1994); *Eur. J. Biochem.* 232: 1-6 (1995); *Eur. J. Biochem.* 237: 1-5 (1996); *Eur. J. Biochem.* 250: 1-6 (1997); and *Eur. J. Biochem.* 264: 610-650 (1999); respectively. The most widely used proteases in the detergent industry such as laundry and dish wash are the serine proteases or serine peptidases which is a subgroup of proteases characterised by having a serine in the active site, which forms a covalent adduct with the substrate. Further the subtilases (and the serine proteases) are characterized by having two active site amino acid residues apart from the serine, namely a histidine residue and an aspartic acid residue. Subtilase refer to a sub-group of serine protease according to Siezen et al., 1991, *Protein Engng.* 4: 719-737 and Siezen et al., 1997, *Protein Science* 6: 501-523. The subtilases may be divided into 6 sub-divisions, i.e., the Subtilisin family, the Thermitase family, the Proteinase K family, the Lantibiotic peptidase family, the Kexin family and the Pyrolysin family. The term "protease activity" means a proteolytic activity (EC 3.4). Proteases usably in detergents are mainly endopeptidases (EC 3.4.21). There are several protease activity types: The three main activity types are: trypsin-like where there is cleavage of amide substrates following Arg or Lys at P1, chymotrypsin-like where cleavage occurs following one of the hydrophobic amino acids at P1, and elastase-like with cleavage following an Ala at P1. For purposes of the present invention, protease activity is determined according to the Suc-AAPF-pNA activity assay, as described in the Materials and Methods section below. In one aspect, the subtilase variants of the present invention have at least 20%, e.g., at least 40%, at least 50%, at least 60%, at least 70%, at least 80%, at least 90%, at least 95%, or at least 100% of the enzyme activity of the mature polypeptide of the parent enzyme. In one particular aspect the subtilase variants of the present invention have at least 20%, e.g., at least 40%, at least 50%, at least 60%, at least 70%, at least 80%, at least 90%, at least 95%, or at least 100% of the enzyme activity of a polypeptide of SEQ ID NO: 1, 2, 3, 4, 5, 6, 7, 8, 9, 10, or 11.

The term "protease activity" means a proteolytic activity (EC 3.4). Proteases of the invention are endopeptidases (EC 3.4.21). There are several protease activity types: The three main activity types are: trypsin-like where there is cleavage of amide substrates following Arg or Lys at P1, chymotrypsin-like where cleavage occurs following one of the hydrophobic amino acids at P1, and elastase-like with cleavage following an Ala at P1. For purposes of the present invention, protease activity is determined according to the procedure described in "Materials and Methods" below. The subtilase variants of the present invention preferably have at least 20%, e.g., at least 40%, at least 50%, at least 60%, at least 70%, at least 80%, at least 90%, at least 95%, and at least 100% of the protease activity of a polypeptide of SEQ ID NO: 1, 2, 3, 4, 5, 6, 7, 8, 9, 10, or 11.

The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

The different stringency conditions are defined as follows.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 1×SSC, 0.2% SDS at 60° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 1×SSC, 0.2% SDS at 65° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.5×SSC, 0.2% SDS at 65° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.3×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.15×SSC, 0.2% SDS at 65° C.

The term "substantially pure variant" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the variant is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The variants of the present invention are preferably in a substantially pure form. This can be accomplished, for example, by preparing the variant by well-known recombinant methods or by classical purification methods.

The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5'- and 3'-untranslated regions, such as promoters and terminators. It is preferred that the substantially pure polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

The term "textile" means any textile material including yarns, yarn intermediates, fibers, non-woven materials, natural materials, synthetic materials, as well as fabrics made of these materials such as garments, cloths and other articles). When the term fabric or garment is used it is intended to include the broader term textiles as well.

The term "variant" means a polypeptide having protease activity comprising an alteration, i.e., a substitution, insertion, and/or deletion, at three or more (e.g., several) positions. A substitution means replacement of the amino acid occupying a position with a different amino acid; a deletion means removal of the amino acid occupying a position; and an insertion means adding one or more (e.g., several) amino acids, e.g., 1, 2, 3, 4 or 5 amino acids adjacent to and immediately following the amino acid occupying a position. The term subtilase variant means a variant of a subtilase parent, i.e., a subtilase variant is a subtilase which comprises alterations i.e., a substitution, insertion, and/or deletion, at three or more (e.g., several) positions compared to the parent subtilase.

The term "wash performance" is used as an enzyme's ability to remove stains present on the object to be cleaned during, e.g., wash, such as laundry or hard surface cleaning. The improvement in the wash performance may be quantified by calculating the so-called intensity value (Int) defined in the AMSA assay, as described in Example 3.

The term "wild-type subtilase" means a protease expressed by a naturally occurring organism, such as a bacterium, archaea, yeast, fungus, plant or animal found in nature. An example of a wild-type subtilase is subtilisin BPN', i.e., amino acids 1 to 275 of SEQ ID NO: 2.

Conventions for Designation of Variants

For purposes of the present invention, subtilisin BPN' (the sequence of amino acids 1-275 of SEQ ID NO: 2 (Siezen et al., 1991, *Protein Eng.* 4: 719-737)) is used to determine the corresponding amino acid residue in another protease. The amino acid sequence of another protease is aligned with the mature polypeptide disclosed in SEQ ID NO: 2, and based on the alignment, the amino acid position number corresponding to any amino acid residue in the polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another protease can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26:1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions: For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively. An "X" preceding a position means that any original amino acid at the position may be substituted. For example, X9E means that any amino acid residue at position 9 other than E is substituted with E; X206L means that any amino acid residue at position 206 other than L is substituted with L; and X262E means that any amino acid residue at position 262 other than E is substituted with E.

Deletions: For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions: The insertion of an additional amino acid residue such as, e.g., a lysine after G195 may be indicated by: Gly195GlyLys or G195GK. Alternatively insertion of an additional amino acid residue such as lysine after G195 may be indicated by: *195aK. When more than one amino acid residue is inserted, such as, e.g., a Lys and Ala after G195 this may be indicated as: Gly195GlyLysAla or G195GKA. In such cases, the inserted amino acid residue(s) may also be numbered by the addition of lower case letters to the position number of the amino acid residue preceding the inserted amino acid residue(s), in this example: *195aK *195bA. In the above example, the sequences 194 to 196 would thus be:

```
                       194 195 196
    Subtilisin 309      A - G - L 194 195 195a 195b 196
    Variant             A - G - K -  A-   L
```

In cases where a substitution and an insertion occur at the same position, this may be indicated as S99SD+S99A or in short S99AD. The same modification may also be indicated as S99A+*99aD.

In cases where an amino acid residue identical to the existing amino acid residue is inserted, it is clear that degeneracy in the nomenclature arises. If for example a glycine is inserted after the glycine in the above example this would be indicated by G195GG or *195aG. The same actual change could just as well be indicated as A194AG or *194aG for the change from:

```
              194 195 196
Subtilisin 309  A - G - L
``` to:

```
              194 195 195a 196
Variant        A - G - G  - L
              194 194a 195 196
```

Such instances will be apparent to the skilled person and the indication G195GG and corresponding indications for this type of insertions are thus meant to comprise such equivalent degenerate indications.

Multiple alterations: Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively. Alternatively multiple alterations may be separated be space or a comma, e.g., A170Y G195E or A170Y, G195E respectively.

Different alterations: Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

Alternatively different alterations or optional substitutions may be indicated in brackets, e.g., Arg170[Tyr, Gly] or Arg170{Tyr, Gly} or in short R170 [Y,G] or R170 {Y, G}.

DETAILED DESCRIPTION OF THE INVENTION

The present invention relates to subtilase variants having protease activity and comprising the substitutions X9E+X206L+X262E, e.g., S9E+Q206L+L262E, wherein the positions correspond to the positions of the polypeptide of SEQ ID NO: 2.

In one embodiment, the subtilase variant has improved stability, in particular improved storage stability, compared to the parent subtilase. In a preferred embodiment, the subtilase variant has improved stability, in particular improved storage stability, and on par or improved wash performance compared to the parent subtilase.

In another embodiment, the subtilase variant is
a) a polypeptide that has at least 60% but less than 100% sequence identity to the amino acid sequence of the parent subtilase;
b) a polypeptide that is encoded by a polynucleotide that hybridizes under low stringency conditions, medium stringency conditions, medium-high stringency conditions, high stringency conditions, or very high stringency conditions with:
   (i) the mature polypeptide coding sequence of the parent subtilase or
   (ii) the full-length complement of (i); or
c) a polypeptide that is encoded by a polynucleotide having at least 60% but less than 100% sequence identity to the mature polypeptide coding sequence of the parent subtilase.

In an embodiment, the subtilase variant has at least 65% but less than 100% sequence identity to the parent subtilase. In an embodiment, the subtilase variant has at least 70% but less than 100% sequence identity to the parent subtilase. In an embodiment, the subtilase variant has at least 75% but less than 100% sequence identity to the parent subtilase. In an embodiment, the subtilase variant has at least 80% but less than 100% sequence identity to the parent subtilase. In an embodiment, the subtilase variant has at least 85% but less than 100% sequence identity to the parent subtilase. In an embodiment, the subtilase variant has at least 90% but less than 100% sequence identity to the parent subtilase. In an embodiment, the subtilase variant has at least 93% but less than 100% sequence identity to the parent subtilase. In an embodiment, the subtilase variant has at least 95% but less than 100% sequence identity to the parent subtilase. In an embodiment, the subtilase variant has at least 96% but less than 100% sequence identity to the parent subtilase. In an embodiment, the subtilase variant has at least 97% but less than 100% sequence identity to the parent subtilase. In an embodiment, the subtilase variant has at least 98% but less than 100% sequence identity to the parent subtilase.

In an embodiment, the variant has an amino acid sequence which is at least 60% identical to SEQ ID NO: 1, e.g., at least 60%, such as at least 70%, such as at least 80%, such as at least 90%, such as at least 95% sequence identity to the amino acid sequence of SEQ ID NO: 1.

In another embodiment, the variant has an amino acid sequence which is at least 60% identical to SEQ ID NO: 2, e.g., at least 60%, such as at least 70%, such as at least 80%, such as at least 90%, such as at least 95% sequence identity to the amino acid sequence of SEQ ID NO: 2.

In another embodiment, the variant has an amino acid sequence which is at least 60% identical to SEQ ID NO: 3, e.g., at least 60%, such as at least 70%, such as at least 80%, such as at least 90%, such as at least 95% sequence identity to the amino acid sequence of SEQ ID NO: 3.

In another embodiment, the variant has an amino acid sequence which is at least 60% identical to SEQ ID NO: 4, e.g., at least 60%, such as at least 70%, such as at least 80%, such as at least 90%, such as at least 95% sequence identity to the amino acid sequence of SEQ ID NO: 4.

In another embodiment, the variant has an amino acid sequence which is at least 60% identical to SEQ ID NO: 5, e.g., at least 60%, such as at least 70%, such as at least 80%, such as at least 90%, such as at least 95% sequence identity to the amino acid sequence of SEQ ID NO: 5.

In another embodiment, the variant has an amino acid sequence which is at least 60% identical to SEQ ID NO: 6, e.g., at least 60%, such as at least 70%, such as at least 80%, such as at least 90%, such as at least 95% sequence identity to the amino acid sequence of SEQ ID NO: 6.

In another embodiment, the variant has an amino acid sequence which is at least 60% identical to SEQ ID NO: 7, e.g., at least 60%, such as at least 70%, such as at least 80%, such as at least 90%, such as at least 95% sequence identity to the amino acid sequence of SEQ ID NO: 7.

In another embodiment, the variant has an amino acid sequence which is at least 60% identical to SEQ ID NO: 8, e.g., at least 60%, such as at least 70%, such as at least 80%, such as at least 90%, such as at least 95% sequence identity to the amino acid sequence of SEQ ID NO: 8.

In another embodiment, the variant has an amino acid sequence which is at least 60% identical to SEQ ID NO: 9, e.g., at least 60%, such as at least 70%, such as at least 80%, such as at least 90%, such as at least 95% sequence identity to the amino acid sequence of SEQ ID NO: 9.

In another embodiment, the variant has an amino acid sequence which is at least 60% identical to SEQ ID NO: 10, e.g., at least 60%, such as at least 70%, such as at least 80%, such as at least 90%, such as at least 95% sequence identity to the amino acid sequence of SEQ ID NO: 10.

In another embodiment, the variant has an amino acid sequence which is at least 60% identical to SEQ ID NO: 11, e.g., at least 60%, such as at least 70%, such as at least 80%, such as at least 90%, such as at least 95% sequence identity to the amino acid sequence of SEQ ID NO: 11.

In one aspect, the total number of alterations in the parent subtilase is between 3 and 30, preferably between 3 and 20, more preferably between 3 and 15, even more preferably between 3 and 10, most preferably between 3 and 8 alterations. In another aspect, total number of alterations in the parent subtilase is 3, 4, 5, 6, 7, 8, 9, 10, 11, 12, 13, 14, 15, 16, 17, 18, 19, 20, 21, 22, 23, 24, 25, 26, 27, 28, 29 or 30 alterations.

The subtilase variants of the present invention may further comprise one or more additional alterations. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, AlaNal, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. For BPN' (SEQ ID NO: 2) the catalytic triad comprising the amino acids S221, H64, and D32 is essential for protease activity of the enzyme.

In an embodiment, the subtilase variant comprises X9E+X206L+X262E and further comprises X76D (e.g., N76D).

In an embodiment or any of the embodiments above, the subtilase variant further comprises X9E+X206L+X262E and one or more alterations selected from the group consisting of X3T (e.g., S3T), X4I (e.g., V4I), X15T (e.g., A15T), X24G (e.g., S24G), X24R (e.g., S24R), X27R (e.g., K27R), *36D, X43A (e.g., N43A), X43C (e.g., N43C), X43L (e.g., N43L), X43R (e.g., N43R), X43W (e.g., N43W), X68A (e.g., V68A), X72A (e.g., I72A), X72V (e.g., I72V), X78D (e.g., S78D), X87R (e.g., N87R), X87S (e.g., N87S), *97E, X98S (e.g., A98S), X99A (e.g., S99A), X99D (e.g., S99D), X99A (e.g., S99A), X99D (e.g., S99D), X99E (e.g., S99E), X99G (e.g., S99G), *99D, X101D (e.g., S101D), X101E (e.g., S101E), X101G (e.g., S101G), X101I (e.g., S101I), X101K (e.g., S101K), X101L (e.g., S101L), X101M (e.g., S101M), X101N (e.g., S101N), X101R (e.g., S101R), X103A (e.g., S103A), X104F (e.g., V104F), X104I (e.g., V104I), X104N (e.g., V104N), X104Y (e.g., V104Y), X106A (e.g., S106A), X114V (e.g., A114V), X115T (e.g., G115T), X115W (e.g., G115W), X118R (e.g., G118R), X118V (e.g., G118V), X120D (e.g., H120D), X1201 (e.g., H120I), X120N (e.g., H120N), X120T (e.g., H120T), X120V (e.g., H120V), X123S (e.g., N123S), X128A (e.g., S128A), X128L (e.g., S128L), X128S (e.g., S128S), X129D (e.g., P129D), X129N (e.g., P129N), X129Q (e.g., P129Q), X130A (e.g., S130A), X147W (e.g., V147W), X149C (e.g., V149C), X149N (e.g., V149N), X158E (e.g., A158E), X160D (e.g., G160D, X160P (e.g., G160P), X161C (e.g., S161C), X161E (e.g., S161E), X162L (e.g., I162L), X163A (e.g., S163A), X163D (e.g., S163D), X167A (e.g., Y167A), X170S (e.g., R170S), X182C (e.g., Q182C), X182E (e.g., Q182E), X185C (e.g., N185C), X185E (e.g., N185E), X188C (e.g., S188C), X188D (e.g., S188D), X188E (e.g., S188E), X191N (e.g., Q191N), X194P (e.g., A194P), X195E (e.g., G195E), X199M (e.g., V199M), X204D (e.g., N204D), X204V (e.g., N204V), X205I (e.g., V205I), X209W (e.g., Y209W), X212A (e.g., S212A), X212D (e.g., S212D), X212G (e.g., S212G), X212N (e.g., S212N), X216I (e.g., S216I), X216T (e.g., S216T), X216V (e.g., S216V), X217C (e.g., L217C), X217D (e.g., L217D), X217E (e.g., L217E), X217M (e.g., L217M), X217Q (e.g., L217Q), X217Y (e.g., L217Y), X218D (e.g., N218D), X218E (e.g., N218E), X218T (e.g., N218T), X222C (e.g., M222C), X222R (e.g., M222R), X222S (e.g., M222S), X225A (e.g., P225A), X232V (e.g., A232V), X235L (e.g., K235L), X236H (e.g., Q236H), X245K (e.g., Q245K), X245R (e.g., Q245R), X252K (e.g., N252K), X255C (e.g., T255C), X255E (e.g., T255E), X256A (e.g., S256A), X256C (e.g., S256C), X256D (e.g., S256D), X256V (e.g., S256V), X256Y (e.g., S256Y), X259D (e.g., S259D), X260E (e.g., T260E), X260P (e.g., T260P), X261C (e.g., N261C), X261E (e.g., N261E), X261F (e.g., N261F), X261L (e.g., N261L), X261M (e.g., N261M), X261V (e.g., N261V), X261W (e.g., N261W), X261Y (e.g., N261Y), and X274A (e.g., T274A), wherein each position corresponds to the position of the polypeptide of SEQ ID NO: 2.

The invention relates to subtilase variants, preferably protease variants of a protease parent having at least 60%, such as at least 70%, such as at least 75%, such as at least 80%, such as at least 85%, such as at least 90%, such as at least 95% or 100% sequence identity to SEQ ID NO: 1, wherein the subtilase variants compared to SEQ ID NO: 1 comprises the substitutions X9E+X206L+X262E, e.g., S9E+Q206L+L262E, wherein the positions correspond to the positions of the polypeptide of SEQ ID NO: 2. As mentioned SEQ ID NO: 2 is used for numbering an alignment could be found in FIG. 1 and the skilled person can easily align other subtilase parent than SEQ ID NO: 1 and find the corresponding amino acids in SEQ ID NO: 2.

The inventors have found that the three fold substitution X9E+X206L+X262E provides increased stability to a subtilase. Thus one embodiment of the invention relates to subtilase variants which compared to the parent subtilase and/or compared to a subtilase with SEQ ID NO: 1 comprises the three mutations X9E+X206L+X262E (numbered according to SEQ ID NO: 2) and which have increase stability in a detergent compared to the parent subtilase e.g. compared to SEQ ID NO: 1. A particular preferred embodiment relates to subtilase variants comprising, compared to SEQ ID NO: 1, the substitutions X9E+X206L+X262E (numbered according to SEQ ID NO 2) and have at least 5%, such as at least 10%, such as at least 20%, at least 30%, at least 40%, at least 50%, at least 60%, at least 70%, at least 80%, at least 90%, at least 100%, at least 110%, at least 120%, at least 130%, at least 140%, at least 150%, at least 160%, at least 170% higher residual activity than the parent subtilase and/or a subtilase with SEQ ID NO: 1 when measured after 47 hours at 60° C. in liquid detergent with pH 8, as described in Example 4 and 5 of the application. Another preferred embodiment relates to subtilase variants comprising, compared to SEQ ID NO: 1, the substitutions X9E+X206L+X262E (numbered according to SEQ ID NO: 2) which have t½ half-life improvement factors relative to the parent or relative to SEQ ID NO: 1 (subtilisin 309) which is greater than 1 and preferably at least 2, such as at least 5, such as at least 10, such as at least 50, at least 100, at least 200, at least 300, at least 400, at least 500, at least 600, at least 800, at least 1000,at least 1500, at least 2000, at least 2500, at least 3000, at least 3500, at least 4000, at least 4500, at least 5000, at least 5500, at least 6000, at least 6500, at least 7000, at least 7500, at least 8000, at least 8500, at least 9000, at least 9500 or at least 10000 or more. Calculation of t½ half-life improvement factors is described in Example 4 of the application.

Another preferred embodiment relates to subtilase variants comprising, compared to SEQ ID NO: 1, the substitutions X9E+X206L+X262E (numbered according to SEQ ID NO: 2), wherein the subtilase variants have at least 10% more, such as at least 20%, at least 25%, at least 30%, at least 35%, at least 40%, at least 45%, at least 50%, at least 55% at least 60%, at least 65%, at least 70%, at least 75%, at least 80%, at least 85%, at least 90% or at least 95% residual activity compared to the parent or compared to SEQ ID NO 1. Calculation of residual activity or t½ is described in example 4 herein.

In another preferred embodiment, the invention relates to subtilase variants which compared to the parent subtilase and/or compared to a subtilase with SEQ ID NO: 1 comprises the three mutations X9E+X206L+X262E (numbered according to SEQ ID NO: 2) and which have increase stability in a detergent compared to the parent subtilase e.g. compared to SEQ ID NO: 1 and which has on par or improved wash performance compared to the parent subtilase e.g. compared to SEQ ID NO: 1. The variants of the invention may comprise additional stabilising and/or performance enhancing mutations such as N43R, G61E, N76D, S161E, G160D, G160P, S161E, N182E, N185E, S188E, A194P, N204D, V205I, Y209W, or S212G. In one embodiment and according to any of the above embodiment a variant of the invention comprises the following substitutions compared to SEQ ID NO 1; S9E+Q206L+L262E, S9E+N76D+Q206L+L262E, S9E+N76D+Q206L+Y209W+L262E, S9E+G61E+N76D+Q206L+L262E, S9E+N43R+N76D+Q206L+L262E, S9E+N43R+N76D+Q206L+Y209W+L262E, S9E+N76D+Q206L+Y209W+S212G+L262E, S9E+N76D+Q206L+V205I+Y209W+L262E, S9E+N76D+N204D+Q206L+Y209W+L262E, S9E+N76D+S188E+Q206L+Y209W+L262E, S9E+N76D+N185E+Q206L+Y209W+L262E, S9E+N76D+N182E+Q206L+Y209W+L262E, S9E+N76D+S161E+Q206L+Y209W+L262E, S9E+N76D+G160P+Q206L+Y209W+L262E, S9E+N76D+G160D+Q206L+Y209W+L262E;

S9E+N43R+N76D+A194P+Q206L+Y209W+S259D+L262E or S9E+N43R+N76D+A194P+V205I+Q206L+Y209W+S259D+L262E, wherein the variants have improved stability compared to the protease with SEQ ID NO 1.

According to one embodiment and/or any of the above embodiments the subtilase variant of the invention is selected from the group consisting of:

S9E+N43R+N76D+S188E+A194P+V205I+Q206L+Y209W+S216V+L262E+*275aH+*275bH;

S9E+N43R+N76D+A158E+A194P+N204D+V205I+Q206L+Y209W+S212G+S216V+L262E;

S9E+N43R+N76D+A158E+A194P+N204D+V205I+Q206L+Y209W+S212G+S216V+L262E+*275aH+*275bH

S9E+N43R+N76D+A158E+G160P+V205I+Q206L+Y209W+S259D+N261W+L262E;

S9E+N43R+N76D+A158E+G160P+A194P+N204D+V205I+Q206L+Y209W+S212G+S216V+L262E;

S9E+N43R+N76D+A158E+A194P+V205I+Q206L+Y209W+S259D+N261W+L262E;

S9E+N43R+N76D+A158E+G160P+S161E+A194P+N204D+V205I+Q206L+Y209W+L262E+*275aH+*275bH;

S9E+N43R+N76D+A158E+G160P+S161E+A194P+V205I+Q206L+Y209W+S212G+S216V+L262E;

S9E+N43R+N76D+A158E+G160P+S161E+A194P+V205I+Q206L+Y209W+S212G+S216V+L262E+*275aH+*275bH;

S9E+N43R+N76D+A158E+S161E+A194P+N204D+V205I+Q206L+Y209W+S212G+S216V+L262E+*275aH+*275bH;

S9E+N43R+N76D+G160P+V205I+Q206L+Y209W+S259D+N261W+L262E;

S9E+N43R+N76D+A194P+V205I+Q206L+Y209W+S216V+L262E;

S9E+N43R+N76D+G160P+A194P+N204D+V205I+Q206L+Y209W+S212G+S216V+L262E;

S9E+N43R+N76D+G160P+A194P+N204D+V205I+Q206L+Y209W+S212G+S216V+L262E+*275aH+*275bH;

S9E+N43R+N76D+G160P+S161E+A194P+N204D+V205I+Q206L+Y209W+S212G+S216V+L262E;

S9E+N43R+N76D+G160P+S161E+A194P+N204D+V205I+Q206L+Y209W+S212G+S216V+L262E+*275aH+*275bH;

S9E+N43R+N76D+N204D+V205I+Q206L+Y209W+S259D+N261W+L262E;

S9E+N43R+N76D+G160P+S161E+V205I+Q206L+Y209W+S259D+N261W+L262E;

S9E+N43R+N76D+N117H+A194P+Q206L+Y209W+N238H+S259D+T260A+L262E;

S9E+N43R+N76D+N185E+S188E+A194P+Q206L+ Y209W+S259D+L262E;
S9E+N43R+N76D+V205I+Q206L+Y209W+S216V+ S259D+N261W+L262E;
S9E+N43R+N76D+S161E+V205I+Q206L+Y209W+ S259D+N261W+L262E;
S9E+N43R+N76D+S161E+A194P+N204D+V205I+ Q206L+Y209W+S212G+S216V+L262E;
S9E+N43R+N76D+S161E+A194P+N204D+V205I+ Q206L+Y209W+S212G+S216V+L262E+*275aH+ *275bH;
S9E+N43R+N76D+V205I+Q206L+Y209W+S212G+ S259D+N261W+L262E;
S9E+N43R+N76D+S78H+A194P+V205I+Q206L+ Y209W+S216V+L262E;
S9E+N43R+N76D+N204D+V205I+Q206L+Y209W+ S212G+S216V+S259D+N261W+L262E;
S9E+N76D+V205I+Q206L+Y209W+N261W+L262E;
S9E+N43R+N76D+A158E+G160P+S161E+A194P+ N204D+V205I+Q206L+Y209W+S216V+L262E+ *275aH+*275bH;
S9E+N43R+N76D+A158E+G160P+S161E+A194P+ N204D+V205I+Q206L+Y209W+L262E;
S9E+N43R+N76D+A158E+G160P+S161E+A194P+ N204D+V205I+Q206L+Y209W+S212G+L262E+ *275aH+*275bH;
S9E+N43R+N76D+A194P+Q206L+Y209W+S216V+ L262E;
S9E+N43R+N76D+A158E+G160P+S161E+A194P+ N204D+V205I+Q206L+Y209W+S212G+L262E;
S9E+N43R+N76D+A158E+G160P+S161E+A194P+ N204D+V205I+Q206L+Y209W+S216V+L262E;
S9E+N43R+N76D+A158E+G160P+S161 E+V205I+ Q206L+Y209W+S259D+N261 W+L262E;
S9E+N43R+N76D+A158E+S161E+A194P+N204D+ V205I+Q206L+Y209W+S212G+S216V+L262E;
S9E+N43R+N76D+G115W+A194P+Q206L+Y209W+ L217M+S259D+L262E;
S9E+N43R+N76D+G115W+A194P+Q206L+Y209W+ S216T+S259D+L262E;
S9E+N43R+N76D+A158E+G160P+S161E+A194P+ N204D+V205I+Q206L+Y209W+S212G+S216V+ L262E +*275aH+*275bH;
S9E+N43R+N76D+A158E+G160P+S161E+A194P+ Q206L+Y209W+S259D+L262E+*275aH+*275bH;
S9E+N43R+N76D+A158E+S161E+V205I+Q206L+ Y209W+S259D+N261W+L262E;
S9E+N43R+N76D+A194P+N204D+V205I+Q206L+ Y209W+S212G+S216V+S259D+N261W+L262E;
S9E+N43R+N76D+A194P+Q206L+Y209W+T255E+ S256D+S259D+T260E+N261W+L262E;
S3V+S9R+N76D+H120V+Q182E+N185E+S188E+ V205I+Q206L+Y209W+S216V+S256D+N261W+ L262E;
S9E+N43R+A48H+N76D+N117H+A158E+G160P+ S161E+A194P+N204D+V205I+Q206L+Y209W+ S212G+S216V+N238H+L262E;
S9E+N43R+A48H+N76D+N117H+G160D+S161E+ A194P+N204D+V205I+Q206L+Y209W+S212G+ S216V+N238H+L262E;
S9E+N43R+I72A+N76D+Q141H+S145H+R149H+ A158E+G159P+A194P+L262E;
W6L+S9E+N43R+A72I+N76D+G115W+H120V+ P129D+A158E+G160P+Q182E+N185E+S188E+ Q191N+A194P+N204D+V205I+Q206L+Y209W+ S212G+S216V+T255E+S256D+S259D+T260E+ N261W+L262E;
S9E+G20H+T22H+S24H+N43R+N76D+G160D+ S161E+A194P+N204D+V205I+Q206L+Y209W+ S212G+S216V+L262E;
S9E+N43R+A48H+N76D+N117H+H120D+A158E+ G160P+S161E+A194P+N204D+V205I+Q206L+ Y209W+S212G+S216V+N238H+L262E+*275aR;
S9E+N43R+A48H+N76D+N117H+H120D+A158E+ G160P+S161E+A194P+Q206L+Y209W+N238H+ S259D+L262E+*275aR;
S9E+N43R+A48H+N76D+N117H+P129D+A194P+ N204D+V205I+Q206L+Y209W+S212G+S216V+ N238H+S256D+T260A+L262E;
S9E+N43R+A48H+N76D+N117H+A158E+G160P+ S161E+A194P+N204D+V205I+Q206L+Y209W+ S212G+S216V+N238H+L262E;
S9E+N43R+A48H+N76D+N117H+A158E+G160P+ S161E+A194P+Q206L+Y209W+N238H+S259D+ L262E;
S9E+N43R+A48H+N76D+N117H+G160D+S161E+ A194P+N204D+V205I+Q206L+Y209W+S212G+ S216V+N238H+L262E;
S9E+N43R+A48H+N76D+N117H+G160D+S161E+ A194P+Q206L+Y209W+N238H+S259D+L262E;
S9E+N43R+A48H+N76D+N117H+A194P+G195E+ N204D+V205I+Q206L+Y209W+S212G+S216V+ N238H+L262E;
S9E+N43R+A48H+N76D+N117H+A194P+G195E+ N204D+V205I+Q206L+Y209W+S212G+S216V+ N238H+L262E+*275aR;
S9E+N43R+A48H+N76D+N117H+A194P+N204D+ V205I+Q206L+Y209W+S212G+S216V+N238H+ S256D+T260A+L262E;
S9E+N43R+A48H+N76D+N117H+A194P+Q206L+ Y209W+N238H+S259D+T260A+L262E,
S9E+N43R+G61E+N76D+Q206L+L262E;
S9E+N43R+I72A+N76D+G115W+H120V+P129D+ A158E+G160P+Q182E+N185E+S188E+Q191N+ A194P+N204D+V205I+Q206L+Y209W+S212G+ S216V+T255E+S256D+S259D+T260E+N261W+ L262E;
S9E+N43R+I72A+N76D+G115W+H120V+P129D+ Q182E+N185E+S188E+Q191N+A194P+N204D+ V205I+Q206L+Y209W+S212G+S216V+T255E+ S256D+S259D+T260E+N261W+L262E;
S9E+N43R+I72A+N76D+Q182E+N185E+S188E+ Q191N+A194P+N204D+V205I+Q206L+Y209W+ S212G+S216V+T255E+S256D+S259D+T260E+ N261W+L262E;
S9E+N43R+N76D+Y91H+N117H+A194P+G195E+ N204D+V205I+Q206L+Y209W+S212G+S216V+ N238H+L262E;
S9E+N43R+N76D+N117H+H120D+A158E+G160P+ S161E+A194P+Q206L+Y209W+S259D+L262E;
S9E+N43R+N76D+A194P+Q206L+Y209W+L262E;
S9E+N43R+N76D+A194P+Q206L+Y209W+S256D+ S259D+N261W+L262E;
S9E+N43R+N76D+Q182E+N185E+S188E+Q191N+ A194P+Q206L+Y209W+S259D+L262E,
S9E+N43R+N76D+A158E+G160P+S161E+A194P+ N204D+V205I+Q206L+Y209W+S212G+S216V+ L262E;
S9E+N43R+N76D+A158E+G160P+S161E+A194P+ N204D+V205I+Q206L+Y209W+S212G+S216V+ L262E+*275bH+*275aH;
S9E+N43R+N76D+N117H+H120D+G160D+S161E+ A194P+N204D+V205I+Q206L+Y209W+S212G+ S216V+L262E+*275bH *275aH;

S9E+N43R+N76D+*99aE+P131*-FA194P+Q206L+ Y209W+S259D+L262E;
S9E+N43R+N76D+G115W+H120V+P129D+A194P+ Q206L+Y209W+S259D+L262E;
S9E+N43R+N76D+G115W+H120V+A194P+Q206L+ Y209W+S259D+L262E;
S9E+N43R+N76D+G115W+A194P+Q206L+Y209W+ S259D+L262E;
S9E+N43R+N76D+N117H+H120D+A158E+G160P+ S161E+A194P+N204D+V205I+Q206L+Y209W+ S212G+S216V+L262E;
S9E+N43R+N76D+N117H+H120D+A158E+G160P+ S161E+A194P+N204D+V205I+Q206L+Y209W+ S212G+S216V+L262E+*275aH+*275bH;
S9E+N43R+N76D+N117H+H120D+A158E+G160P+ S161E+A194P+N204D+V205I+Q206L+Y209W+ S212G+S216V+L262E+*275aR;
S9E+N43R+N76D+N117H+H120D+A158E+G160P+ S161E+A194P+Q206L+Y209W+N238H+S259D+ L262E+*275aH+*275bH;
S9E+N43R+N76D+N117H+H120D+A158E+G160P+ S161E+A194P+Q206L+Y209W+S259D+L262E;
S9E+N43R+N76D+N117H+H120D+G160D+S161E+ S163G+A194P+N204D+V205I+Q206L+Y209W+ S212G+S216V+L262E;
S9E+N43R+N76D+N117H+H120D+G160D+S161E+ S163G+A194P+N204D+V205I+Q206L+Y209W+ S212G+S216V+L262E+*275aH+*275bH;
S9E+N43R+N76D+N117H+H120D+G160D+S161E+ A194P+N204D+V205I+Q206L+Y209W+S212G+ S216V+L262E;
S9E+N43R+N76D+N117H+H120D+G160D+S161E+ A194P+N204D+V205I+Q206L+Y209W+S212G+ S216V+L262E+*275aH+*275bH;
S9E+N43R+N76D+N117H+H120D+G160D+S161E+ A194P+Q206L+Y209W+S259D+L262E;
S9E+N43R+N76D+N117H+H120D+G160D+S161E+ A194P+Q206L+Y209W+S259D+L262E+*275aH+ *275bH;
S9E+N43R+N76D+N117H+H120D+A194P+N204D+ V205I+Q206L+Y209W+S212G+S216V+S256D+ T260A+L262E;
S9E+N43R+N76D+N117H+H120D+A194P+N204D+ V205I+Q206L+Y209W+S212G+S216V+S256D+ L262E;
S9E+N43R+N76D+N117H+H120D+A194P+N204D+ V205I+Q206L+Y209W+S212G+S216V+T260A+ L262E;
S9E+N43R+N76D+N117H+H120D+A194P+N204D+ V205I+Q206L+Y209W+S212G+S216V+L262E;
S9E+N43R+N76D+N117H+H120D+A194P+N204D+ V205I+Q206L+Y209W+S212G+S216V+L262E+ *275aH+*275bH;
S9E+N43R+N76D+N117H+H120D+A194P+Q206L+ Y209W+S259D+T260A+L262E+*275aR;
S9E+N43R+N76D+N117H+H120D+A194P+Q206L+ Y209W+S259D+L262E;
S9E+N43R+N76D+N117H+H120D+A194P+Q206L+ Y209W+S259D+L262E+*275aH+*275bH;
S9E+N43R+N76D+P129D+A194P+G195E+Q206L+ Y209W+S259D+L262E;
S9E+N43R+N76D+P129D+A194P+N204D+V205I+ Q206L+Y209W+S212G+S216V+S256D+T260A+ L262E;
S9E+N43R+N76D+P129D+A194P+N204D+V205I+ Q206L+Y209W+S212G+S216V+S256D+T260A+ L262E+*275aH+*275bH;
S9E+N43R+N76D+P129D+A194P+Q206L+Y209W+ S259D+L262E;
S9E+N43R+N76D+P131*+A194P+Q206L+Y209W+ S259D+L262E;
S9E+N43R+N76D+Q137H+S141H+R145H+A158E+ G160P+S161E+A194P+N204D+V205I+Q206L+ Y209W+S212G+S216V+L262E;
S9E+N43R+N76D+Q137H+S141H+R145H+G160D+ S161E+A194P+N204D+V205I+Q206L+Y209W+ S212G+S216V+L262E;
S9E+N43R+N76D+Q137H+S141H+R145H+A194P+ N204D+V205I+Q206L+Y209W+S212G+S216V+ L262E;
S9E+N43R+N76D+Q137H+S141H+R145H+A194P+ Q206L+Y209W+S259D+L262E;
S9E+N43R+N76D+A158E+G160P+S161E+A194P+ Q206L+Y209W+S259D+L262E+*275aH+*275bH;
S9E+N43R+N76D+G160D+S161E+S163G+A194P+ N204D+V205I+Q206L+Y209W+S212G+S216V+ L262E;
S9E+N43R+N76D+G160D+S161E+A194P+N204D+ V205I+Q206L+Y209W+S212G+S216V+L262E;
S9E+N43R+N76D+G160D+S161E+A194P+N204D+ V205I+Q206L+Y209W+S212G+S216V+L262E+ *275aH+*275bH;
S9E+N43R+N76D+G160D+S161E+A194P+Q206L+ Y209W+S259D+L262E;
S9E+N43R+N76D+G160D+S161E+A194P+Q206L+ Y209W+S259D+L262E+*275aH+*275bH;
S9E+N43R+N76D+Q191N+A194P+Q206L+Y209W+ S259D+L262E;
S9E+N43R+N76D+A194P+G195E+N204D+V205I+ Q206L+Y209W+S212G+S216V+S256D+T260A+ L262E;
S9E+N43R+N76D+A194P+G195E+N204D+V205I+ Q206L+Y209W+S212G+S216V+S256D+L262E;
S9E+N43R+N76D+A194P+G195E+N204D+V205I+ Q206L+Y209W+S212G+S216V+T260A+L262E;
S9E+N43R+N76D+A194P+G195E+N204D+V205I+ Q206L+Y209W+S212G+S216V+L262E;
S9E+N43R+N76D+A194P+G195E+N204D+V205I+ Q206L+Y209W+S212G+S216V+L262E+*275aH+ *275bH;
S9E+N43R+N76D+A194P+G195E+Q206L+Y209W+ S259D+L262E+*275aR;
S9E+N43R+N76D+A194P+N204D+V205I+Q206L+ Y209W+S212G+S216V+T255E+S256D+S259D+ N261W+L262E;
S9E+N43R+N76D+A194P+N204D+V205I+Q206L+ Y209W+S212G+S216V+S256D+S259D+T260E+ N261W+L262E;
S9E+N43R+N76D+A194P+N204D+V205I+Q206L+ Y209W+S212G+S216V+S256D+S259D+N261W+ L262E;
S9E+N43R+N76D+A194P+N204D+V205I+Q206L+ Y209W+S212G+S216V+S256D+T260A+L262E+ *275aH+*275bH;
S9E+N43R+N76D+A194P+N204D+V205I+Q206L+ Y209W+S212G+S216V+S256D+T260A+L262E+ *275aR;
S9E+N43R+N76D+A194P+N204D+V205I+Q206L+ Y209W+S212G+S216V+S256D+L262E;
S9E+N43R+N76D+A194P+N204D+V205I+Q206L+ Y209W+S212G+S216V+S259D+N261W+L262E;
S9E+N43R+N76D+A194P+N204D+V205I+Q206L+ Y209W+S212G+S216V+T260A+L262E;

S9E+N43R+N76D+A194P+N204D+V205I+Q206L+
Y209W+S212G+S216V+N261W+L262E;
S9E+N43R+N76D+H120V+Q182E+A194P+V205I+
Q206L+Y209W+S256D+S259D+N261W+L262E;
S9E+N43R+N76D+V205I+Q206L+Y209W+S259D+
N261W+L262E;
S9E+N43R+N76D+A194P+V205I+Q206L+Y209W+
S259D+N261W+L262E;
S9E+N43R+N76D+Q182E+A194P+V205I+Q206L+
Y209W+S256D+S259D+N261W+L262E;
S9E+N43R+N76D+H120V+Q182E+A194P+V205I+
Q206L+Y209W+S256D+N261W+L262E+*275aH+
*275bH;
S3V+N76D+H120V+Q182E+N185E+S188E+V205I+
Q206L+Y209W+S216V+S256D+N261W+L262E;
S9E+N43R+G61E+N76D+G115W+H120V+A194P+
Q206L+S259D+L262E;
S9E+N43R+N76D+Q182E+A194P+V205I+Q206L+
Y209W+S259D+N261W+L262E;
S9E+N43R+N76D+A194P+V205I+Q206L+Y209W+
S216V+M222S+L262E;
S9E+N43R+N76D+A194P+V205I+Q206L+S256D+
S259D+N261W+L262E;
S9E+N18S+N43R+N76D+G115W+H120V+A194P+
V205I+Q206L+S259D+L262E;
S9E+N43R+N76D+G115W+H120V+A194P+V205I+
Q206L+S259D+L262E;
S9E+N43R+N76D+Q182E+A194P+V205I+Q206L+
Y209W+S256D+S259D+N261W+L262E,
S9E+N43R+N76D+S188E+A194P+V205I+Q206L+
Y209W+S216V+L262E;
S9E+N76D+G115W+G160P+Q182E+V205I+Q206L+
Y209W+S256D+T260E+N261W+L262 E
S9E+N43R+N76D+H120T+A194P+Q206L+S256D+
S259D+N261W+L262E;
S9E+N43R+N76D+H120T+A194P+V205I+Q206L+
Y209W+S216V+L262E;
S9E+N76D+G160P+Q182E+V205I+Q206L+Y209W+
S256D+N261W+L262E;
S9E+N43R+N76D+Q182E+A194P+V205I+Q206L+
S259D+N261W+L262E;
S9E+N76D+Q182E+V205I+Q206L+Y209W+S256D+
N261W+L262E;
S9E+N43R+N76D+Q182E+A194P+V205I+Q206L+
S259D+N261W+L262E+*275aH;
S9E+N43R+N76D+Q182E+N185E+S188E+A194P+
Q206L+Y209W+S259D+L262E;
S9E+N43R+N76D+N185E+A194P+V205I+Q206L+
Y209W+S216V+L262E;
S9E+N43R+N76D+A194P+V205I+Q206L+Y209W+
S216V+N261M+L262E;
S9E+N43R+I72A+N76D+A194P+Q206L+S259D+
L262E;
S9E+N43R+N76D+A194P+V205I+Q206L+S259D+
L262E;
S9E+N43R+N76D+H120V+Q182E+A194P+V205I+
Q206L+Y209W+S256D+S259D+N261W+L262E;
S9E+N43R+N76D+H120V+Q182E+A194P+V205I+
Q206L+Y209W+S256D+N261W+L262E+*275aH+
*275bH;
S3V+N76D+H120V+Q182E+N185E+S188E+V205I+
Q206L+Y209W+S216V+S256D+N261W+L262E;
S9E+N43R+N76D+N117H+H120D+A158E+G160P+
S161E+A194P+Q206L+Y209W+S 259D+L262E;
S9E+N43R+N76D+A194P+N204D+V205I+Q206L+
Y209W+S212G+S216V+L262E;
S9E+N43R+N76D+A194P+V205I+Q206L+Y209W+
S212G+S216V+L262E;
S9E+N43R+N76D+A194P+Q206L+Y209W+S212G+
S216V+L262E;
S9E+N43R+N76D+A194P+Q206L+Y209W+S212G+
S259D+L262E;
S9E+N43R+N76D+A194P+Q206L+Y209W+S212G+
L262E;
S9E+N43R+N76D+A194P+Q206L+Y209W+T255E+
S256D+S259D+T260E+N261W+L262E;
S9E+N43R+N76D+A194P N204D+V205I+Q206L+
Y209W+S212G+S216V+L262E;
S9E+N43R+N76D+N185E+S188E+Q191N+A194P+
Q206L+Y209W+S259D+L262E;
S9E+N43R+N76D+Q182E+N185E+S188E+Q191N+
A194P+Q206L+Y209W+S259D+L262E
S9E+N43R N76D N185E S188E Q191 N A194P Q206L
Y209W S259D L262E
S9E+N43R+N76D+G115W+H120V+P129D+A194P+
Q206L+Y209W+S259D+L262E;
S9E+N43R+N76D+A158E+G160P+S161E+A194P+
N204D+V205I+Q206L+Y209W+S212G+S216V+
L262E;
S9E+N43R+N76D+A158E+G160P+S161E+A194P+
N204D+V205I+Q206L+Y209W+S212G+S216V+
L262E+*275bH+*275 aH;
S9E+N43R+N76D+N117H+H120D+G160D+S161E+
A194P+N204D+V205I+Q206L+Y209W+S212G+
S216V;
S9E+N43R+N76D+A194P+Q206L+Y209W+S259D+
T260A+L262E;
S9E+N43R+N76D+A194P+Q206L+Y209W+S259D+
N261W+L262E;
S9E+N43R+N76D+A194P+Q206L+Y209W+S259D+
L262E;
S9E+N43R+N76D+A194P+Q206L+Y209W+S259D+
L262E+*275aH+*275bH;
S9E+N43R+N76D+A194P+Q206L+S259D+L262E;
S9E+N43R+N76D+A194P+Q206L+L262E;
S9E+G61E+N76D+N117H+H120D+G160D+S161E+
S163G+Q206L+L262E+*275aH+*275bH;
S9E+G61E+N76D+P129D+Q206L+S256D+T260A+
L262E+*275aH+*275bH;
S9E+G61E+N76D+P129D+Q206L+T260A+L262E;
S9E+G61E+N76D+P129D+Q206L+L262E+*275aH+
*275bH;
S9E+G61E+N76D+Q137H+S141H+R145H+A158E+
G160P+S161E+Q206L+L262E;
S9E+G61E+N76D+Q137H+S141H+R145H+N204D+
Q206L+Y209W+L262E+*275aR;
S9E+G61E+N76D+Q137H+S141H+R145H+Q206L+
L262E;
S9E+G61E+N76D+A158E+G160P+S161E+Q206L+
L262E;
S9E+G61E+N76D+A158E+G160P+S161E+Q206L+
L262E+*275aH+*275bH;
S9E+G61E+N76D+N204D+Q206L+Y209W+L262E;
S9E+G61E+N76D+N204D+Q206L+Y209W+L262E+
*275aH+*275bH;
S9E+G61E+N76D+Q206L+Y209W+S256D+L262E;
S9E+G61E+N76D+Q206L+S256D+L262E;
S9E+G61E+N76D+Q206L+L262E;
S9E+G61E+N76D+Q206L+L262E+*275aH+*275bH;
S9E+N76D+Q206L+Y209W+N261W+L262E;
S9E+N76D+Q206L+Y209W+L262E; and
S9E+N76D+Q206L+L262E.

Preferred variants include the variants comprising the following mutations compared to SEQ ID NO 1 (numbered according to SEQ ID NO 2):

S9E+N43R+N76D+A194P+Q206L+Y209W+L262E;

S9E+N43R+N76D+V205I+Q206L+Y209W+S259D+ N261W+L262E;

S9E+N43R+N76D+A194P+Q206L+Y209W+T255E+ S256D+S259D+T260E+N261W+L262E;

S9E+N43R+N76D+Q182E+N185E+S188E+Q191N+ A194P+Q206L+Y209W+S259D+L262E;

S9E+N43R+N76D+A194P+Q206L+Y209W+S256D+ S259D+N261W+L262E;

S9E+N43R+N76D+N185E+S188E+Q191N+A194P+ Q206L+Y209W+S259D+L262E;

S9E+N43R+N76D+A158E+G160P+S161E+A194P+ Q206L+Y209W+S259D+L262E+*275bH+* 275aH;

S9E+N43R+N76D+N117H+H120D+A158E+G160P+ S161E+A194P+Q206L+Y209W+S259D+L262E;

S9E+N43R+N76D+A158E+G160P+S161E+A194P+ N204D+V205I+Q206L+Y209W+S212G+S216V+L262E;

S9E+N43R+N76D+A158E+G160P+S161E+A194P+ N204D+V205I+Q206L+Y209W+S212G+S216V+L262E+ *275bH+*275aH;

S9E+N43R+N76D+N117H+H120D+G160D+S161E+ A194P+N204D+V205I+Q206L+Y209W+S212G+S216V+ L262E+*275bH *275aH;

S9E+N43R+N76D+H120V+Q182E+A194P+V205I+ Q206L+Y209W+S256D+S259D+N261W+L262E;

S9E+N43R+N76D+A194P+V205I+Q206L+Y209W+ S259D+N261W+L262E;

S9E+N43R+N76D+Q182E+A194P+V205I+Q206L+ Y209W+S256D+S259D+N261W+L262E;

S9E+N43R+N76D+H120V+Q182E+A194P+V205I+ Q206L+Y209W+S256D+N261W+L262E+*275aH+ *275bH or

S3V+N76D+H120V+Q182E+N185E+S188E+V205I+ Q206L+Y209W+S216V+S256D+N261W+L262E.

The subtilase variants may consist of 150 to 350, e.g., 175 to 330, 200 to 310, 220 to 300, 240 to 290, 260 to 280 or 269, 270, 271, 272, 273, 274 or 275 amino acids.

In one embodiment, the subtilase variant has improved stability, in particular improved storage stability, compared to the parent subtilase. In a preferred embodiment, the subtilase variant has improved stability, in particular improved storage stability, and on par or improved wash performance compared to the parent subtilase.

In one embodiment, the subtilase variant has improved stability, in particular improved wash stability, compared to the parent subtilase. In a preferred embodiment, the subtilase variant has improved stability, in particular improved in storage stability, and on par or improved wash performance compared to the parent subtilase.

In an embodiment, the subtilase variant has improved stability, in particular improved in wash stability, and on par or improved wash performance compared to the parent subtilase wherein wash stability is measured using the 'in wash stability assay' and wash performance is measured using the Automatic Mechanical Stress Assay (AMSA) as described in Example 3.

Parent Protease

The parent or the precursor protease may be any subtilase or even more preferred any subtilisin as defined below.

Enzymes cleaving the amide linkages in protein substrates are classified as proteases, or (interchangeably) peptidases (see Walsh, 1979, Enzymatic Reaction Mechanisms. W. H. Freeman and Company, San Francisco, Chapter 3).

Serine Proteases

A serine protease is an enzyme which catalyzes the hydrolysis of peptide bonds, and in which there is an essential serine residue at the active site (White, Handler and Smith, 1973 "Principles of Biochemistry," Fifth Edition, McGraw-Hill Book Company, NY, pp. 271-272).

The bacterial serine proteases have molecular weights in the 20,000 to 45,000 Dalton range. They are inhibited by diisopropylfluorophosphate. They hydrolyze simple terminal esters and are similar in activity to eukaryotic chymotrypsin, also a serine protease. A more narrow term, alkaline protease, covering a sub-group, reflects the high pH optimum of some of the serine proteases, from pH 9.0 to 11.0 (for review, see Priest, 1977, Bacteriological Rev. 41: 711-753).

Subtilases

A sub-group of the serine proteases tentatively designated subtilases has been proposed by Siezen et al., 1991, Protein Eng. 4:719-737 and Siezen et al., 1997, Protein Science 6:501-523. They are defined by homology analysis of more than 170 amino acid sequences of serine proteases previously referred to as subtilisin-like proteases. A subtilisin was previously often defined as a serine protease produced by Gram-positive bacteria or fungi, and according to Siezen et al. now is a subgroup of subtilases. A wide variety of subtilases have been identified, and the amino acid sequence of a number of subtilases has been determined. For a more detailed description of such subtilases and their amino acid sequences reference is made to Siezen et al. (1997).

Subtilisins

A subgroup of subtilases is subtilisins which are serine proteases from the family S8, in particular from the subfamily S8A, as defined by the MEROPS database (merops.sanger.ac.uk/cgi-bin/famsum?family=S8).

Subtilisin BPN' and subtilisin 309 have the MEROPS numbers S08.034 and S08.003, respectively.

Parent Subtilase

The term "parent subtilase" describes a subtilase defined according to Siezen et al., 1997, Protein Science 6: 501-523. For further details see description of "Subtilases" above. A parent subtilase may also be a subtilase isolated from a natural source, wherein subsequent modifications (such as replacement(s) of the amino acid side chain(s), substitution(s), deletion(s) and/or insertion(s)) have been made while retaining the characteristic of a subtilase. Furthermore, a parent subtilase may be a subtilase which has been prepared by the DNA shuffling technique, such as described by Ness et al., 1999, Nature Biotechnology, 17: 893-896.

Alternatively, the term "parent subtilase" may be termed "precursor subtilase" and is used to describe the starting protease into which mutations are made to obtain the variant of the invention. The parent subtilase is preferably of the subtilisin subgroups.

One subgroup of the subtilases, I-S1 or "true" subtilisins, include the "classical" subtilisins, such as subtilisin 168 (BSS168), subtilisin BPN', subtilisin Carlsberg (ALCALASE®, Novozymes A/S), and subtilisin DY (BSSDY). BPN' is subtilisin BPN' from B. amyloliquefaciens, Subtilisin BPN' has the amino acid sequence of SEQ ID NO: 2. A further subgroup of the subtilases, I-S2 or high alkaline subtilisins, is recognized by Siezen et al. (supra). Sub-group I-S2 proteases are described as highly alkaline subtilisins and include enzymes such as subtilisin PB92 (BAALKP) (MAXACAL®, Genencor International Inc.), subtilisin 147 (BLS147) (ESPERASE®, Novozymes A/S), alkaline elastase YaB (BSEYAB) and subtilisin 309 (SAVINASE®, Novozymes A/S) having the amino acid sequence SEQ ID NO: 1.

For reference, Table 1 below gives a list of some acronyms for various subtilases mentioned herein. For further acronyms, see Siezen et al. (1991 and 1997).

TABLE 1

Acronyms of various subtilases

| Organism | Enzyme | Acronym | Sequence |
| --- | --- | --- | --- |
| *Bacillus subtilis* 168 | subtilisin I168, apr | BSS168 | SEQ ID NO: 3 |
| *Bacillus amyloliquefaciens* | subtilisin BPN' (NOVO) | BASBPN | SEQ ID NO: 2 |
| *Bacillus subtilis* DY | subtilisin DY | BSSDY | SEQ ID NO: 4 |
| *Bacillus licheniformis* | subtilisin Carlsberg | BLSCAR | SEQ ID NO: 5 |
| *Bacillus lentus* | subtilisin 309 | BLSAVI | SEQ ID NO: 1 |
| *Bacillus lentus* | subtilisin 147 | BLS147 | SEQ ID NO: 6 |
| *Bacillus alcalophilus* PB92 | subtilisin PB92 | BAPB92 | SEQ ID NO: 7 |
| *Bacillus* YaB | alkaline elastase YaB | BYSYAB | SEQ ID NO: 8 |
| *Bacillus* sp. NKS-21 | subtilisin ALP I | BSAPRQ | SEQ ID NO: 9 |
| *Bacillus* sp. G-825-6 | subtilisin Sendai | BSAPRS | SEQ ID NO: 10 |
| *Thermoactinomyces vulgaris* | Thermitase | TVTHER | SEQ ID NO: 11 |

Homologous Subtilase Sequences

The homology between two amino acid sequences is in this context described by the parameter "identity" for purposes of the present invention, the degree of identity between two amino acid sequences is determined using the Needleman-Wunsch algorithm as described above. The output from the routine is besides the amino acid alignment the calculation of the "Percent Identity" between the two sequences.

Based on this description it is routine for a person skilled in the art to identify suitable homologous subtilases, which can be modified according to the invention.

The parent protease may be a polypeptide having at least 60% sequence identity to the polypeptide of SEQ ID NO: 1, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have protease activity. In one aspect, the amino acid sequence of the parent differs by up to 10 amino acids, e.g., 1, 2, 3, 4, 5, 6, 7, 8, 9, or 10, from the polypeptide of SEQ ID NO: 1. In another aspect, the parent comprises or consists of the amino acid sequence of SEQ ID NO: 1.

The parent protease may be a polypeptide having at least 60% sequence identity to the polypeptide of SEQ ID NO: 2, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have protease activity. In one aspect, the amino acid sequence of the parent differs by up to 10 amino acids, e.g., 1, 2, 3, 4, 5, 6, 7, 8, 9, or 10, from the polypeptide of SEQ ID NO: 2. In another aspect, the parent comprises or consists of the amino acid sequence of SEQ ID NO: 2.

The parent protease may be a polypeptide having at least 60% sequence identity to the polypeptide of SEQ ID NO: 3, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have protease activity. In one aspect, the amino acid sequence of the parent differs by up to 10 amino acids, e.g., 1, 2, 3, 4, 5, 6, 7, 8, 9, or 10, from the polypeptide of SEQ ID NO: 3. In another aspect, the parent comprises or consists of the amino acid sequence of SEQ ID NO: 3.

The parent protease may be a polypeptide having at least 60% sequence identity to the polypeptide of SEQ ID NO: 4, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have protease activity. In one aspect, the amino acid sequence of the parent differs by up to 10 amino acids, e.g., 1, 2, 3, 4, 5, 6, 7, 8, 9, or 10, from the polypeptide of SEQ ID NO: 4. In another aspect, the parent comprises or consists of the amino acid sequence of SEQ ID NO: 4.

The parent protease may be a polypeptide having at least 60% sequence identity to the polypeptide of SEQ ID NO: 5, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have protease activity. In one aspect, the amino acid sequence of the parent differs by up to 10 amino acids, e.g., 1, 2, 3, 4, 5, 6, 7, 8, 9, or 10, from the polypeptide of SEQ ID NO: 5. In another aspect, the parent comprises or consists of the amino acid sequence of SEQ ID NO: 5.

The parent protease may be a polypeptide having at least 60% sequence identity to the polypeptide of SEQ ID NO: 6, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have protease activity. In one aspect, the amino acid sequence of the parent differs by up to 10 amino acids, e.g., 1, 2, 3, 4, 5, 6, 7, 8, 9, or 10, from the polypeptide of SEQ ID NO: 6. In another aspect, the parent comprises or consists of the amino acid sequence of SEQ ID NO: 6.

The parent protease may be a polypeptide having at least 60% sequence identity to the polypeptide of SEQ ID NO: 7, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have protease activity. In one aspect, the amino acid sequence of the parent differs by up to 10 amino acids, e.g., 1, 2, 3, 4, 5, 6, 7, 8, 9, or 10, from the polypeptide of SEQ ID NO: 7. In another aspect, the parent comprises or consists of the amino acid sequence of SEQ ID NO: 7.

The parent protease may be a polypeptide having at least 60% sequence identity to the polypeptide of SEQ ID NO: 8, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have protease activity. In one aspect, the amino acid sequence of the parent differs by up to 10 amino acids, e.g., 1, 2, 3, 4, 5, 6, 7, 8, 9, or 10, from the polypeptide of SEQ ID NO: 8. In another aspect, the parent comprises or consists of the amino acid sequence of SEQ ID NO: 8.

The parent protease may be a polypeptide having at least 60% sequence identity to the polypeptide of SEQ ID NO: 9, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have protease activity. In one aspect, the amino acid sequence of the parent differs by up to 10 amino acids, e.g., 1, 2, 3, 4, 5, 6, 7, 8, 9, or 10, from the polypeptide of SEQ ID NO: 9. In another aspect, the parent comprises or consists of the amino acid sequence of SEQ ID NO: 9.

The parent protease may be a polypeptide having at least 60% sequence identity to the polypeptide of SEQ ID NO: 10, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have protease activity. In one aspect, the amino acid sequence of the parent differs by up to 10 amino acids, e.g., 1, 2, 3, 4, 5, 6, 7, 8, 9, or 10, from the polypeptide of SEQ ID NO: 10. In another aspect, the parent comprises or consists of the amino acid sequence of SEQ ID NO: 10.

The parent protease may be a polypeptide having at least 60% sequence identity to the polypeptide of SEQ ID NO: 11, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have protease activity. In one aspect, the amino acid sequence of the parent differs by up to 10 amino acids, e.g., 1, 2, 3, 4, 5, 6, 7, 8, 9, or 10, from the polypeptide of SEQ ID NO: 11. In another aspect, the parent comprises or consists of the amino acid sequence of SEQ ID NO: 11.

The polypeptide may be a hybrid polypeptide in which a region of one polypeptide is fused at the N-terminus or the C-terminus of a region of another polypeptide.

The parent subtilase may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial protease. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus*, or *Streptomyces* protease, or a Gram-negative bacterial polypeptide such as a *Campylobacter, E. coli, Flavobacterium, Fusobacterium, Helicobacter, Ilyobacter, Neisseria, Pseudomonas, Salmonella*, or *Ureaplasma* protease.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* protease Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a subtilase variant having protease activity, comprising:

(a) introducing into a parent subtilase the substitutions X9E+X206L+X262E, wherein the position corresponds to the position of SEQ ID NO: 2, and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., US 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that when introduced into the host cell is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis dal* genes, or markers that confer antibiotic resistance such as ampicillin, chloramphenicol, kanamycin, neomycin, spectinomycin or tetracycline resistance.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any Bacillus cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megate-*

*rium, Bacillus pumilus, Bacillus stearothermophilus, Bacillus subtilis*, and *Bacillus thuringiensis* cells.

The bacterial host cell may also be any Streptococcus cell including, but not limited to, *Streptococcus equisimilis, Streptococcus pyogenes, Streptococcus uberis*, and *Streptococcus equi* subsp. *Zooepidemicus* cells.

The bacterial host cell may also be any Streptomyces cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a Streptococcus cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants with protease activity. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Compositions

The present invention also relates to a composition comprising a subtilase variant of the present invention. In an embodiment the composition is a detergent composition.

The choice of additional components is within the skill of the artisan and includes conventional ingredients, including the exemplary non-limiting components set forth below. The choice of components may include, for fabric care, the consideration of the type of fabric to be cleaned, the type and/or degree of soiling, the temperature at which cleaning is to take place, and the formulation of the detergent product.

In a particular embodiment, a detergent composition comprises a subtilase variant of the invention and one or more detergent components, such as surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers.

In one embodiment of the present invention, the subtilase variant of the present invention may be added to a detergent composition in an amount corresponding to 0.01-200 mg of enzyme protein per liter of wash liquor, preferably 0.05-50 mg of enzyme protein per liter of wash liquor, in particular 0.1-10 mg of enzyme protein per liter of wash liquor.

A composition for use in automatic dishwash (ADW), for example, may include 0.0001%-50%, such as 0.001%-30%, such as 0.01%-20%, such as 0.5-15% of enzyme protein by weight of the composition.

A composition for use in laundry granulation, for example, may include 0.0001%-50%, such as 0.001%-20%, such as 0.01%-10%, such as 0.05%-5% of enzyme protein by weight of the composition.

A composition for use in laundry liquid, for example, may include 0.0001%-10%, such as 0.001-7%, such as 0.1%-5% of enzyme protein by weight of the composition.

The enzymes such as the subtilase variant of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708 or the variants according to the invention may be stabilized using peptide aldehydes or ketones such as described in WO 2005/105,826 and WO 2009/118,375.

A variant of the present invention may also be incorporated in the detergent formulations disclosed in WO 97/07202, which is hereby incorporated by reference.

The subtilase variants of the invention may be formulated in liquid laundry compositions such as a liquid laundry compositions composition comprising:
 a) at least 0.01 mg of active subtilase variant per litre detergent,
 b) 2 wt % to 60 wt % of at least one surfactant
 c) 5 wt % to 50 wt % of at least one builder The detergent composition may be formulated into a granular detergent for laundry.

Such detergent may comprise;
 a) at least 0.01 mg of active protease variant per gram of composition
 b) anionic surfactant, preferably 5 wt % to 50 wt %
 c) nonionic surfactant, preferably 1 wt % to 8 wt %
 d) builder preferably 5 wt % to 40 wt % and preferably such as carbonates, zeolites, phosphate builder, calcium sequestering builders or complexing agents Although components mentioned below are categorized by general header according to a particular functionality, this is not to be construed as a limitation, as a component may comprise additional functionalities as will be appreciated by the person skilled in the art.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized. Surfactants lower the surface tension in the detergent, which allows the stain being cleaned to be lifted and dispersed and then washed away.

When included therein, the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein, the detergent will usually contain from about 0% to about 10% by weight of a cationic surfactant. Non-limiting examples of cationic surfactants include alklydimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, and combinations thereof.

When included therein, the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein, the detergent will usually contain from about 0% to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

When included therein, the detergent will usually contain from about 0% to about 10% by weight of a zwitterionic surfactant. Non-limiting examples of zwitterionic surfactants include betaine, alkyldimethylbetaine, sulfobetaine, and combinations thereof.

Builders and Co-Builders

The detergent composition may contain about 0-65% by weight, such as about 5% to about 45% of a detergent builder or co-builder, or a mixture thereof. In a dish wash deteregent, the level of builder is typically 40-65%, particularly 50-65%. Builders and chelators soften, e.g., the wash water by removing the metal ions form the liquid. The builder and/or co-builder may particularly be a chelating agent that forms water-soluble complexes with Ca and Mg. Any builder and/or co-builder known in the art for use in laundry detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as iminodiethanol), triethanolamine (TEA, also known as 2,2',2"-nitrilotriethanol), and carboxymethyl inulin (CMI), and combinations thereof.

The detergent composition may also contain 0-20% by weight, such as about 5% to about 10%, of a detergent co-builder, or a mixture thereof. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetri- aminepentaacetic acid (DTPA), iminodisuccinic acid (IDS), ethylenediamine-N,N'-disuccinic acid (EDDS), methylgly- cinediacetic acid (MGDA), glutamic acid-N,N-diacetic acid (GLDA), 1-hydroxyethane-1,1-diphosphonic acid (HEDP), ethylenediaminetetra-(methylenephosphonic acid) (EDT- MPA), diethylenetriaminepentakis (methylenephosphonic acid) (DTPMPA or DTMPA), N-(2-hydroxyethyl)iminodi- acetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sul- foethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N, N-di- acetic acid (α-ALDA), serine-N, N-diacetic acid (SEDA), isoserine-N, N-diacetic acid (ISDA), phenylalanine-N, N-diacetic acid (PHDA), anthranilic acid-N, N-diacetic acid (ANDA), sulfanilic acid-N, N-diacetic acid (SLDA), tau- rine-N, N-diacetic acid (TUDA) and sulfomethyl-N, N-di- acetic acid (SMDA), N-(2-hydroxyethyl)-ethylidenedi- amine-N, N, N'-triacetate (HEDTA), diethanolglycine (DEG), diethylenetriamine penta(methylenephosphonic acid) (DTPMP), aminotris(methylenephosphonic acid) (ATMP), and combinations and salts thereof. Further exem- plary builders and/or co-builders are described in, e.g., WO 2009/102,854 and U.S. Pat. No. 5,977,053

The subtilase variants of the invention may also be formulated into a dish wash composition preferably an automatic dish wash composition (ADW) comprising:
a) at least 0.01 mg of active protease variant according to the invention, and
b) 10-50 wt % builder preferably selected from citric acid, methylglycine-N,N-diacetic acid (MGDA) and/or glutamic acid-N,N-diacetic acid (GLDA) and mixtures thereof, and
c) at least one bleach component.

Bleaching Systems

The detergent may contain 0-50% by weight, such as about 0.1% to about 25%, of a bleaching system. Bleach systems remove discolor often by oxidation, and many bleaches also have strong bactericidal properties, and are used for disinfecting and sterilizing. Any bleaching system known in the art for use in laundry detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosul- furic acids and salts, for example, Oxone (R), and mixtures thereof. Non-limiting examples of bleaching systems include peroxide-based bleaching systems, which may com- prise, for example, an inorganic salt, including alkali metal salts such as sodium salts of perborate (usually mono- or tetra-hydrate), percarbonate, persulfate, perphosphate, per- silicate salts, in combination with a peracid-forming bleach activator. The term bleach activator is meant herein as a compound which reacts with peroxygen bleach like hydro- gen peroxide to form a peracid. The peracid thus formed constitutes the activated bleach. Suitable bleach activators to be used herein include those belonging to the class of esters amides, imides or anhydrides. Suitable examples are tet- racetylethylene diamine (TAED), sodium 4-[(3,5,5-trimeth- ylhexanoyl)oxy]benzene sulfonate (ISONOBS), diperoxy dodecanoic acid, 4-(dodecanoyloxy)benzenesulfonate (LOBS), 4-(decanoyloxy)benzenesulfonate, 4-(decanoy- loxy)benzoate (DOBS), 4-(nonanoyloxy)-benzenesulfonate (NOBS), and/or those disclosed in WO 98/17767. A par- ticular family of bleach activators of interest was disclosed in EP 624154 and particulary preferred in that family is acetyl triethyl citrate (ATC). ATC or a short chain triglyc- eride like triacetin has the advantage that it is environmental friendly as it eventually degrades into citric acid and alcohol. Furthermore acetyl triethyl citrate and triacetin has a good hydrolytical stability in the product upon storage and it is an efficient bleach activator. Finally ATC provides a good building capacity to the laundry additive. Alternatively, the bleaching system may comprise peroxyacids of, for example, the amide, imide, or sulfone type. The bleaching system may also comprise peracids such as 6-(phthalimido) peroxyhexanoic acid (PAP). The bleaching system may also include a bleach catalyst or a booster.

Some non-limiting examples of bleach catalysts that may be used in the compositions of the present invention include manganese oxalate, manganese acetate, manganese-colla- gen, cobalt-amine catalysts and manganese triazacy- clononane (MnTACN) catalysts; particularly preferred are complexes of manganese with 1,4,7-trimethyl-1,4,7-triaza- cyclononane (Me3-TACN) or 1,2,4,7-tetramethyl-1,4,7-tri- azacyclononane (Me4-TACN), in particular Me3-TACN, such as the dinuclear manganese complex [(Me3-TACN)Mn (O)3Mn(Me3-TACN)](PF6)2, and [2,2',2"-nitrilotris(eth- ane-1,2-diylazanylylidene-κN-methanylylidene)tripheno- lato-κ3O]manganese(III). The bleach catalysts may also be other metal compounds, such as iron or cobalt complexes.

In some embodiments, the bleach component may be an organic catalyst selected from the group consisting of organic catalysts having the following formula:

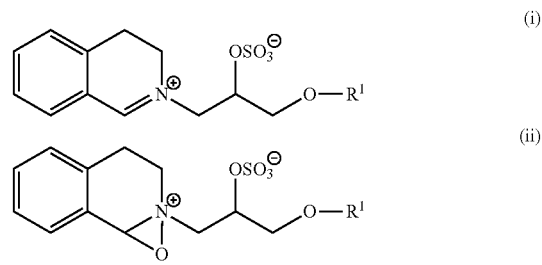

(iii) and mixtures thereof; wherein each $R^1$ is indepen- dently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexylde- cyl, n-dodecyl, n-tetradecyl, n-hexadecyl, n-octadecyl, iso- nonyl, iso-decyl, iso-tridecyl and iso-pentadecyl. Other exemplary bleaching systems are described, e.g., in WO 2007/087,258, WO 2007/087,244, WO 2007/087,259 and WO 2007/087,242. Suitable photobleaches may for example be sulfonated zinc phthalocyanine.

Hydrotropes

A hydrotrope is a compound that solubilizes hydrophobic compounds in aqueous solutions (or oppositely, polar substances in a non-polar environment). Typically, hydrotropes have both hydrophilic and hydrophobic characters (so-called amphiphilic properties as known from surfactants); however the molecular structure of hydrotropes generally do not favour spontaneous self-aggregation, see, e.g., review by Hodgdon and Kaler, 2007, *Current Opinion in Colloid & Interface Science* 12: 121-128. Hydrotropes do not display a critical concentration above which self-aggregation occurs as found for surfactants and lipids forming micellar, lamellar or other well defined meso-phases. Instead, many hydrotropes show a continuous-type aggregation process where the sizes of aggregates grow as concentration increases. However, many hydrotropes alter the phase behaviour, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allows for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130,575. Salts of the above-mentioned polymers are also contemplated.

Fabric Hueing Agents

The detergent compositions of the present invention may also include fabric hueing agents such as dyes or pigments, which when formulated in detergent compositions can deposit onto a fabric when the fabric is contacted with a wash liquor comprising the detergent compositions and thus altering the tint of the fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/003,274, WO 2005/003,275, WO 2005/003,276 and EP 1876226 (hereby incorporated by reference). The detergent composition preferably comprises from about 0.00003 wt. % to about 0.2 wt. %, from about 0.00008 wt. % to about 0.05 wt. %, or even from about 0.0001 wt. % to about 0.04 wt. % fabric hueing agent. The composition may comprise from 0.0001 wt % to 0.2 wt. % fabric hueing agent, this may be especially preferred when the composition is in the form of a unit dose pouch. Suitable hueing agents are also disclosed in, e.g., WO 2007/087257 and WO 2007/087,243.

Additional Enzymes

The detergent additive as well as the detergent composition may comprise one or more (additional) enzymes such as an amylase, arabinase, carbohydrase, cellulase (e.g., endoglucanase), cutinase, galactanase, haloperoxygenase, lipase, mannanase, oxidase, e.g., laccase and/or peroxidase, pectinase, pectin lyases, protease, xylanase, xanthanase, and xyloglucanase.

In general, the properties of the selected enzyme(s) should be compatible with the selected detergent (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 495257, EP 531372, WO 96/11262, WO 96/29397, WO 98/08940. Other examples are cellulase variants such as those described in WO 94/07998, EP 531315, U.S. Pat. Nos. 5,457,046, 5,686,593, 5,763,254, WO 95/24471, WO 98/12307 and PCT/DK98/00299.

Examples of cellulases exhibiting endo-beta-1,4-glucanase activity (EC 3.2.1.4) are described in WO 02/99091.

Other examples of cellulases include the family 45 cellulases described in WO 96/29397, and especially variants thereof having substitution, insertion and/or deletion at one or more of the positions corresponding to the following positions in SEQ ID NO: 8 of WO 02/99091: 2, 4, 7, 8, 10, 13, 15, 19, 20, 21, 25, 26, 29, 32, 33, 34, 35, 37, 40, 42, 42a, 43, 44, 48, 53, 54, 55, 58, 59, 63, 64, 65, 66, 67, 70, 72, 76, 79, 80, 82, 84, 86, 88, 90, 91, 93, 95, 95d, 95h, 95j, 97, 100, 101, 102, 103, 113, 114, 117, 119, 121, 133, 136, 137, 138, 139, 140a, 141, 143a, 145, 146, 147, 150e, 150j, 151, 152, 153, 154, 155, 156, 157, 158, 159, 160c, 160e, 160k, 161, 162, 164, 165, 168, 170, 171, 172, 173, 175, 176, 178, 181, 183, 184, 185, 186, 188, 191, 192, 195, 196, 200, and/or 20, preferably selected among P19A, G20K, Q44K, N48E, Q119H or Q146 R.

Commercially available cellulases include Celluzyme™, and Carezyme™ (Novozymes A/S), Clazinase™, and Puradax HA™ (Genencor International Inc.), and KAC-500 (B)™ (Kao Corporation).

Proteases

The composition may comprise one or more additional proteases including those of bacterial, fungal, plant, viral or animal origin, e.g., vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from, e.g., family M4 or other metalloprotease such as those from M5, M7 or M8 families.

Examples of metalloproteases are the neutral metalloprotease as described in WO 2007/044,993 (Genencor Int.) such as those derived from *Bacillus amyloliquefaciens*.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect Prime®, Purafect MA®, Purafect Ox®, Purafect OxP®, Puramax®, Properase®, FN2®, FN3®, FN4®, Excellase®, Eraser®, Opticlean® and Optimase® (Danisco/DuPont), Axapem™ (Gist-Brocades N.V.), BLAP (sequence shown in FIG. 29 of U.S. Pat. No. 5,352,604) and variants hereof (Henkel AG) and KAP (*Bacillus alkalophilus* subtilisin) from Kao.

Lipases and Cutinases

Suitable lipases and cutinases include those of bacterial or fungal origin. Chemically modified or protein engineered mutant enzymes are included. Examples include lipase from *Thermomyces*, e.g., from *T. lanuginosus* (previously named *Humicola lanuginosa*) as described in EP 258068 and EP 305216, cutinase from *Humicola*, e.g., *H. insolens* (WO 96/13580), lipase from strains of *Pseudomonas* (some of these now renamed to *Burkholderia*), e.g., *P. alcaligenes* or *P. pseudoalcaligenes* (EP 218272), *P. cepacia* (EP 331376), *P.* sp. strain SD705 (WO 95/06720 & WO 96/27002), *P. wisconsinensis* (WO 96/12012), GDSL-type *Streptomyces* lipases (WO 2010/065,455), cutinase from *Magnaporthe grisea* (WO 2010/107560), cutinase from *Pseudomonas mendocina* (U.S. Pat. No. 5,389,536), lipase from *Thermobifida fusca* (WO 2011/084,412), *Geobacillus stearothermophilus* lipase (WO 2011/084,417), lipase from *Bacillus subtilis* (WO 2011/084,599), and lipase from *Streptomyces griseus* (WO 2011/150,157) and *S. pristinaespiralis* (WO 2012/137,147).

Other examples are lipase variants such as those described in EP 407225, WO 92/05249, WO 94/01541, WO 94/25578, WO 95/14783, WO 95/30744, WO 95/35381, WO 95/22615, WO 96/00292, WO 97/04079, WO 97/07202, WO 00/34450, WO 00/60063, WO 01/92502, WO 2007/87508 and WO 2009/109,500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g., acyltransferases with homology to *Candida antarctica* lipase A (WO 2010/111, 143), acyltransferase from *Mycobacterium smegmatis* (WO 2005/056,782), perhydrolases from the CE 7 family (WO 2009/067,279), and variants of the *M. smegmatis* perhydrolase in particular the S54V variant used in the commercial product Gentle Power Bleach from Huntsman Textile Effects Pte Ltd (WO 2010/100,028).

Amylases

Suitable amylases which can be used together with the subtilase variants of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/19467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/10355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066,594 and residues 36-483 of the *B. licheniformis* alpha-amylase shown in SEQ ID NO: 4 of WO 2006/066,594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066,594 and residues 36-483 of SEQ ID NO: 4 are those having the substitutions:

M197T;

H156Y+A181T+N190F+A209V+Q264S; or

G48A+T49I+G107A+H156Y+A181T+N190F+I201F+A209V+Q264S.

Other suitable amylases are amylases having the sequence of SEQ ID NO: 6 in WO 99/19467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/23873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/23873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 2008/153,815, SEQ ID NO: 10 in WO 01/66712 or variants thereof having 90% sequence identity to SEQ ID NO: 2 of WO 2008/153,815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 2009/061,380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128C+K178L+T182G+F202Y+Y305R+D319T+ G475K;
S125A+N128C+K178L+T182G+Y305R+G475K; or
S125A+N128C+T131I+T165I+K178L+T182G+Y305R+ G475K, wherein the variants are C-terminally truncated and optionally further comprise a substitution at position 243 and/or a deletion at position 180 and/or position 181.

Further suitable amylases are amylases having SEQ ID NO: 1 of WO 2013/184,577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or a deletion in position R178 and/or S179 or of T180 and/or G181. Most preferred amylase variants of SEQ ID NO: 1 comprise the substitutions:

E187P+I203Y+G476K
E187P+I203Y+R458N+T459S+D460T+G476K
and optionally further comprise a substitution at position 241 and/or a deletion at position 178 and/or position 179.

Further suitable amylases are amylases having SEQ ID NO: 1 of WO 2010/104,675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478.

More preferred variants of SEQ ID NO: 1 are those having the substitution in one of more of the following positions: N21D, D97N, V128I K177L, M200L, L204YF, E242QA, G477K and G478K and/or a deletion in position R179 and/or S180 or of I181 and/or G182. Most preferred amylase variants of SEQ ID NO: 1 comprise the substitutions N21D+D97N+V128I, and optionally further comprise a substitution at position 200 and/or a deletion at position 180 and/or position 181.

Other suitable amylases are the alpha-amylase having SEQ ID NO: 12 in WO 01/66712 or a variant having at least 90% sequence identity to SEQ ID NO: 12. Preferred amylase variants are those having a substitution, a deletion or an insertion in one of more of the following positions of SEQ ID NO: 12 in WO 01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO 2011/098,531, WO 2013/001,078 and WO 2013/001,087. Commercially available amylases are Duramyl™, Termamyr™, Fungamyl™, Stainzyme™, Stainzyme Plus™, Natalase™, Liquozyme X and BAN™ (from Novozymes A/S), and Rapidase™, Purastar™/Effectenz™, Powerase, Preferenz S1000, Preferenz S100 and Preferenz S110 (from Genencor International Inc./DuPont).

Peroxidases/Oxidases

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238216.

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

Dispersants: The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents: The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent whitening agent: The detergent compositions of the present invention will preferably also contain additional components that may tint articles being cleaned, such as fluorescent whitening agent or optical brighteners. Where present the brightener is preferably at a level of about 0.01% to about 05%. Any fluorescent whitening agent suitable for use in a laundry detergent composition may be used in the composition of the present invention. The most commonly used fluorescent whitening agents are those belonging to the classes of diaminostilbene-sulphonic acid derivatives, diarylpyrazoline derivatives and bisphenyl-distyryl derivatives. Examples of the diaminostilbene-sulphonic acid derivative type of fluorescent whitening agents include the sodium salts of: 4,4'-bis-(2-diethanolamino-4-anilino-s-triazin-6-ylamino) stilbene-2,2'-disulphonate; 4,4'-bis-(2,4-dianilino-s-triazin-6-ylamino) stilbene-2.2'-disulphonate; 4,4'-bis-(2-anilino-4(N-methyl-N-2-hydroxy-ethylamino)-s-triazin-6-ylamino) stilbene-2,2'-disulphonate, 4,4'-bis-(4-phenyl-2,1,3-triazol-2-yl)stilbene-2,2'-disulphonate; 4,4'-bis-(2-anilino-4(1-methyl-2-hydroxy-ethylamino)-s-triazin-6-ylamino) stilbene-2,2'-disulphonate and 2-(stilbyl-4"-naptho-1,2':4, 5)-1,2,3-trizole-2"-sulphonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4 anilino-s-triazin-6-ylamino) stilbene disulphonate. Tinopal CBS is the disodium salt of 2,2'-bis-(phenyl-styryl) disulphonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt. % to upper levels of 0.5 or even 0.75 wt. %.

Soil release polymers: The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087,523 (hereby incorporated by reference). Furthermore random graft co-polymers are suitable soil release polymers Suitable graft co-polymers are described in more detail in WO 2007/138,054, WO 2006/108,856 and WO 2006/113,314 (hereby incorporated by reference). Other soil release polymers are substituted polysaccharide structures especially substituted cellulosic structures such as modified cellulose deriviaties such as those described in EP 1867808 or WO 03/040,279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-redeposition agents: The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid. There are a number of detergent formulation forms such as layers (same or different phases), pouches, as well as forms for machine dosing unit.

Pouches can be configured as single or multicompartments. It can be of any form, shape and material which is suitable for hold the composition, e.g., without allowing the release of the composition from the pouch prior to water contact. The pouch is made from water soluble film which encloses an inner volume. The inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxyprpyl methyl cellulose (HPMC). Preferably the level of polymer in the film for example PVA is at least about 60%.

Preferred average molecular weight will typically be about 20,000 to about 150,000. Films can also be of blend compositions comprising hydrolytically degradable and water soluble polymer blends such as polyactide and polyvinyl alcohol (known under the Trade reference M8630 as sold by Chris Craft In. Prod. of Gary, Ind., US) plus plasticisers like glycerol, ethylene glycerol, Propylene glycol, sorbitol and mixtures thereof. The pouches can comprise a solid laundry detergent composition or part components and/or a liquid cleaning composition or part components separated by the water soluble film. The compartment for liquid components can be different in composition than compartments containing solids. See, e.g., US 2009/0011970.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Laundry Soap Bars

The enzymes of the invention may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e., if a solid object (e.g., laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants, e.g., anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g., a two stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix containing a soap, an enzyme, optionally one or more additional enzymes, a protease inhibitor, and a salt of a monovalent cation and an organic anion may be prepared and the mixture is then plodded. The enzyme and optional additional enzymes may be added at the same time as the protease inhibitor for example in liquid form. Besides the mixing step and the plodding step, the process may further comprise the steps of milling, extruding, cutting, stamping, cooling and/or wrapping.

Granular Detergent Formulations

A granular detergent may be formulated as described in WO 2009/092,699, EP 1705241, EP 1382668, WO 2007/001,262, US 6,472,364, WO 2004/074,419 or WO 2009/102,854. Other detergent formulations are described in WO 2009/124,162, WO 2009/124,163, WO 2009/117,340, WO 2009/117,341, WO 2009/117,342, WO 2009/072,069, WO 2009/063,355, WO 2009/132,870, WO 2009/121,757, WO 2009/112,296, WO 2009/112,298, WO 2009/103,822, WO 2009/087,033, WO 2009/050,026, WO 2009/047,125, WO 2009/047,126, WO 2009/047,127, WO 2009/047,128, WO 2009/021,784, WO 2009/010,375, WO 2009/000,605, WO 2009/122,125, WO 2009/095,645, WO 2009/040,544, WO 2009/040,545, WO 2009/024,780, WO 2009/004,295, WO 2009/004,294, WO 2009/121,725, WO 2009/115,391, WO 2009/115,392, WO 2009/074,398, WO 2009/074,403, WO 2009/068,501, WO 2009/065,770, WO 2009/021,813, WO 2009/030,632, WO 2009/015,951, WO 2011/025,615, WO 2011/016,958, WO 2011/005,803, WO 2011/005,623, WO 2011/005,730, WO 2011/005,844, WO 2011/005,904, WO 2011/005,630, WO 2011/005,830, WO 2011/005,912, WO 2011/005,905, WO 2011/005,910, WO 2011/005,813, WO 2010/135,238, WO 2010/120,863, WO 2010/108,002, WO 2010/111,365, WO 2010/108,000, WO 2010/107,635, WO 2010/090,915, WO 2010/033,976, WO 2010/033,746, WO 2010/033,747, WO 2010/033,897, WO 2010/033,979, WO 2010/030,540, WO 2010/030,541, WO 2010/030,539, WO 2010/024,467, WO 2010/024,469, WO 2010/024,470, WO 2010/025,161, WO 2010/014,395, WO 2010/044,905, WO 2010/145,887, WO 2010/142,503, WO 2010/122,051, WO 2010/102,861, WO 2010/099,997, WO 2010/084,039, WO 2010/076,292, WO 2010/069,742, WO 2010/069,718, WO 2010/069,957, WO 2010/057,784, WO 2010/054,986, WO 2010/018,043, WO 2010/003,783, WO 2010/003,792, WO 2011/023,716, WO 2010/142,539, WO 2010/118,959, WO 2010/115,813, WO 2010/105,942, WO 2010/105,961, WO 2010/105,962, WO 2010/094,356, WO 2010/084,203, WO 2010/078,979, WO 2010/072,456, WO 2010/069,905, WO 2010/076,165, WO 2010/072,603, WO 2010/066,486, WO 2010/066,631, WO 2010/066,632, WO 2010/063,689, WO 2010/060,821, WO 2010/049,187, WO 2010/031,607, and WO 2010/000,636.

Uses

The present invention is also directed to methods for using the subtilase variants according to the invention or compositions thereof in laundering of textile and fabrics, such as house hold laundry washing and industrial laundry washing.

The invention is also directed to methods for using the variants according to the invention or compositions thereof in cleaning hard surfaces such as floors, tables, walls, roofs etc. as well as surfaces of hard objects such as cars (car wash) and dishes (dish wash).

The subtilase variants of the present invention may be added to and thus become a component of a detergent composition. Thus one aspect of the invention relates to the use of a subtilase variant in a cleaning process such as laundering and/or hard surface cleaning.

A detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising a polypeptide of the present invention as described herein.

The cleaning process or the textile care process may for example be a laundry process, a dishwashing process or cleaning of hard surfaces such as bathroom tiles, floors, table tops, drains, sinks and washbasins. Laundry processes can for example be household laundering, but it may also be industrial laundering. Furthermore, the invention relates to a process for laundering of fabrics and/or garments where the process comprises treating fabrics with a washing solution containing a detergent composition, and at least one protease variant of the invention. The cleaning process or a textile care process can for example be carried out in a machine washing process or in a manual washing process. The washing solution can for example be an aqueous washing solution containing a detergent composition.

The last few years there has been an increasing interest in replacing components in detergents, which is derived from petrochemicals with renewable biological components such as enzymes and polypeptides without compromising the wash performance. When the components of detergent compositions change new enzyme activities or new enzymes having alternative and/or improved properties compared to the common used detergent enzymes such as proteases, lipases and amylases is needed to achieve a similar or improved wash performance when compared to the traditional detergent compositions.

The invention further concerns the use of subtilase variants of the invention in a proteinaceous stain removing processes. The proteinaceous stains may be stains such as food stains, e.g., baby food, sebum, cocoa, egg, blood, milk, ink, grass, ora combination hereof.

Washing Method

The present invention relates to a method of cleaning a fabric, a dishware or hard surface with a detergent composition comprising a protease variant of the invention.

A preferred embodiment concerns a method of cleaning, the method comprising the steps of: contacting an object with a detergent composition comprising a protease variant of the invention under conditions suitable for cleaning the object. In a preferred embodiment the detergent composition is used in a laundry or a dish wash process.

Still another embodiment relates to a method for removing stains from fabric or dishware which comprises contacting the fabric or dishware with a composition comprising a protease of the invention under conditions suitable for cleaning the object.

Also contemplated are compositions and methods of treating fabrics (e.g., to desize a textile) using one or more of the protease of the invention. The protease can be used in any fabric-treating method which is well known in the art (see, e.g., U.S. Pat. No. 6,077,316). For example, in one aspect, the feel and appearance of a fabric is improved by a method comprising contacting the fabric with a protease in a solution. In one aspect, the fabric is treated with the solution under pressure.

The detergent compositions of the present invention are suited for use in laundry and hard surface applications, including dish wash. Accordingly, the present invention includes a method for laundering a fabric or washing dishware. The method comprises the steps of contacting the fabric/dishware to be cleaned with a solution comprising the detergent composition according to the invention. The fabric may comprise any fabric capable of being laundered in normal consumer use conditions. The dishware may comprise any dishware such as crockery, cutlery, ceramics, plastics such as melamine, metals, china, glass and acrylics. The solution preferably has a pH from about 5.5 to about 11.5. The compositions may be employed at concentrations from about 100 ppm, preferably 500 ppm to about 15,000 ppm in solution. The water temperatures typically range from about 5° C. to about 95° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

The enzyme(s) of the detergent composition of the invention may be stabilized using conventional stabilizing agents and protease inhibitors, e.g., a polyol such as propylene glycol or glycerol, a sugar or sugar alcohol, different salts such as NaCl; KCl; lactic acid, formic acid, boric acid, or a boric acid derivative, e.g., an aromatic borate ester, or a phenyl boronic acid derivative such as 4-formylphenyl boronic acid, or a peptide aldehyde such as di-, tri- or tetrapeptide aldehydes or aldehyde analogues (either of the form B1-B0-R wherein, R is H, CH3, CX3, CHX2, or CH2X (X=halogen), B0 is a single amino acid residue (preferably with an optionally substituted aliphatic or aromatic side chain); and B1 consists of one or more amino acid residues (preferably one, two or three), optionally comprising an N-terminal protection group, or as described in WO 2009/

118,375, WO 98/13459) or a protease inhibitor of the protein type such as RASI, BASI, WASI (bifunctional alpha-amylase/subtilisin inhibitors of rice, barley and wheat) or CI2 or SSI. The composition may be formulated as described in, e.g., WO 92/19709, WO 92/19708 and U.S. Pat. No. 6,472,364. In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), Nickel (II), and oxovanadium (IV)).

In some preferred embodiments, the detergent compositions provided herein are typically formulated such that, during use in aqueous cleaning operations, the wash water has a pH of from about 5.0 to about 11.5, or in alternative embodiments, even from about 6.0 to about 10.5. In some preferred embodiments, granular or liquid laundry products are formulated to have a pH from about 6 to about 8. Techniques for controlling pH at recommended usage levels include the use of buffers, alkalis, acids, etc., and are well known to those skilled in the art.

The present invention is further described by the following examples that should not be construed as limiting the scope of the invention.

EXAMPLES

Materials and Methods
Suc-AAPF-pNA Activity Assay

Proteolytic activity can be determined by a method employing Suc-AAPF-PNA as the substrate. Suc-AAPF-PNA is an abbreviation for N-Succinyl-Alanine-Alanine-Proline-Phenylalanine-p-Nitroanilide, and is a blocked peptide which can be cleaved by endo-proteases.

Following cleavage a free PNA molecule is liberated which has a yellow color and thus can be measured by visible spectrophotometry at wavelength 405 nm. The Suc-AAPF-PNA substrate is manufactured by Bachem (cat. no. L1400, dissolved in DMSO).

The protease sample to be analyzed is diluted in residual activity buffer (100 mM Tris pH 8.6). The assay is performed by transferring 30 µl of diluted enzyme samples to 96 well microtiter plate and adding 70 µl substrate working solution (0.72 mg/ml in 100 mM Tris pH8.6). The solution was mixed at room temperature and absorption is measured every 20 seconds over 5 minutes at OD 405 nm.

The slope (absorbance per minute) of the time dependent absorption-curve is directly proportional to the activity of the protease in question under the given set of conditions. The protease sample is diluted to a level where the slope was linear.

Example 1

Preparation and Expression of Subtilisin 309 Variants

The following summarizes the mutation and introduction of an expression cassette into *Bacillus subtilis*. All DNA manipulations were done by PCR (e.g., Sambrook et al.; Molecular Cloning; Cold Spring Harbor Laboratory Press).

Recombinant *B. subtilis* constructs encoding subtilisin 309 variants were used to inoculate shakeflasks containing a rich media (e.g., 100 g/L sucrose (Danisco cat.no. 109-0429), 40 g/L crust soy (soy bean flour), 10 g/L $Na_2HPO_4.12H_2O$ (Merck cat.no. 6579), 0.1 ml/L replace- Dowfax63N10 (Dow). Cultivation typically takes 4 days at 30° C. shaking with 220 rpm.

Example 2

Purification of Subtilisin 309 Variants

The culture broth was centrifuged at 26000 ×g for 20 minutes and the supernatant was carefully decanted from the precipitate. The supernatant was filtered through a Nalgene 0.2 µm filtration unit in order to remove the rest of the *Bacillus* host cells. The pH in the 0.2 µm filtrate was adjusted to pH 8 with 3 M Tris base and the pH adjusted filtrate was applied to a MEP Hypercel column (Pall Corporation) equilibrated in 20 mM Tris/HCl, 1 mM $CaCl_2$, pH 8.0. After washing the column with the equilibration buffer, the column was step-eluted with 20 mM $CH_3COOH$/NaOH, 1 mM $CaCl_2$, pH 4.5. Fractions from the column were analyzed for protease activity using the Suc-AAPF-pNA assay at pH 9 and peak-fractions were pooled. The pH of the pool from the MEP Hypercel column was adjusted to pH 6 with 20% (v/v) $CH_3COOH$ or 3 M Tris base and the pH adjusted pool was diluted with deionized water to the same conductivity as 20 mM MES/NaOH, 2 mM $CaCl_2$, pH 6.0. The diluted pool was applied to a SP-Sepharose® Fast Flow column (GE Healthcare) equilibrated in 20 mM MES/NaOH, 2 mM $CaCl_2$, pH 6.0. After washing the column with the equilibration buffer, the protease variant was eluted with a linear NaCl gradient (0-->0.5 M) in the same buffer over five column volumes. Fractions from the column were analyzed for protease activity using the Suc-AAPF-pNA assay at pH 9 and active fractions were analyzed by SDS-PAGE. Fractions, where only one band was observed on the Coomassie stained SDS-PAGE gel, were pooled as the purified preparation and was used for further experiments.

Example 3

Wash Performance of Subtilisin 309 Variants

The wash performance of subtilisin 309 variants in laundry was assessed using the Automatic Mechanical Stress Assay (AMSA), where the wash performance of many small volume enzyme-detergent solutions can be examined. The AMSA plate has a number of slots for test solutions and a lid that firmly squeezes the textile to be washed against the slot openings. During the wash, the plate, test solutions, textile and lid were vigorously shaken to bring the test solution in contact with the textile and apply mechanical stress in a regular, periodic, oscillating manner. For further description see WO 02/42740 especially the paragraph "Special method embodiments" at pages 23-24.

The laundry experiments were conducted under the experimental conditions specified in Table 2.

TABLE 2

| | |
|---|---|
| Detergent dosage | 2.0 g/L |
| Test solution volume | 160 µL (20 µL enzyme + 140 µL detergent) |
| pH | 8.4 |
| Wash time | 20 minutes |
| Temperature | 20° C. |
| Water hardness | 12°dH |

Model detergent and test materials were as described in Table 3:

TABLE 3

Composition of model detergents and test materials

| | |
|---|---|
| Blue moon Lavender | Commercially available |
| Test material | C-05 (Blood/milk/ink on cotton) |
| | PC-03 (Chocolate milk with carbon black on Polyester/cotton, 65/35) |

Test materials were obtained from Center For Testmaterials BV, 3133 KT Vlaardingen, the Netherlands.

Water hardness was adjusted to 12° dH by addition of $CaCl_2$, $MgCl_2$, and $NaHCO_3$ ($Ca^{2+}:Mg^{2+}=2:1:4.5$) to the test system. After washing, the textiles were flushed in tap water and dried.

The wash performance was measured as the brightness of the color of the textile washed. Brightness can also be expressed as the intensity of the light reflected from the sample when illuminated with white light. When the sample is stained the intensity of the reflected light is lower than that of a clean sample. Therefore the intensity of the reflected light can be used to measure wash performance.

Color measurements were made with a Kodak iQsmart flatbed scanner (Kodak, Midtager 29, DK-2605 Brøndby, Denmark), which is used to capture an image of the washed textile.

To extract a value for the light intensity from the scanned images, 24-bit pixel values from the image were converted into values for red, green and blue (RGB). The intensity value (Int) was calculated by adding the RGB values together as vectors and then taking the length of the resulting vector:

$$Int = \sqrt{r^2 + g^2 + b^2}.$$

The results are shown in Table 4. The results are given as relative performance compared to subtilisin 309 (SEQ ID NO: 1) and an average of two enzyme concentrations 30 and 60 nM of two different swatches. A RP value of below 0.8 is considered worse, 0.8-1.2 is considered on par, 1.2 or above is considered better than subtilisin 309 (SEQ ID NO: 1).

TABLE 4

AMSA relative performance of variants compared to subtilisin 309.

| Mutations | RP on C-05 | RP on PC-03 | RP average |
|---|---|---|---|
| S9E + N43R + G61E + N76D + Q206L + L262E | 1.09 | 1.19 | 1.14 |
| S9E + N43R + I72A + N76D + G115W + H120V + P129D + A158E + G160P + Q182E + N185E + S188E + Q191N + A194P + N204D + V205I + Q206L + Y209W + S212G + S216V + T255E + S256D + S259D + T260E + N261W + L262E | 1.10 | 1.17 | 1.14 |
| S9E + N43R + N76D + G115W + H120V + P129D + A194P + Q206L + Y209W + S259D + L262E | 1.06 | 1.06 | 1.06 |
| S9E + N43R + N76D + G115W + H120V + A194P + Q206L + Y209W + S259D + L262E | 1.02 | 1.01 | 1.01 |
| S9E + N43R + N76D + G115W + A194P + Q206L + Y209W + S259D + L262E | 0.99 | 1.01 | 1.00 |
| S9E + N43R + N76D + Q137H + S141H + R145H + A194P + N204D + V205I + Q206L + Y209W + S212G + S216V + L262E | 1.05 | 1.03 | 1.04 |
| S9E + N43R + N76D + Q191N + A194P + Q206L + Y209W + S259D + L262E | 1.01 | 0.92 | 0.96 |
| S9E + N43R + N76D + A194P + N204D + V205I + Q206L + Y209W + S212G + S216V + S256D + S259D + T260E + N261W + L262E | 1.42 | 1.44 | 1.43 |
| S9E + N43R + N76D + A194P + N204D + V205I + Q206L + Y209W + S212G + S216V + S256D + S259D + N261W + L262E | 1.01 | 0.88 | 0.94 |
| S9E + N43R + N76D + A194P + N204D + V205I + Q206L + Y209W + S212G + S216V + N261W + L262E | 1.09 | 0.79 | 0.94 |
| S9E + N43R + N76D + A194P + N204D + V205I + Q206L + Y209W + S212G + S216V + L262E | 1.02 | 0.92 | 0.97 |
| S9E + N43R + N76D + A194P + V205I + Q206L + Y209W + S212G + S216V + L262E | 1.02 | 0.98 | 1.00 |
| S9E + N43R + N76D + A194P + Q206L + Y209W + S212G + S216V + L262E | 0.82 | 0.84 | 0.83 |
| S9E + N43R + N76D + A194P + Q206L + Y209W + S212G + S259D + L262E | 1.08 | 0.86 | 0.97 |
| S9E + N43R + N76D + A194P + Q206L + Y209W + S212G + L262E | 0.87 | 0.98 | 0.92 |
| S9E + N43R + N76D + A194P + Q206L + Y209W + T255E + S256D + S259D + T260E + N261W + L262E | 1.18 | 1.19 | 1.19 |
| S9E + N43R + N76D + A194P + Q206L + Y209W + S256D + S259D + N261W + L262E | 1.26 | 1.26 | 1.26 |
| S9E + N43R + N76D + A194P + Q206L + Y209W + S259D + N261W + L262E | 1.00 | 0.91 | 0.96 |
| S9E + N43R + N76D + A194P + Q206L + Y209W + S259D + L262E | 1.12 | 1.14 | 1.13 |
| S9E + N43R + N76D + A194P + Q206L + Y209W + S259D + L262E + *275aH + *275bH | 1.15 | 1.05 | 1.10 |
| S9E + N43R + N76D + A194P + Q206L + Y209W + T255E + S256D + S259D + T260E + N261W + L262E | 1.18 | 1.19 | 1.19 |
| S9E + N43R + N76D + A194P + Q206L + Y209W + S256D + S259D + N261W + L262E | 1.26 | 1.26 | 1.26 |
| S9E + N43R + N76D + Q182E + N185E + S188E + Q191N + A194P + Q206L + Y209W + S259D + L262E | 0.96 | 0.95 | 0.95 |
| S9E + N43R + N76D + A194P + Q206L + Y209W + L262E | 1.18 | 1.14 | 1.16 |
| S9E + N43R + N76D + A194P + Q206L + S259D + L262E | 1.03 | 0.92 | 0.98 |
| S9E + N43R + N76D + A194P + Q206L + L262E | 1.00 | 1.05 | 1.02 |
| S9E + G61E + N76D + Q206L + L262E | 1.17 | 1.29 | 1.23 |

TABLE 4-continued

AMSA relative performance of variants compared to subtilisin 309.

| Mutations | RP on C-05 | RP on PC-03 | RP average |
|---|---|---|---|
| S9E + G61E + N76D + L262E | 1.10 | 0.87 | 0.98 |
| S9E + N76D + Q206L + Y209W + L262E | 1.04 | 1.36 | 1.20 |
| S9E + N76D + Q206L + L262E | 1.14 | 1.29 | 1.21 |
| S9E + N76D + L262E | 0.99 | 0.89 | 0.94 |

Example 4

Accelerated Storage Stability Assay

Storage stability of protease variants in liquid detergent was evaluated using an accelerated assay with incubation at 60° C. for up to 48 hours.

Culture supernatants containing 25-75 µg/ml active protease were diluted 1, 2, 4 and 8 times using 0.01% Triton X-100. For each variant 2 wells with each dilution were included. 30 µl diluted protease sample was mixed with 270 µl Model O detergent in the well of a microtiter plate (Nunc U96 PP 0.5 ml) using a magnetic bar (on Zephyr pipetting station (Caliper LifeSciences) for 30 min). 20 µl of this mixture was then transferred to another microtiter plate (Nunc U96 PP 0.5 ml with added magnetic bars) and mixed with 80 µl 100 mM Tris pH 8.6 (at least 5 min on Zephyr). 30 µl of this dilution was transferred to a Nunc F 96-MTP, and after addition of 70 µl substrate solution initial activity of unstressed sample was determined by measuring absorbance at 405 nm every 20 sec for 5 min (on a SpectraMax Plus). After sealing, the detergent plate was incubated at 60° C. in an Eppendorf Thermomixer (no shaking). After 1, 4, 23 and 47 hours incubation, 20 µl samples were withdrawn and residual activity of stressed sample was measured as with the initial, unstressed activity.

Decrease in activity during incubation with detergent was assumed to be exponential. Half-lifes (T½) were found from linear regression of Log(Activity) versus incubation time (0, 1, 4, 23 and 47 hours), and half-life improvement factors (T½ IF) were calculated as half-life of protease variant relative to the half-life of SEQ ID NO: 1. This means that T½ for Savinase (Subtilisin 309) is 1.

TABLE 5

| Composition of Detergent | | |
|---|---|---|
| Model O | LAS, (C10-C13) alkylbenzene-sulfonic acid | 3.8% |
| | AES, AEOS, sodium lauryl ether sulfate | 8% |
| | AEO, Alcohol ethoxylate | 4% |
| | Soap, lauric acid | 1.0% |
| | Trisodium citrate dihydrate | 2% |
| | Sodium hydroxide | 0.6% |
| | CaCl$_2$, 2H$_2$O | 0.02% |
| | Kathon, preservative | 0.1% |
| | Triethanolamine | 0.4% |
| | Deionized Water to 100% | |
| | (amounts in percent weight (wt)) | |

TABLE 6

Accelerated storage stability results in model O. T½ IF: Half life improvement factors relative to Subtilisin 309 or Subtilisin 309 + N76D reference

| Mutations | T½IF relative to Savinase + N76D | T½ IF relative to Savinase |
|---|---|---|
| Subtilisin 309 | 0.23 ± 0.01 | 1 ± 0.06 |
| Subtilisin 309 + N76D | 1.0 ± 0.1 | 4.4 ± 0.6 |
| S9E | 0.8 ± 0.1 | 3.4 ± 0.6 |
| S9E + N43R + N76D + G115W + H120V + P129D + A194P + Q206L + Y209W + S259D + L262E | 290 ± 160 | 1300 ± 700 |
| S9E + N43R + N76D + A194P + N204D + V205I + Q206L + Y209W + S212G + S216V + L262E | 230 ± 100 | 1000 ± 400 |
| S9E + N43R + N76D + A194P + Q206L + Y209W + S259D + L262E | 210 ± 110 | 900 ± 500 |
| S9E + N43R + N76D + A194P + Q206L + Y209W + S212G + S259D + L262E | 240 ± 110 | 850 ± 390 |
| S9E + N43R + N76D + A194P + Q206L + Y209W + S259D + N261W + L262E | 230 ± 110 | 825 ± 370 |
| S9E + N43R + N76D + A194P + Q206L + Y209W + S212G + S216V + L262E | 220 ± 180 | 760 ± 620 |
| S9E + N43R + N76D + A194P + Q206L + Y209W + S212G + L262E | 225 ± 120 | 785 ± 415 |
| S9E + N43R + N76D + *99aE + P131* + A194P + Q206L + Y209W + S259D + L262E | 730 ± 400 | 2550 ± 1400 |
| S9E + N43R + N76D + P131* + A194P + Q206L + Y209W + S259D + L262E | 380 ± 145 | 1320 ± 500 |
| S9E + N43R + N76D + A194P + Q206L + Y209W + L262E | 180 ± 110 | 620 ± 375 |
| S9E + N43R + N76D + A194P + Q206L + S259D + L262E | 110 ± 20 | 380 ± 70 |
| S9E + N43R + G61E + N76D + Q206L + L262E | 80 ± 15 | 290 ± 55 |
| S9E + N43R + N76D + A194P + Q206L + L262E | 110 ± 20 | 390 ± 70 |
| S9E + G61E + N76D + Q206L + L262E | 50 ± 20 | 220 ± 80 |

TABLE 6-continued

Accelerated storage stability results in model O. T½ IF: Half life improvement factors relative to Subtilisin 309 or Subtilisin 309 + N76D reference

| Mutations | T½IF relative to Savinase + N76D | T½ IF relative to Savinase |
|---|---|---|
| S9E + N76D + L262E | 19 ± 4 | 84 ± 15 |
| N76D + L262E | 10 ± 2 | 44 ± 9 |
| L262E | 1.1 ± 0.1 | 4.7 ± 0.6 |

Example 5

Accelerated Storage Stability Assay

Storage stability of protease variants in liquid detergent was evaluated using an accelerated assay with incubation at 60° C. for up to 48 hours in the CNS (Chinese national standard) detergent. Otherwise the experiment was carried out under the same conditions as in Example 4.

TABLE 7

| | Composition of Detergent | |
|---|---|---|
| CNS pH 8 | LAS, (C10-C13) alkylbenzene-sulfonic acid | 8% |
| | AES, AEOS, sodium lauryl ether sulfate | 4% |
| | AEO9, Alcohol ethoxylate | 4% |

TABLE 7-continued

| Composition of Detergent | |
|---|---|
| TEA (Triethanolamine) | 0.5% |
| NaCitrate | 0.5% |
| Sodium hydroxide | 1% |
| CaCl2, 2H$_2$O | 0.01% |
| Deionized Water to 100% | |
| (amounts in percent weight (wt)) | |

In this experiment the stability is tested in CNS (Chinese National Standard) and the results in Table 8 are expressed as T½ IF: Half-life improvement factors relative to Subtilisin 309 or Subtilisin 309+N76D as described in Example 4.

1: T½ IF>1000;
2: 500≤T½IF≤1000;
3: 50≤T½IF<500.

TABLE 8

Accelerated storage stability results in CNS Column A = T½ IF relative to Subtilisin 309 + N76D, Column B = T½ IF relative to Subtilisin 309.

| Mutations | A | B |
|---|---|---|
| S9E + N43R + N76D + A158E + G160P + S161E + A194P + N204D + V205I + Q206L + Y209W + S212G + S216V + L262E | 1 | 1 |
| S9E + N43R + A48H + N76D + N117H + A158E + G160P + S161E + A194P + N204D + V205I + Q206L + Y209W + S212G + S216V + N238H + L262E | 2 | 1 |
| S9E + N43R + A48H + N76D + N117H + G160D + S161E + A194P + N204D + V205I + Q206L + Y209W + S212G + S216V + N238H + L262E | 2 | 1 |
| S9E + N43R + N76D + A158E + G160P + S161E + A194P + N204D + V205I + Q206L + Y209W + S212G + S216V + L262E + *275aH + *275bH | 1 | 1 |
| S9E + N43R + N76D + G160D + S161E + A194P + N204D + V205I + Q206L + Y209W + S212G + S216V + L262E + *275aH + *275bH | 1 | 1 |
| S9E + G20H + T22H + S24H + N43R + N76D + G160D + S161E + A194P + N204D + V205I + Q206L + Y209W + S212G + S216V + L262E | 3 | 2 |
| S9E + N43R + N76D + N117H + H120D + A158E + G160P + S161E + A194P + N204D + V205I + Q206L + Y209W + S212G + S216V + L262E | 1 | 1 |
| S9E + N43R + N76D + N117H + H120D + G160D + S161E + A194P + N204D + V205I + Q206L + Y209W + S212G + S216V + L262E | 1 | 1 |
| S9E + N43R + N76D + N117H + H120D + G160D + S161E + S163G + A194P + N204D + V205I + Q206L + Y209W + S212G + S216V + L262E | 1 | 1 |
| S9E + N43R + N76D + N117H + H120D + G160D + S161E + A194P + N204D + V205I + Q206L + Y209W + S212G + S216V + L262E + *275aH + *275bH | 1 | 1 |
| S9E + N43R + N76D + N117H + H120D + G160D + S161E + S163G + A194P + N204D + V205I + Q206L + Y209W + S212G + S216V + L262E + *275aH + *275bH | 2 | 1 |
| S9E + N43R + N76D + N117H + H120D + A158E + G160P + S161E + A194P + N204D + V205I + Q206L + Y209W + S212G + S216V + L262E + *275aR | 1 | 1 |
| S9E + N43R + N76D + A194P + N204D + V205I + Q206L + Y209W + S212G + S216V + S256D + L262E | 1 | 1 |
| S9E + N43R + N76D + A194P + N204D + V205I + Q206L + Y209W + S212G + S216V + T260A + L262E | 1 | 1 |
| S9E + N43R + N76D + N117H + H120D + A194P + N204D + V205I + Q206L + Y209W + S212G + S216V + S256D + T260A + L262E | 1 | 1 |
| S9E + N43R + N76D + P129D + A194P + N204D + V205I + Q206L + Y209W + S212G + S216V + S256D + T260A + L262E | 1 | 1 |
| S9E + N43R + N76D + A194P + G195E + N204D + V205I + Q206L + Y209W + S212G + S216V + S256D + L262E | 2 | 1 |

TABLE 8-continued

Accelerated storage stability results in CNS Column A = T½ IF relative to Subtilisin 309 + N76D, Column B = T½ IF relative to Subtilisin 309.

| Mutations | A | B |
|---|---|---|
| S9E + N43R + N76D + A194P + G195E + N204D + V205I + Q206L + Y209W + S212G + S216V + T260A + L262E | 1 | 1 |
| S9E + N43R + N76D + A194P + N204D + V205I + Q206L + Y209W + S212G + S216V + S256D + T260A + L262E + *275aH + *275bH | 1 | 1 |
| S9E + N43R + N76D + N117H + H120D + A194P + N204D + V205I + Q206L + Y209W + S212G + S216V + L262E | 1 | 1 |
| S9E + N43R + A48H + N76D + N117H + A194P + G195E + N204D + V205I + Q206L + Y209W + S212G + S216V + N238H + L262E + *275aR | 2 | 1 |
| S9E + N43R + N76D + N117H + H120D + A194P + N204D + V205I + Q206L + Y209W + S212G + S216V + L262E + *275aH + *275bH | 1 | 1 |
| S9E + N43R + N76D + Y91H + N117H + A194P + G195E + N204D + V205I + Q206L + Y209W + S212G + S216V + N238H + L262E | 3 | 1 |
| S9E + N43R + A48H + N76D + N117H + A194P + G195E + N204D + V205I + Q206L + Y209W + S212G + S216V + N238H + L262E | 1 | 1 |
| S9E + G61E + N76D + Q206L + L262E | 3 | 3 |
| S9E + N43R + N76D + A194P + Q206L + Y209W + S259D + L262E | 3 | 1 |
| S9E + N43R + N76D + G115W + A194P + Q206L + Y209W + S259D + L262E | 3 | 1 |
| S9E + N43R + N76D + G115W + H120V + A194P + Q206L + Y209W + S259D + L262E | 2 | 1 |
| S9E + N43R + N76D + Q191N + A194P + Q206L + Y209W + S259D + L262E | 3 | 2 |
| S9E + N43R + N76D + A194P + V205I + Q206L + Y209W + S212G + S216V + L262E | 1 | 1 |
| S9E + N43R + N76D + A194P + N204D + V205I + Q206L + Y209W + S212G + S216V + L262E | 2 | 1 |
| S9E + N43R + N76D + A194P + Q206L + Y209W + T255E + S256D + S259D + T260E + N261W + L262E | 3 | 1 |
| S9E + N43R + N76D + G115W + H120V + P129D + A194P + Q206L + Y209W + S259D + L262E | 2 | 1 |
| S9E + N43R + N76D + Q182E + N185E + S188E + Q191N + A194P + Q206L + Y209W + S259D + L262E | 2 | 1 |
| S9E + N43R + N76D + A194P + Q206L + Y209W + S256D + S259D + N261W + L262E | 2 | 1 |
| S9E + N76D + Q206L + L262E | 3 | 3 |
| S9E + N76D + Q206L + Y209W + L262E | 3 | 2 |
| S9E + N43R + I72A + N76D + G115W + H120V + P129D + A158E + G160P + Q182E + N185E + S188E + Q191N + A194P + N204D + V205I + Q206L + Y209W + S212G + S216V + T255E + S256D + S259D + T260E + N261W + L262E | 3 | 2 |
| S9E + N76D + Q206L + Y209W + N261W + L262E | 3 | 2 |
| S9E + N43R + N76D + A194P + N204D + V205I + Q206L + Y209W + S212G + S216V + N261W + L262E | 1 | 1 |
| S9E + N43R + N76D + A194P + N204D + V205I + Q206L + Y209W + S212G + S216V + S259D + N261W + L262E | 1 | 1 |
| S9E + N43R + N76D + A194P + N204D + V205I + Q206L + Y209W + S212G + S216V + S256D + S259D + N261W + L262E | 1 | 1 |
| S9E + G61E + N76D + Q137H + S141H + R145H + Q206L + L262E | 3 | 3 |
| S9E + G61E + N76D + Q206L + L262E + *275aH + *275bH | 3 | 3 |
| S9E + N43R + N76D + Q137H + S141H + R145H + A194P + Q206L + Y209W + S259D + L262E | 3 | 2 |
| S9E + N43R + N76D + A194P + Q206L + Y209W + S259D + L262E + *275aH + *275bH | 3 | 2 |
| S9E + N43R + N76D + Q137H + S141H + R145H + A194P + N204D + V205I + Q206L + Y209W + S212G + S216V + L262E | 1 | 1 |
| S9E + N43R + N76D + A194P + N204D + V205I + Q206L + Y209W + S212G + S216V + T255E + S256D + S259D + N261W + L262E | 1 | 1 |
| S9E + N43R + N76D + A194P + N204D + V205I + Q206L + Y209W + S212G + S216V + S256D + T260E + S259D + N261W + L262E | 1 | 1 |
| S9E + N43R + N76D + G160D + S161E + A194P + N204D + V205I + Q206L + Y209W + S212G + S216V + L262E | 1 | 1 |
| S9E + N43R + N76D + G160D + S161E + S163G + A194P + N204D + V205I + Q206L + Y209W + S212G + S216V + L262E | 1 | 1 |
| S9E + N43R + N76D + Q137H + S141H + R145H + A158E + G160P + S161E + A194P + N204D + V205I + Q206L + Y209W + S212G + S216V + L262E | 1 | 1 |
| S9E + N43R + N76D + Q137H + S141H + R145H + G160D + S161E + A194P + N204D + V205I + Q206L + Y209W + S212G + S216V + L262E | 1 | 1 |
| S9E + N43R + N76D + N117H + H120D + A158E + G160P + S161E + A194P + N204D + V205I + Q206L + Y209W + S212G + S216V + L262E + *275aH + *275bH | 1 | 1 |
| S9E + N43R + A48H + N76D + N117H + H120D + A158E + G160P + S161E + A194P + N204D + V205I + Q206L + Y209W + S212G + S216V + N238H + L262E + *275aR | 2 | 1 |
| S9E + N43R + N76D + N117H + H120D + A194P + N204D + V205I + Q206L + Y209W + S212G + S216V + S256D + L262E | 1 | 1 |
| S9E + N43R + N76D + N117H + H120D + A194P + N204D + V205I + Q206L + Y209W + S212G + S216V + T260A + L262E | 2 | 1 |
| S9E + N43R + N76D + A194P + G195E + N204D + V205I + Q206L + Y209W + S212G + S216V + S256D + T260A + L262E | 1 | 1 |

TABLE 8-continued

Accelerated storage stability results in CNS Column A = T½ IF relative to Subtilisin 309 + N76D, Column B = T½ IF relative to Subtilisin 309.

| Mutations | A | B |
|---|---|---|
| S9E + N43R + N76D + A194P + N204D + V205I + Q206L + Y209W + S212G + S216V + S256D + T260A + L262E + *275aR | 2 | 1 |
| S9E + N43R + A48H + N76D + N117H + A194P + N204D + V205I + Q206L + Y209W + S212G + S216V + N238H + S256D + T260A + L262E | 2 | 1 |
| S9E + N43R + A48H + N76D + N117H + P129D + A194P + N204D + V205I + Q206L + Y209W + S212G + S216V + N238H + S256D + T260A + L262E | 1 | 1 |
| S9E + N43R + N76D + P129D + A194P + N204D + V205I + Q206L + Y209W + S212G + S216V + S256D + T260A + L262E + *275aH + *275bH | 1 | 1 |
| S9E + N43R + N76D + A194P + G195E + N204D + V205I + Q206L + Y209W + S212G + S216V + L262E | 1 | 1 |
| S9E + N43R + N76D + A194P + G195E + N204D + V205I + Q206L + Y209W + S212G + S216V + L262E + *275aH + *275bH | 1 | 1 |
| S9E + N43R + N76D + G160D + S161E + A194P + Q206L + Y209W + S259D + L262E | 3 | 1 |
| S9E + N43R + A48H + N76D + N117H + A158E + G160P + S161E + A194P + Q206L + Y209W + N238H + S259D + L262E | 3 | 1 |
| S9E + N43R + A48H + N76D + N117H + G160D + S161E + A194P + Q206L + Y209W + N238H + S259D + L262E | 3 | 1 |
| S9E + N43R + N76D + A158E + G160P + S161E + A194P + Q206L + Y209W + S259D + L262E + *275bH + *275aH | 3 | 1 |
| S9E + N43R + N76D + G160D + S161E + A194P + Q206L + Y209W + S259D + L262E + *275aH + *275bH | 2 | 1 |
| S9E + N43R + N76D + N117H + H120D + A158E + G160P + S161E + A194P + Q206L + Y209W + S259D + L262E | 3 | 1 |
| S9E + N43R + N76D + N117H + H120D + G160D + S161E + A194P + Q206L + Y209W + S259D + L262E | 2 | 1 |
| S9E + N43R + N76D + N117H + H120D + A158E + G160P + S161E + A194P + Q206L + Y209W + N238H + S259D + L262E + *275aH + *275bH | 2 | 1 |
| S9E + N43R + N76D + N117H + H120D + G160D + S161E + A194P + Q206L + Y209W + S259D + L262E + *275aH + *275bH | 3 | 1 |
| S9E + N43R + A48H + N76D + N117H + H120D + A158E + G160P + S161E + A194P + Q206L + Y209W + N238H + S259D + L262E + *275aR | 3 | 2 |
| S9E + N43R + N76D + A194P + G195E + Q206L + Y209W + S259D + L262E + *275aR | 3 | 2 |
| S9E + N43R + N76D + N117H + H120D + A194P + Q206L + Y209W + S259D + L262E | 3 | 1 |
| S9E + N43R + N76D + P129D + A194P + Q206L + Y209W + S259D + L262E | 3 | 1 |
| S9E + N43R + N76D + P129D + A194P + G195E + Q206L + Y209W + S259D + L262E | 2 | 1 |
| S9E + N43R + N76D + N117H + H120D + A194P + Q206L + Y209W + S259D + L262E + *275aH + *275bH | 3 | 2 |
| S9E + N43R + N76D + A194P + Q206L + Y209W + S259D + T260A + L262E | 3 | 1 |
| S9E + N43R + N76D + N117H + H120D + A194P + Q206L + Y209W + S259D + T260A + L262E + *275aR | 3 | 2 |
| S9E + N43R + A48H + N76D + N117H + A194P + Q206L + Y209W + N238H + S259D + T260A + L262E | 2 | 1 |
| S9E + G61E + N76D + Q206L + Y209W + S256D + L262E | 3 | 2 |
| S9E + G61E + N76D + A158E + G160P + S161E + Q206L + L262E | 3 | 3 |
| S9E + G61E + N76D + Q137H + S141H + R145H + A158E + G160P + S161E + Q206L + L262E | 3 | 2 |
| S9E + G61E + N76D + A158E + G160P + S161E + Q206L + L262E + *275aH + *275bH | 3 | 3 |
| S9E + G61E + N76D + N117H + H120D + G160D + S161E + S163G + Q206L + L262E + *275aH + *275bH | 3 | 3 |
| S9E + G61E + N76D + Q206L + S256D + L262E | 3 | 3 |
| S9E + G61E + N76D + P129D + Q206L + T260A + L262E | 3 | 3 |
| S9E + G61E + N76D + P129D + Q206L + S256D + T260A + L262E + *275aH + *275bH | 3 | 3 |
| S9E + G61E + N76D + N204D + Q206L + Y209W + L262E | 3 | 1 |
| S9E + G61E + N76D + Q137H + S141H + R145H + N204D + Q206L + Y209W + L262E + *275aR | 3 | 2 |
| S9E + G61E + N76D + P129D + Q206L + L262E + *275aH + *275bH | 3 | 3 |
| S9E + G61E + N76D + N204D + Q206L + Y209W + L262E + *275aH + *275bH | 3 | 1 |

Example 6

AMSA Wash Performance of Subtilisin 309 Variants Sp.

The wash performance of subtilisin 309 variants was tested using laundry liquid detergent on three different technical stains using the Automatic Mechanical Stress Assay (AMSA).

By AMSA the wash performance in laundry of many small volume enzyme-detergent solutions can be examined. The AMSA plate has a number of slots for test solutions and a lid that firmly squeezes the textile to be washed against the slot openings. During the wash, the plate, test solutions, textile and lid are vigorously shaken to bring the test solution in contact with the textile and apply mechanical stress in a regular, periodic, oscillating manner. For further description, see WO02/42740 especially the paragraph "Special method embodiments" on page 23-24.

TABLE 9

| Model detergents and test materials were as follows: | |
| --- | --- |
| Blue Moon Deep Clean | Commercially available detergent |
| Test material | C-05 Blood/milk/ink on cotton<br>PC-03 Chocolate milk/soot<br>EMPA117 EH Blood/milk/ink on cotton/polyester extra heated |

Test materials were obtained from EMPA Testmaterials AG, Movenstrasse 12, CH-9015 St. Gallen, Switzerland and from Center For Testmaterials BV, P.O. Box 120, 3133 KT Vlaardingen, the Netherlands.

The wash performance was measured as the brightness of the color of the textile washed. Brightness may also be expressed as the intensity of the light reflected from the sample when illuminated with white light. When the sample is stained the intensity of the reflected light is lower, than that of a clean sample. Therefore the intensity of the reflected light can be used to measure wash performance.

Color measurements were made with a professional flat-bed scanner (Kodak iQsmart, Kodak, Midtager 29, DK-2605 Brøndby, Denmark), which was used to capture an image of the washed textile.

To extract a value for the light intensity from the scanned images, 24-bit pixel values from the image were converted into values for red, green and blue (RGB). The intensity value (Int) was calculated by adding the RGB values together as vectors and then taking the length of the resulting vector:

$$Int = \sqrt{r^2 + g^2 + b^2}.$$

The experiments were conducted using a single cycle wash procedure, with the detergent composition and swatches described in table 10 and the experimental conditions as specified in Table 10 below.

TABLE 10

| Experimental conditions for laundry experiments | |
| --- | --- |
| Detergent dosage | Blue Moon Deep Clean 2 g/L |
| Test solution volume | 160 micro L |
| pH | As is |
| Wash time | 20 minutes |
| Temperature | 20° C. |
| Water hardness | 12° dH |
| Protease concentration | 30 or 60 nM |
| Swatch | C-05 Blood/milk/ink on cotton<br>PC-03 Chocolate milk/soot<br>EMPA11 EH Blood/milk/ink on cotton/polyester extra heated |

Water hardness was adjusted to 12° dH by addition of $CaCl_2$, $MgCl_2$, and $NaHCO_3$ ($Ca^{2+}:Mg^{2+}:CO_3^{-}=2:1:4.5$) to the test system. After washing the textiles were rinsed in tap water and dried.

TABLE 11

Relative performance of subtilisin 309 variants compared to detergent with Subtilisin 309 (SEQ ID NO 1) at 20° C.

| | PC-03 | | C-05 | |
| --- | --- | --- | --- | --- |
| Protease concentration | 30 nM | 60 nM | 30 nM | 60 nM |
| Subtilsin309 (SEQ ID NO 1) | 1 | 1 | 1 | 1 |
| S9E + N43R + N76D + S188E + A194P + V205I + Q206L + Y209W + S216V + L262E + *275aH + *275bH | 1.1 | 1.2 | 0.9 | 1 |
| S9E + N43R + N76D + A158E + A194P + N204D + V205I + Q206L + Y209W + S212G + S216V + L262E | 1.2 | 1 | 0.9 | 0.9 |
| S9E + N43R + N76D + A158E + A194P + N204D + V205I + Q206L + Y209W + S212G + S216V + L262E + *275aH + *275bH | 1.1 | 1.1 | 1.1 | 1.2 |
| S9E + N43R + N76D + A158E + G160P + V205I + Q206L + Y209W + S259D + N261W + L262E | 1.5 | 1.7 | 1.3 | 1.2 |
| S9E + N43R + N76D + A158E + G160P + A194P + N204D + V205I + Q206L + Y209W + S212G + S216V + L262E | 1.2 | 1.1 | 0.9 | 1 |
| S9E + N43R + N76D + A158E + A194P + V205I + Q206L + Y209W + S259D + N261W + L262E | 1 | 1.2 | 1.1 | 0.9 |
| S9E + N43R + N76D + A158E + G160P + S161E + A194P + N204D + V205I + Q206L + Y209W + L262E + *275aH + *275bH | 1.4 | 1.5 | 1 | 0.9 |
| S9E + N43R + N76D + A158E + G160P + S161E + A194P + V205I + Q206L + Y209W + S212G + S216V + L262E | 1.3 | 1.2 | 1 | 1 |
| S9E + N43R + N76D + A158E + G160P + S161E + A194P + V205I + Q206L + Y209W + S212G + S216V + L262E + *275aH + *275bH | 1.2 | 1.2 | 0.9 | 1.1 |
| S9E + N43R + N76D + A158E + S161E + A194P + N204D + V205I + Q206L + Y209W + S212G + S216V + L262E + *275aH + *275bH | 1 | 1 | 0.8 | 1 |
| S9E + N43R + N76D + G160P + V205I + Q206L + Y209W + S259D + N261W + L262E | 1.5 | 1.6 | 1.3 | 1.1 |
| S9E + N43R + N76D + A194P + V205I + Q206L + Y209W + S216V + L262E | 0.9 | 1 | 0.8 | 0.9 |
| S9E + N43R + N76D + V205I + Q206L + Y209W + S259D + N261W + L262E | 1.1 | 1.2 | 1 | 1 |

TABLE 11-continued

Relative performance of subtilisin 309 variants compared to detergent with Subtilisin 309 (SEQ ID NO 1) at 20° C.

| Protease concentration | PC-03 | | C-05 | |
|---|---|---|---|---|
| | 30 nM | 60 nM | 30 nM | 60 nM |
| S9E + N43R + N76D + G160P + A194P + N204D + V205I + Q206L + Y209W + S212G + S216V + L262E | 0.8 | 1 | 1.1 | 1 |
| S9E + N43R + N76D + G160P + A194P + N204D + V205I + Q206L + Y209W + S212G + S216V + L262E + *275aH + *275bH | 1.2 | 1.1 | 0.8 | 1.1 |
| S9E + N43R + N76D + G160P + S161E + A194P + N204D + V205I + Q206L + Y209W + S212G + S216V + L262E | 1 | 0.8 | 0.9 | 1 |
| S9E + N43R + N76D + G160P + S161E + A194P + N204D + V205I + Q206L + Y209W + S212G + S216V + L262E + *275aH + *275bH | 1.1 | 1 | 1.1 | 1.1 |
| S9E + N43R + N76D + N204D + V205I + Q206L + Y209W + S259D + N261W + L262E | 1.3 | 1.6 | 1.2 | 1.2 |
| S9E + N43R + N76D + G160P + S161E + V205I + Q206L + Y209W + S259D + N261W + L262E | 1.6 | 1.6 | 1.4 | 1.2 |
| S3V + N76D + H120V + Q182E + N185E + S188E + V205I + Q206L + Y209W + S216V + S256D + N261W + L262E | 1.1 | 1.2 | 0.9 | 0.9 |
| S9E + N43R + N76D + H120V + Q182E + A194P + V205I + Q206L + Y209W + S256D + N261W + L262E + *275aH + *275bH | 0.9 | 1 | 0.9 | 0.9 |
| S9E + N43R + N76D + N117H + A194P + Q206L + Y209W + N238H + S259D + T260A + L262E | 0.9 | 1 | 0.9 | 0.9 |
| S9E + N43R + N76D + N185E + S188E + A194P + Q206L + Y209W + S259D + L262E | 1 | 1.1 | 0.9 | 1 |
| S9E + N43R + N76D + V205I + Q206L + Y209W + S216V + S259D + N261W + L262E | 1.6 | 1.6 | 1.5 | 1.2 |
| S9E + N43R + N76D + S161E + V205I + Q206L + Y209W + S259D + N261W + L262E | 1.3 | 1.4 | 1.1 | 1 |
| S9E + N43R + N76D + Q182E + A194P + V205I + Q206L + Y209W + S259D + N261W + L262E | 1 | 1.1 | 0.9 | 1 |
| S9E + N43R + N76D + S161E + A194P + N204D + V205I + Q206L + Y209W + S212G + S216V + L262E | 1.3 | 0.9 | 1 | 0.9 |
| S9E + N43R + N76D + S161E + A194P + N204D + V205I + Q206L + Y209W + S212G + S216V + L262E + *275aH + *275bH | 1.2 | 1 | 0.9 | 1.1 |
| S9E + N43R + N76D + V205I + Q206L + Y209W + S212G + S259D + N261W + L262E | 1.6 | 1.6 | 1.4 | 1.3 |
| S9E + N43R + N76D + S188E + A194P + V205I + Q206L + Y209W + S216V + L262E | 1 | 1 | 0.9 | 0.9 |
| S9E + N76D + Q182E + V205I + Q206L + Y209W + S256D + N261W + L262E | 0.8 | 1 | 0.9 | 0.9 |
| S9E + N43R + N76D + S78H + A194P + V205I + Q206L + Y209W + S216V + L262E | 0.9 | 0.9 | 0.9 | 0.9 |
| S9E + N43R + N76D + N204D + V205I + Q206L + Y209W + S212G + S216V + S259D + N261W + L262E | 1.7 | 1.7 | 1.6 | 1.2 |
| S9E + N76D + V205I + Q206L + Y209W + N261W + L262E | 0.9 | 1.1 | 1 | 1 |

The results of Table 11 show that the Subtilisin 309 variants have improved or on par performance wash performance compared to Subtilisin 309 on chocolate/milk (PC-03, C-03) at 20° C.

TABLE 12

Relative performance of proteases from *Bacillus* sp. subtilisin 309 variants compared to detergent with Subtilisin 309 (SEQ ID NO 1) at 20° C. on EMPA117 EH Blood/milk/ink on cotton/polyester stains.

| protease concentration | 30 nM | 60 nM |
|---|---|---|
| Subtilisin309 (SEQ ID NO 1) | 1 | 1 |
| S9E + N43R + N76D + S188E + A194P + V205I + Q206L + Y209W + S216V + L262E + *275aH + *275bH | 1 | 1 |
| S9E + N43R + N76D + A158E + A194P + N204D + V205I + Q206L + Y209W + S212G + S216V + L262E | 1.2 | 1.1 |

TABLE 12-continued

Relative performance of proteases from *Bacillus* sp. subtilisin 309 variants compared to detergent with Subtilisin 309 (SEQ ID NO 1) at 20° C. on EMPA117 EH Blood/milk/ink on cotton/polyester stains.

| protease concentration | 30 nM | 60 nM |
|---|---|---|
| S9E + N43R + N76D + A158E + A194P + N204D + V205I + Q206L + Y209W + S212G + S216V + L262E + *275aH + *275bH | 1.3 | 1.2 |
| S9E + N43R + N76D + A158E + G160P + V205I + Q206L + Y209W + S259D + N261W + L262E | 1.3 | 1.3 |
| S9E + N43R + N76D + A158E + G160P + A194P + N204D + V205I + Q206L + Y209W + S212G + S216V + L262E | 1.3 | 1.3 |
| S9E + N43R + N76D + A158E + G160P + S151E + A194P + N204D + V205I + Q206L + Y209W + S216V + L262E + *275aH + *275bH | 1.2 | 1.1 |
| S9E + N43R + N76D + A158E + G160P + S151E + A194P + N204D + V205I + Q206L + Y209W + L262E | 1.1 | 1.1 |
| S9E + N43R + N76D + A158E + G160P + S151E + A194P + N204D + V205I + Q206L + Y209W + S212G + L262E + *275aH + *275bH | 1 | 1 |
| S9E + N43R + N76D + A158E + G160P + S151E + A194P + N204D + V205I + Q206L + Y209W + S212G + L262E | 1.1 | 1.1 |
| S9E + N43R + N76D + A158E + A194P + V205I + Q206L + Y209W + S259D + N261W + L262E | 1.2 | 1.2 |
| S9E + N43R + N76D + A158E + G160P + S151E + A194P + N204D + V205I + Q206L + Y209W + S212G + L262E + *275aH + *275bH | 1.2 | 1.1 |
| S9E + N43R + N76D + A158E + G160P + S151E + A194P + N204D + V205I + Q206L + Y209W + S216V + L262E | 1.1 | 1.1 |
| S9E + N43R + N76D + A158E + G160P + S151E + A194P + V205I + Q206L + Y209W + S212G + S216V + L262E | 1.2 | 1.2 |
| S9E + N43R + N76D + A158E + G160P + S161E + A194P + V205I + Q206L + Y209W + S212G + S216V + L262E + *275aH + *275bH | 1.3 | 1.2 |
| S9E + N43R + N76D + A158E + G160P + S161E + A194P + N204D + V205I + Q206L + Y209W + S216V + L262E | 1 | 1.1 |
| S9E + N43R + N76D + A158E + G160P + S161E + V205I + Q206L + Y209W + S259D + N261W + L262E | 1 | 1.1 |
| S9E + N43R + N76D + A158E + S161E + A194P + N204D + V205I + Q206L + Y209W + S212G + S216V + L262E | 1.1 | 1.1 |
| S9E + N43R + N76D + A158E + S161E + A194P + N204D + V205I + Q206L + Y209W + S212G + S216V + L262E + *275aH + *275bH | 1.2 | 1.2 |
| S9E + N43R + N76D + G160P + V205I + Q206L + Y209W + S259D + N261W + L262E | 1.3 | 1.3 |
| S9E + N43R + N76D + A194P + Q206L + Y209W + S216V + L262E | 0.9 | 0.9 |
| S9E + N43R + N76D + A194P + V205I + Q206L + Y209W + S216V + L262E | 0.9 | 1 |
| S9E + N43R + N76D + V205I + Q206L + Y209W + S259D + N261W + L262E | 1.1 | 1 |
| S9E + N43R + N76D + G115W + A194P + Q206L + Y209W + L217M + S259D + L262E | 1 | 1 |
| S9E + N43R + N76D + G115W + A194P + Q206L + Y209W + S216T + S259D + L262E | 1 | 1 |
| S9E + N43R + N76D + G160P + A194P + N204D + V205I + Q206L + Y209W + S212G + S216V + L262E | 1.2 | 1.1 |
| S9E + N43R + N76D + G160P + A194P + N204D + V205I + Q206L + Y209W + S212G + S216V + L262E + *275aH + *275bH | 1.1 | 1.1 |
| S9E + N43R + N76D + G160P + S161E + A194P + N204D + V205I + Q206L + Y209W + S212G + S216V + L262E | 1.2 | 1.2 |
| S9E + N43R + N76D + G160P + S161E + A194P + N204D + V205I + Q206L + Y209W + S212G + S216V + L262E + *275aH + *275bH | 1.2 | 1.1 |
| S9E + N43R + N76D + N204D + V205I + Q206L + Y209W + S259D + N261W + L262E | 1.3 | 1.3 |
| S9E + N43R + N76D + G160P + S161E + V205I + Q206L + Y209W + S259D + N261W + L262E | 1.4 | 1.4 |
| S3V + N76D + H120V + Q182E + N185E + S188E + V205I + Q206L + Y209W + S216V + S256D + N261W + L262E | 0.9 | 1 |
| S9E + N43R + N76D + H120V + Q182E + A194P + V205I + Q206L + Y209W + S256D + N261W + L262E + *275aH + *275bH | 1 | 1 |
| S9E + N43R + N76D + N117H + A194P + Q206L + Y209W + N238H + S259D + T260A + L262E | 1.1 | 1 |
| S9E + N43R + N76D + N185E + S188E + A194P + Q206L + Y209W + S259D + L262E | 1.1 | 1.1 |
| S9E + N43R + N76D + V205I + Q206L + Y209W + S216V + S259D + N261W + L262E | 1.3 | 1.2 |
| S9E + N43R + N76D + S161E + V205I + Q206L + Y209W + S259D + N261W + L262E | 1.3 | 1.2 |
| S9E + N43R + N76D + Q182E + A194P + V205I + Q206L + Y209W + S259D + N261W + L262E | 1.2 | 1.1 |
| S9E + N43R + N76D + S161E + A194P + N204D + V205I + Q206L + Y209W + S212G + S216V + L262E | 1.3 | 1.2 |
| S9E + N43R + N76D + S161E + A194P + N204D + V205I + Q206L + Y209W + S212G + S216V + L262E + *275aH + *275bH | 1.3 | 1.2 |
| S9E + N43R + N76D + V205I + Q206L + Y209W + S212G + S259D + N261W + L262E | 1.3 | 1.2 |

TABLE 12-continued

Relative performance of proteases from *Bacillus* sp. subtilisin 309 variants compared to detergent with Subtilisin 309 (SEQ ID NO 1) at 20° C. on EMPA117 EH Blood/milk/ink on cotton/polyester stains.

| protease concentration | 30 nM | 60 nM |
|---|---|---|
| S9E + N43R + N76D + S188E + A194P + V205I + Q206L + Y209W + S216V + L262E | 1.1 | 1.1 |
| S9E + N76D + Q182E + V205I + Q206L + Y209W + S256D + N261W + L262E | 1 | 1 |
| S9E + N43R + N76D + S78H + A194P + V205I + Q206L + Y209W + S216V + L262E | 0.8 | 0.9 |
| S9E + N43R + N76D + N204D + V205I + Q206L + Y209W + S212G + S216V + S259D + N261W + L262E | 1.4 | 1.3 |
| S9E + N76D + V205I + Q206L + Y209W + N261W + L262E | 0.9 | 1 |

The results of Table 12 show that the Subtilisin 309 variants have improved or on par performance wash performance compared to Subtilisin 309 on EMPA117 EH Blood/milk/ink on cotton/polyester extra heated at 20° C.

Example 7

Test of Subtilisin 309 Variants in Mini Wash

The wash performance of the proteases from *Bacillus* sp. was tested using laundry liquid detergent on one technical stain using the mini wash system.

The Mini wash assay is a test method where soiled textile is continuously lifted up and down into the test solution and subsequently rinsed.

TABLE 13

The wash experiment is conducted under the experimental conditions specified below:

| | |
|---|---|
| Detergent | Tixan-YPE commercial available detergent |
| Detergent dose | 2 g/l |
| pH | As is (i.e. not adjusted) |
| Water hardness | 8.4° dH. |
| Enzyme conc. | Example 20-40-80 nM |
| Test solution volume | 50 ml |
| Test material | EMPA117 EH Blood/milk/ink on cotton/polyester extra heated |
| Temperature | 25° C. |
| Wash time | 20 min soak + 18 min main wash |
| Rinse time | 10 min |
| Test system | Soiled textile continuously lifted up and down into the test solutions, 50 times per minute (up-time 0.29 sec, down-time 0.29 sec, lift time 0.17 sec). The test solutions are kept in 125 ml glass beakers. After wash of the textiles are continuously lifted up and down into tap water, 50 times per minute (up-time 0.5 sec, down-time 5 sec, lift time 0.5 sec). |

Test materials were obtained from EMPA Testmaterials AG Movenstrasse 12, CH-9015 St. Gallen, Switzerland.

The textiles were subsequently air-dried and the wash performance was measured as the brightness of the color of these textiles. Brightness can also be expressed as the Remission (R), which is a measure for the light reflected or emitted from the test material when illuminated with white light. The Remission (R) of the textiles was measured at 460 nm using a Zeiss MCS 521 VIS spectrophotometer. The measurements were done according to the manufacturer's protocol.

Calculating the enzyme effect was done by taking the measurements from washed swatches with enzymes and subtract with the measurements from washed without enzyme for each stain, $\Delta \text{Rem}_{enzyme}$.

The experiments were conducted as described in the mini wash assay for laundry method with the detergent composition and swatches described in table 13 and the experimental conditions as specified in Table 14 below.

TABLE 14

Experimental conditions for mini wash laundry experiments

| | |
|---|---|
| Detergent dosage | YPE, 2 g/L |
| Test solution volume | 50 mL |
| pH | As is |
| Wash time | 20 min soak + 18 min main wash |
| Temperature | 25° C. |
| Water hardness | 8.4° dH |
| Protease concentration | 20-40-80 nM |
| Swatch | EMPA117 EH (Blood/milk/ink on cotton/polyester extra heated) |

Water hardness was adjusted to 8.4° dH by addition of $CaCl_2$, $MgCl_2$, and $NaHCO_3$ ($Ca^{2+}$:$Mg^{2+}$:$CO_3^-$=2:1:4.5) to the test system. After washing the textiles were rinsed in tap water and dried.

TABLE 15

Relative performance of proteases from *Bacillus* sp. subtilisin 309 variants compared to detergent with Subtilisin 309 (SEQ ID NO 1) at 25° C.

| Protease concentration | 20 nM | 40 nM | 80 nM |
|---|---|---|---|
| Subtilisin309 (SEQ ID NO 1) | 1.0 | 1.0 | 1.0 |
| S9E + N43R + N76D + A158E + A194P + N204D + V205I + Q206L + Y209W + S212G + S216V + L262E | 1.1 | 1.3 | 1.1 |
| S9E + N43R + N76D + A158E + G160P + V205I + Q206L + Y209W + S259D + N261W + L262E | 1.1 | 1.5 | 1.5 |
| S9E + N43R + N76D + A158E + G160P + A194P + N204D + V205I + Q206L + Y209W + S212G + S216V + L262E | 1.1 | 1.2 | 1.3 |

TABLE 15-continued

Relative performance of proteases from *Bacillus* sp. subtilisin 309 variants compared to detergent with Subtilisin 309 (SEQ ID NO 1) at 25° C.

| Protease concentration | 20 nM | 40 nM | 80 nM |
|---|---|---|---|
| S9E + N43R + N76D + A158E + G160P + S151E + A194P + N204D + V205I + Q206L + Y209W + S216V + L262E + *275aH + *275bH | 0.9 | 1.1 | 1.1 |
| S9E + N43R + N76D + A158E + G160P + S151E + A194P + N204D + V205I + Q206L + Y209W + L262E | 0.8 | 1.0 | 1.1 |
| S9E + N43R + N76D + A158E + G160P + S151E + A194P + N204D + V205I + Q206L + Y209W + S212G + S216V + L262E + *275aH + *275bH | 0.8 | 0.9 | 1.3 |
| S9E + N43R + N76D + A158E + G160P + S151E + A194P + N204D + V205I + Q206L + Y209W + S212G + L262E | 1.0 | 1.2 | 1.4 |
| S9E + N43R + N76D + A158E + A194P + V205I + Q206L + Y209W + S259D + N261W + L262E | 0.9 | 1.3 | 1.5 |
| S9E + N43R + N76D + A158E + G160P + S151E + A194P + N204D + V205I + Q206L + Y209W + S212G + L262E + *275aH + *275bH | 0.7 | 0.9 | 1.0 |
| S9E + N43R + N76D + A158E + G160P + S151E + A194P + N204D + V205I + Q206L + Y209W + S216V + L262E | 1.1 | 1.2 | 1.3 |
| S9E + N43R + N76D + A158E + G160P + S161E + A194P + Q206L + Y209W + S259D + L262E + *275aH + *275bH | 0.9 | 0.8 | 1.1 |
| S9E + N43R + N76D + A158E + G160P + S161E + A194P + V205I + Q206L + Y209W + S212G + S216V + L262E | 1.2 | 1.2 | 1.3 |
| S9E + N43R + N76D + A158E + S161E + V205I + Q206L + Y209W + S259D + N261W + L262E | 0.8 | 1.2 | 1.4 |
| S9E + N43R + N76D + A158E + G160P + S161E + V205I + Q206L + Y209W + S259D + N261W + L262E | 0.7 | 1.1 | 1.1 |
| S9E + N43R + N76D + A158E + S161E + A194P + N204D + V205I + Q206L + Y209W + S212G + S216V + L262E | 1.0 | 1.2 | 1.1 |
| S9E + N43R + N76D + G160P + V205I + Q206L + Y209W + S259D + N261W + L262E | 1.1 | 1.3 | 1.3 |
| S9E + N43R + N76D + A194P + N204D + V205I + Q206L + Y209W + S212G + S216V + S259D + N261W + L262E | 1.1 | 1.1 | 1.1 |
| S9E + N43R + N76D + A194P + Q206L + Y209W + L262E | 1.1 | 1.1 | 1.1 |
| S9E + N43R + N76D + A194P + Q206L + Y209W + S256D + S259D + N261W + L262E | 0.9 | 0.9 | 1.0 |
| S9E + N43R + N76D + A194P + Q206L + Y209W + T255E + S256D + S259D + T260E + N261W + L262E | 1.1 | 1.1 | 1.2 |
| S9E + N43R + N76D + V205I + Q206L + Y209W + S259D + N261W + L262E | 1.1 | 1.3 | 1.2 |
| S9E + N43R + N76D + G115W + H120V + A194P + Q206L + Y209W + S259D + L262E | 0.9 | 1.0 | 1.1 |
| S9E + N43R + N76D + G115W + H120V + P129D + A194P + Q206L + Y209W + S259D + L262E | 0.8 | 1.0 | 0.9 |
| S9E + N43R + N76D + G160P + A194P + N204D + V205I + Q206L + Y209W + S212G + S216V + L262E | 1.3 | 1.4 | 1.2 |
| S9E + N43R + N76D + G160P + S161E + A194P + N204D + V205I + Q206L + Y209W + S212G + S216V + L262E | 1.1 | 1.4 | 1.3 |
| S9E + N43R + N76D + G160P + S161E + A194P + N204D + V205I + Q206L + Y209W + S212G + S216V + L262E + *275aH + *275bH | 1.4 | 1.5 | 1.5 |
| S9E + N43R + N76D + N204D + V205I + Q206L + Y209W + S259D + N261W + L262E | 1.0 | 1.1 | 1.4 |
| S9E + N43R + N76D + G160P + S161E + V205I + Q206L + Y209W + S259D + N261W + L262E | 1.1 | 1.2 | 1.3 |
| S9E + N43R + N76D + H120V + Q182E + A194P + V205I + Q206L + Y209W + S256D + N261W + L262E + *275aH + *275bH | 1.0 | 1.1 | 1.1 |
| S9E + N43R + N76D + V205I + Q206L + Y209W + S216V + S259D + N261W + L262E | 0.8 | 1.0 | 1.2 |
| S9E + N43R + N76D + S161E + V205I + Q206L + Y209W + S259D + N261W + L262E | 0.9 | 1.0 | 1.5 |
| S9E + N43R + N76D + P131* + A194P + Q206L + Y209W + S259D + L262E | 1.5 | 1.4 | 1.4 |
| S9E + N43R + N76D + H120V + Q182E + A194P + V205I + Q206L + Y209W + S256D + N261W + L262E + *275aH + *275bH | 0.9 | 1.0 | 1.2 |
| S9E + N43R + N76D + S161E + A194P + N204D + V205I + Q206L + Y209W + S212G + S216V + L262E + *275aH + *275bH | 0.9 | 1.2 | 1.2 |
| S9E + N43R + N76D + V205I + Q206L + Y209W + S212G + S259D + N261W + L262E | 1.0 | 1.2 | 1.5 |
| S9E + N43R + N76D + N204D + V205I + Q206L + Y209W + S212G + S216V + S259D + N261W + L262E | 1.1 | 1.2 | 1.3 |

The results Table 15 show that the Subtilisin309 variants showed improved or on par wash performance compared to Subtilisin309 (SEQ ID NO 1) on Blood/milk/ink at 25° C.

Example 8

Accelerated Storage Stability Assay

Storage stability of protease variants in liquid detergent was evaluated using an accelerated assay with incubation at 58° C., pH 9 for up to 48 hours in the CNS (Chinese national standard) detergent.

| CNS pH 9 | | |
|---|---|---|
| LAS, (C10-C13) alkylbenzene-sulfonic acid | 8% |
| AES, AEOS, sodium lauryl ether sulfate | 4% |
| AEO9, Alcohol ethoxylate | 4% |
| TEA (Triethanolamine) | 0.5% |
| NaCitrate | 0.5% |
| Sodium hydroxide | 1% |
| EDTA | 0.001% |
| Deionized Water to 100% | |
| (amounts in percent weight (wt)) | |

Otherwise the experiment was carried out under the same conditions as in Example 4 and 5.

The results in Table 16 are expressed as T½ IF: Half-life improvement factors relative to Subtilisin 309 (SEQ ID NO 1) as described in Example 4.

1: T½IF>1000;
2: 500≤T½IF≤1000;
3: 50≤T½IF<500.

TABLE 16

Accelerated storage stability results in CNS relative to Subtilisin 309.

| Mutations | |
|---|---|
| S9E + N43R + N76D + V205I + Q206L + Y209W + S216V + S259D + N261W + L262E | 2 |
| S9E + N43R + N76D + N204D + V205I + Q206L + Y209W + S212G + S216V + S259D + N261W + L262E | 1 |
| S9E + N43R + N76D + V205I + Q206L + Y209W + S212G + S259D + N261W + L262E | 2 |
| S9E + N43R + N76D + S161E + V205I + Q206L + Y209W + S259D + N261W + L262E | 2 |
| S9E + N43R + N76D + N204D + V205I + Q206L + Y209W + S259D + N261W + L262E | 2 |
| S9E + N43R + N76D + G160P + S161E + V205I + Q206L + Y209W + S259D + N261W + L262E | 2 |
| S9E + N43R + N76D + G160P + V205I + Q206L + Y209W + S259D + N261W + L262E | 2 |
| S9E + N43R + N76D + A158E + S161E + V205I + Q206L + Y209W + S259D + N261W + L262E | 2 |
| S9E + N43R + N76D + A158E + G160P + S161E + V205I + Q206L + Y209W + S259D + N261W + L262E | 2 |
| S9E + N43R + N76D + A158E + G160P + V205I + Q206L + Y209W + S259D + N261W + L262E | 2 |
| S9E + N43R + N76D + A158E + A194P + V205I + Q206L + Y209W + S259D + N261W + L262E | 2 |
| S9E + N43R + N76D + A158E + G160P + S161E + A194P + N204D + V205I + Q206L + Y209W + S212G + L262E + *275aH + *275bH | 1 |
| S9E + N43R + N76D + A158E + G160P + S161E + A194P + N204D + V205I + Q206L + Y209W + L262E + *275aH + *275bH | 2 |
| S9E + N43R + N76D + A158E + G160P + S161E + A194P + N204D + V205I + Q206L + Y209W + S216V + L262E + *275aH + *275bH | 1 |
| S9E + N43R + N76D + A158E + G160P + A194P + N204D + V205I + Q206L + Y209W + S212G + S216V + L262E + *275aH + *275bH | 1 |
| S9E + N43R + N76D + A158E + G160P + S161E + A194P + V205I + Q206L + Y209W + S212G + S216V + L262E + *275aH + *275bH | 2 |
| S9E + N43R + N76D + A158E + A194P + N204D + V205I + Q206L + Y209W + S212G + S216V + L262E + *275aH + *275bH | 2 |
| S9E + N43R + N76D + A158E + S161E + A194P + N204D + V205I + Q206L + Y209W + S212G + S216V + L262E + *275aH + *275bH | 2 |
| S9E + N43R + N76D + G160P + A194P + N204D + V205I + Q206L + Y209W + S216V + L262E + *275aH + *275bH | 1 |
| S9E + N43R + N76D + S161E + A194P + N204D + V205I + Q206L + Y209W + S212G + S216V + L262E + *275aH + *275bH | 1 |
| S9E + N43R + N76D + G160P + S161E + A194P + N204D + V205I + Q206L + Y209W + S212G + S216V + L262E + *275aH + *275bH | 1 |
| S9E + N43R + N76D + A158E + G160P + S161E + A194P + N204D + V205I + Q206L + Y209W + S212G + S216V + L262E + *275aH + *275bH | 1 |
| S9E + N43R + N76D + A194P + N204D + V205I + Q206L + Y209W + S212G + S216V + L262E | 1 |
| S9E + N43R + N76D + A158E + G160P + S161E + A194P + N204D + V205I + Q206L + Y209W + S212G + L262E | 1 |
| S9E + N43R + N76D + A158E + G160P + S161E + A194P + N204D + V205I + Q206L + Y209W + L262E | 1 |
| S9E + N43R + N76D + A158E + G160P + S161E + A194P + N204D + V205I + Q206L + Y209W + S216V + L262E | 1 |
| S9E + N43R + N76D + A158E + G160P + A194P + N204D + V205I + Q206L + Y209W + S212G + S216V + L262E | 1 |
| S9E + N43R + N76D + A158E + G160P + S161E + A194P + V205I + Q206L + Y209W + S212G + S216V + L262E | 1 |
| S9E + N43R + N76D + A158E + A194P + N204D + V205I + Q206L + Y209W + S212G + S216V + L262E | 1 |

TABLE 16-continued

Accelerated storage stability results in CNS relative to Subtilisin 309.

| Mutations | |
|---|---|
| S9E + N43R + N76D + A158E + S161E + A194P + N204D + V205I + Q206L + Y209W + S212G + S216V + L262E | 1 |
| S9E + N43R + N76D + G160P + A194P + N204D + V205I + Q206L + Y209W + S212G + S216V + L262E | 1 |
| S9E + N43R + N76D + S161E + A194P + N204D + V205I + Q206L + Y209W + S212G + S216V + L262E | 1 |
| S9E + N43R + N76D + G160P + S161E + A194P + N204D + V205I + Q206L + Y209W + S212G + S216V + L262E | 1 |
| S9E + N43R + N76D + A158E + G160P + S161E + A194P + N204D + V205I + Q206L + Y209W + S212G + S216V + L262E + *275aH + *275bH | 1 |
| S9E + N43R + N76D + A194P + N204D + V205I + Q206L + Y209W + S212G + S216V + L262E | 1 |
| S9E + N43R + N76D + A158E + G160P + S161E + A194P + N204D + V205I + Q206L + Y209W + S212G + S216V + L262E + *275aH + *275bH | 1 |
| S9E + N43R + N76D + Q182E + A194P + V205I + Q206L + Y209W + S259D + N261W + L262E | 2 |
| S9E + N43R + N76D + G115W + A194P + Q206L + Y209W + L217M + S259D + L262E | 3 |
| S9E + N43R + N76D + G115W + A194P + Q206L + Y209W + S216T + S259D + L262E | 2 |
| S9E + N43R + N76D + S188E + A194P + V205I + Q206L + Y209W + S216V + L262E | 2 |
| S9E + N43R + N76D + S78H + A194P + V205I + Q206L + Y209W + S216V + L262E | 2 |
| S9E + N43R + N76D + N117H + A194P + Q206L + Y209W + N238H + S259D + T260A + L262E | 3 |
| S9E + N43R + N76D + N185E + S188E + A194P + Q206L + Y209W + S259D + L262E | 3 |
| S9E + N43R + N76D + A194P + V205I + Q206L + Y209W + S216V + L262E | 3 |
| S9E + N43R + N76D + A194P + Q206L + Y209W + S216V + L262E | 3 |
| S9E + N43R + N76D + H120V + Q182E + A194P + V205I + Q206L + Y209W + S256D + N261W + L262E + *275aH + *275bH | 3 |
| S3V + N76D + H120V + Q182E + N185E + S188E + V205I + Q206L + Y209W + S216V + S256D + N261W + L262E | 1 |
| S3V + S9R + N76D + H120V + Q182E + N185E + S188E + V205I + Q206L + Y209W + S216V + S256D + N261W + L262E | 2 |
| S9E + N43R + N76D + S188E + A194P + V205I + Q206L + Y209W + S216V + L262E + *275aH + *275bH | 2 |
| S9E + N43R + N76D + V205I + Q206L + Y209W + S259D + N261W + L262E | 3 |
| S9E + N76D + V205I + Q206L + Y209W + N261W + L262E | 3 |
| S9E + N76D + Q182E + V205I + Q206L + Y209W + S256D + N261W + L262E | 2 |
| *35aD + N76D + H120D + G195E + K235L | 3 |
| S9E + N43R + N76D + A158E + G160P + S161E + A194P + N204D + V205I + Q206L + Y209W + S212G + S216V + L262E + *275aH + *275bH | 1 |
| S9E + N43R + N76D + A194P + N204D + V205I + Q206L + Y209W + S212G + S216V + L262E | 1 |
| S9E + N43R + N76D + A158E + G160P + S161E + A194P + N204D + V205I + Q206L + Y209W + S212G + S216V + L262E | 1 |
| S9E + N43R + A48H + N76D + N117H + A158E + G160P + S161E + A194P + N204D + V205I + Q206L + Y209W + S212G + S216V + N238H + L262E | 2 |
| S9E + N43R + A48H + N76D + N117H + G160D + S161E + A194P + N204D + V205I + Q206L + Y209W + S212G + S216V + N238H + L262E | 2 |

The invention claimed is:

1. A subtilase variant comprising the substitutions X9E+X206L+X262E, wherein
   (a) the positions correspond to the positions of the polypeptide of SEQ ID NO: 2;
   (b) the variant has protease activity; and
   (c) the variant has at least 90%, but less than 100%, sequence identity to the polypeptide of SEQ ID NO: 1, 2, 3, 4, 5, 6, 7, 8, 9, 10 or 11.

2. The variant of claim 1, which has at least 95% sequence identity to the polypeptide of SEQ ID NO: 1.

3. The variant of claim 1, which has at least 95%, at least 96%, at least 97%, or at least 98%, but less than 100%, sequence identity to the polypeptide of SEQ ID NO: 2.

4. The variant of claim 1, which has at least 95%, at least 96%, at least 97%, or at least 98%, but less than 100%, sequence identity to the polypeptide of SEQ ID NO: 3.

5. The variant of claim 1, which has at least 95%, at least 96%, at least 97%, or at least 98%, but less than 100%, sequence identity to the polypeptide of SEQ ID NO: 4.

6. The variant of claim 1, which has at least 95%, at least 96%, at least 97%, or at least 98%, but less than 100%, sequence identity to the polypeptide of SEQ ID NO: 5.

7. The variant of claim 1, which has at least 95%, at least 96%, at least 97%, or at least 98%, but less than 100%, sequence identity to the polypeptide of SEQ ID NO: 6.

8. The variant of claim 1, which has at least 95%, at least 96%, at least 97%, or at least 98%, but less than 100%, sequence identity to the polypeptide of SEQ ID NO: 7.

9. The variant of claim 1, which has at least 95%, at least 96%, at least 97%, or at least 98%, but less than 100%, sequence identity to the polypeptide of SEQ ID NO: 8.

10. The variant of claim 1, which has at least 95%, at least 96%, at least 97%, or at least 98%, but less than 100%, sequence identity to the polypeptide of SEQ ID NO: 9.

11. The variant of claim 1, which has at least 95%, at least 96%, at least 97%, or at least 98%, but less than 100%, sequence identity to the polypeptide of SEQ ID NO: 10.

12. The variant of claim 1, which has at least 95%, at least 96%, at least 97%, or at least 98%, but less than 100%, sequence identity to the polypeptide of SEQ ID NO: 11.

13. The variant of claim 1, which further comprises X76D.

14. The variant of claim 1, which further comprises one or more alterations selected from the group consisting of X3T, X4I, X15T, X24G, X24R, X27R, *36D, X43A, X43C, X43L, X43R, X43W, X68A, X72A, X72V, X78D, X87R, X87S, *97E, X98S, X99A, X99D, X99A, X99D, X99E, X99G, *99D, X101D, X101E, X101G, X101I, X101K, X101L, X101M, X101N, X101R, X103A, X104F, X104I, X104N, X104Y, X106A, X114V, X115T, X115W, X118R, X118V, X120D, X120I, X120N, X120T, X120V, X123S, X128A, X128L, X128S, X129D, X129N, X129Q, X130A, X147W, X149C, X149N, X158E, X160D, X160P, X161C, X161E, X162L, X163A, X163D, X167A, X170S, X182C, X182E, X185C, X185E, X188C, X188D, X188E, X191N, X194P, X195E, X199M, X204D, X204V, X205I, X209W, X212A, X212D, X212G, X212N, X216I, X216T, X216V, X217C, X217D, X217E, X217M, X217Q, X217Y, X218D, X218E, X218T, X222C, X222R, X222S, X225A, X232V, X235L, X236H, X245K, X245R, X252K, X255C, X255E, X256A, X256C, X256D, X256V, X256Y, X259D, X260E, X260P, X261C, X261E, X261F, X261L, X261M, X261V, X261W, X261Y, and X274A, wherein each position corresponds to the position of the polypeptide of SEQ ID NO: 2.

15. The variant of claim 1, comprising or consisting of a set of alterations selected from the group consisting of:
   S9E+N43R+N76D+S188E+A194P+V205I+Q206L+Y209W+S216V+L262E+*275aH+*275bH;
   S9E+N43R+N76D+A158E+A194P+N204D+V205I+Q206L+Y209W+S212G+S216V+L262E;
   S9E+N43R+N76D+A158E+A194P+N204D+V205I+Q206L+Y209W+S212G+S216V+L262E+*275aH+*275bH; S9E+N43R+N76D+A158E+G160P+V205I+Q206L+Y209W+S259D+N261W+L262E;
   S9E+N43R+N76D+A158E+G160P+A194P+N204D+V205I+Q206L+Y209W+S212G+S216V+L262E;
   S9E+N43R+N76D+A158E+A194P+V205I+Q206L+Y209W+S259D+N261W+L262E;
   S9E+N43R+N76D+A158E+G160P+S161E+A194P+N204D+V205I+Q206L+Y209W+L262E+*275aH+*275bH;
   S9E+N43R+N76D+A158E+G160P+S161E+A194P+V205I+Q206L+Y209W+S212G+S216V+L262E;
   S9E+N43R+N76D+A158E+G160P+S161E+A194P+V205I+Q206L+Y209W+S212G+S216V+L262E+*275aH+*275bH;
   S9E+N43R+N76D+A158E+S161E+A194P+N204D+V205I+Q206L+Y209W+S212G+S216V+L262E+*275aH+*275bH;
   S9E+N43R+N76D+G160P+V205I+Q206L+Y209W+S259D+N261W+L262E;
   S9E+N43R+N76D+A194P+V205I+Q206L+Y209W+S216V+L262E;
   S9E+N43R+N76D+G160P+A194P+N204D+V205I+Q206L+Y209W+S212G+S216V+L262E;
   S9E+N43R+N76D+G160P+A194P+N204D+V205I+Q206L+Y209W+S212G+S216V+L262E+*275aH+*275bH;
   S9E+N43R+N76D+G160P+S161E+A194P+N204D+V205I+Q206L+Y209W+S212G+S216V+L262E;
   S9E+N43R+N76D+G160P+S161E+A194P+N204D+V205I+Q206L+Y209W+S212G+S216V+L262E+*275aH+*275bH;
   S9E+N43R+N76D+N204D+V205I+Q206L+Y209W+S259D+N261W+L262E;
   S9E+N43R+N76D+G160P+S161E+V205I+Q206L+Y209W+S259D+N261W+L262E;
   S9E+N43R+N76D+N 117H+A194P+Q206L+Y209W+N238H+S259D+T260A+L262 E;

S9E+N43R+N76D+N 185E+S188E+A194P+Q206L+Y209W+S259D+L262E;
S9E+N43R+N76D+V205I+Q206L+Y209W+S216V+S259D+N261W+L262E;
S9E+N43R+N76D+S161E+V205I+Q206L+Y209W+S259D+N261W+L262E;
S9E+N43R+N76D+S161E+A194P+N204D+V205I+Q206L+Y209W+S212G+S216V+L262E;
S9E+N43R+N76D+S161E+A194P+N204D+V205I+Q206L+Y209W+S212G+S216V+L262E+*275aH+*275bH;
S9E+N43R+N76D+V205I+Q206L+Y209W+S212G+S259D+N261W+L262E;
S9E+N43R+N76D+S78H+A194P+V205I+Q206L+Y209W+S216V+L262 E;
S9E+N43R+N76D+N204D+V205I+Q206L+Y209W+S212G+S216V+S259D+N261W+L262E;
S9E+N76D+V205I+Q206L+Y209W+N261W+L262E;
S9E+N43R+N76D+A158E+G160P+S161E+A194P+N204D+V205I+Q206L+Y209W+S216V+L262E+*275aH+*275bH;
S9E+N43R+N76D+A158E+G160P+S161E+A194P+N204D+V205I+Q206L+Y209W+L262E;
S9E+N43R+N76D+A158E+G160P+S161E+A194P+N204D+V205I+Q206L+Y209W+S212G+L262 E+*275aH+*275bH ;
S9E+N43R+N76D+A194P+Q206L+Y209W+S216V+L262 E;
S9E+N43R+N76D+A158E+G160P+S161E+A194P+N204D+V205I+Q206L+Y209W+S212G+L262E;
S9E+N43R+N76D+A158E+G160P+S161E+A194P+N204D+V205I+Q206L+Y209W+S216V+L262E;
S9E+N43R+N76D+A158E+G160P+S161E+V205I+Q206L+Y209W+S259D+N261W+L262E;
S9E+N43R+N76D+A158E+S161E+A194P+N204D+V205I+Q206L+Y209W+S212G+S216V+L262E;
S9E+N43R+N76D+G115W+A194P+Q206L+Y209W+L217M+S259D+L262E;
S9E+N43R+N76D+G115W+A194P+Q206L+Y209W+S216T+S259D+L262 E;
S9E+N43R+N76D+A158E+G160P+S161E+A194P+N204D+V205I+Q206L+Y209W+S212G+S216V+L262E +*275aH+*275bH;
S9E+N43R+N76D+A158E+G160P+S161E+A194P+Q206L+Y209W+S259D+L262 E+*275aH+*275bH;
S9E+N43R+N76D+A158E+S161E+V205I+Q206L+Y209W+S259D+N261W+L262E;
S9E+N43R+N76D+A194P+N204D+V205I+Q206L+Y209W+S212G+S216V+S259D+N261W+L262E;
S9E+N43R+N76D+A194P+Q206L+Y209W+T255E+S256D+S259D+T260E+N261W+L262E;
S3V+S9R+N76D+H120V+Q182E+N185E+S188E+V205I+Q206L+Y209W+S216V+S256D+N261W+L262E;
S9E+N43R+A48H+N76D+N117H+A158E+G160P+S161E+A194P+N204D+V205I+Q206L+Y209W+S212G +S216V+N238H+L262 E;
S9E+N43R+A48H+N76D+N117H+G160D+S161E+A194P+N204D+V205I+Q206L+Y209W+S212G+S216V+N238H+L262E;
S9E+N43R+172A+N76D+Q141H+S145H+R149H+A158E+G159P+A194P+L262E;
W6L+S9E+N43R+A721+N76D+G115W+H120V+P129D+A158E+G160P+Q182E+N185E+S188E+Q191N+A194P+N204D+V205I+Q206L+Y209W+S212G+S216V+T255E+S256D+S259D+T260E+N261W+L262E;

S9E+G20H+T22H+S24H+N43R+N76D+G160D+S161E+A194P+N204D+V205I+Q206L+Y209W+S212G+S216V+L262E;
S9E+N43R+A48H+N76D+N117H+H120D+A158E+G160P+S161E+A194P+N204D+V205I+Q206L+Y209W+S212G+S216V+N238H+L262E+*275aR;
S9E+N43R+A48H+N76D+N117H+H120D+A158E+G160P+S161E+A194P+Q206L+Y209W+N238H+S259D+L262E+*275aR;
S9E+N43R+A48H+N76D+N117H+P129D+A194P+N204D+V205I+Q206L+Y209W+S212G+S216V+N238H+S256D+T260A+L262E;
S9E+N43R+A48H+N76D+N117H+A158E+G160P+S161E+A194P+N204D+V205I+Q206L+Y209W+S212G+S216V+N238H+L262 E;
S9E+N43R+A48H+N76D+N117H+A158E+G160P+S161E+A194P+Q206L+Y209W+N238H+S259D+L262E;
S9E+N43R+A48H+N76D+N117H+G160D+S161E+A194P+N204D+V205I+Q206L+Y209W+S212G+S216V+N238H+L262E;
S9E+N43R+A48H+N76D+N117H+G160D+S161E+A194P+Q206L+Y209W+N238H+S259D+L262 E;
S9E+N43R+A48H+N76D+N117H+A194P+G195E+N204D+V205I+Q206L+Y209W+S212G+S216V+N238H+L262E;
S9E+N43R+A48H+N76D+N117H+A194P+G195E+N204D+V205I+Q206L+Y209W+S212G+S216V+N238H+L262E+*275aR;
S9E+N43R+A48H+N76D+N 117H+A194P+N204D+V205I+Q206L+Y209W+S212G+S216V+N238H+S256D+T260A+L262E;
S9E+N43R+A48H+N76D+N 117H+A194P+Q206L+Y209W+N238H+S259D+T260A+L262E;
S9E+N43R+G61E+N76D+Q206L+L262E;
S9E+N43R+172A+N76D+G115W+H 120V+P129D+A158E+G160P+Q182E+N 185E+S188E+Q191N+A194P+N204D+V205I+Q206L+Y209W+S212G+S216V+T255E+S256D+S259D+T260E+N261W+L262E;
S9E+N43R+172A+N76D+G115W+H120V+P129D+Q182E+N185E+5188E+Q191N+A194P+N204D+V205I+Q206L+Y209W+S212G+S216V+T255E+S256D+S259D+T260E+N261W+L262E;
S9E+N43R+172A+N76D+Q182E+N185E+5188E+Q191N+A194P+N204D+V205I+Q206L+Y209W+S212G+S216V+T255E+5256D+5259D+T260E+N261W+L262E;
S9E+N43R+N76D+Y91H+N117H+A194P+G195E+N204D+V205I+Q206L+Y209W+S212G+S216V+N238H+L262E;
S9E+N43R+N76D+N117H+H120D+A158E+G160P+S161E+A194P+Q206L+Y209W+S259D+L262 E;
S9E+N43R+N76D+A194P+Q206L+Y209W+L262E;
S9E+N43R+N76D+A194P+Q206L+Y209W+S256D+S259D+N261W+L262E;
S9E+N43R+N76D+Q182E+N185E+S188E+Q191N+A194P+Q206L+Y209W+S259D+L262E;
S9E+N43R+N76D+A158E+G160P+S161E+A194P+N204D+V205I+Q206L+Y209W+S212G+S216V+L262E;
S9E+N43R+N76D+A158E+G160P+S161E+A194P+N204D+V205I+Q206L+Y209W+S212G+S216V+L262E+*275bH+*275aH;
S9E+N43R+N76D+N117H+H120D+G160D+S161E+A194P+N204D+V205I+Q206L+Y209W+S212G+S216V+L262 E+*275bH *275aH;

S9E+N43R+N76D+*99aE+P131*+A194P+Q206L+ Y209W+S259D+L262E;
S9E+N43R+N76D+G115W+H120V+P129D+A194P+ Q206L+Y209W+S259D+L262E;
S9E+N43R+N76D+G115W+H120V+A194P+Q206L+ Y209W+S259D+L262 E;
S9E+N43R+N76D+G115W+A194P+Q206L+Y209W+ S259D+L262 E;
S9E+N43R+N76D+N117H+H120D+A158E+G160P+ S161E+A194P+N204D+V205I+Q206L+Y209W+ S212G+S216V+L262E;
S9E+N43R+N76D+N117H+H120D+A158E+G160P+ S161E+A194P+N204D+V205I+Q206L+Y209W+ S212G+S216V+L262E+*275aH+*275bH;
S9E+N43R+N76D+N117H+H120D+A158E+G160P+ S161E+A194P+N204D+V205I+Q206L+Y209W+ S212G+S216V+L262E+*275aR;
S9E+N43R+N76D+N117H+H120D+A158E+G160P+ S161E+A194P+Q206L+Y209W+N238H+S259D+ L262E+*275aH+*275bH;
S9E+N43R+N76D+N117H+H120D+A158E+G160P+ S161E+A194P+Q206L+Y209W+S259D+L262 E;
S9E+N43R+N76D+N117H+H120D+G160D+S161E+ S163G+A194P+N204D+V205I+Q206L+Y209W+ S212G+S216V+L262E;
S9E+N43R+N76D+N117H+H120D+G160D+S161E+ S163G+A194P+N204D+V205I+Q206L+Y209W+ S212G+S216V+L262E+*275aH+*275bH;
S9E+N43R+N76D+N117H+H120D+G160D+S161E+ A194P+N204D+V205I+Q206L+Y209W+S212G+ S216V+L262 E;
S9E+N43R+N76D+N117H+H120D+G160D+S161E+ A194P+N204D+V205I+Q206L+Y209W+S212G+ S216V+L262 E+*275aH+*275bH ;
S9E+N43R+N76D+N117H+H120D+G160D+S161E+ A194P+Q206L+Y209W+S259D+L262E;
S9E+N43R+N76D+N117H+H120D+G160D+S161E+ A194P+Q206L+Y209W+S259D+L262 E+*275aH+ *275bH ;
S9E+N43R+N76D+N117H+H120D+A194P+N204D+ V205I+Q206L+Y209W+S212G+S216V+S256D+ T260A+L262 E;
S9E+N43R+N76D+N117H+H120D+A194P+N204D+ V205I+Q206L+Y209W+S212G+S216V+S256D+ L262E;
S9E+N43R+N76D+N117H+H120D+A194P+N204D+ V205I+Q206L+Y209W+S212G+S216V+T260A+ L262E;
S9E+N43R+N76D+N117H+H120D+A194P+N204D+ V205I+Q206L+Y209W+S212G+S216V+L262E;
S9E+N43R+N76D+N117H+H120D+A194P+N204D+ V205I+Q206L+Y209W+S212G+S216V+L262E+ *275aH+*275bH;
S9E+N43R+N76D+N117H+H120D+A194P+Q206L+ Y209W+S259D+T260A+L262 E+*275aR;
S9E+N43R+N76D+N117H+H120D+A194P+Q206L+ Y209W+S259D+L262E;
S9E+N43R+N76D+N117H+H120D+A194P+Q206L+ Y209W+S259D+L262E+*275aH+*275bH;
S9E+N43R+N76D+P129D+A194P+G195E+Q206L+ Y209W+S259D+L262E;
S9E+N43R+N76D+P129D+A194P+N204D+V205I+ Q206L+Y209W+S212G+S216V+S256D+T260A+ L262 E;
S9E+N43R+N76D+P129D+A194P+N204D+V205I+ Q206L+Y209W+S212G+S216V+S256D+T260A+ L262E+*275aH+*275bH;
S9E+N43R+N76D+P129D+A194P+Q206L+Y209W+ S259D+L262E;
S9E+N43R+N76D+P131*-FA194P+Q206L+Y209W+ S259D+L262E;
S9E+N43R+N76D+Q137H+S141H+R145H+A158E+ G160P+S161E+A194P+N204D+V205I+Q206L+ Y209W+S212G+S216V+L262E;
S9E+N43R+N76D+Q137H+S141H+R145H+G160D+ S161E+A194P+N204D+V205I+Q206L+Y209W+ S212G+S216V+L262E;
S9E+N43R+N76D+Q137H+S141H+R145H+A194P+ N204D+V205I+Q206L+Y209W+S212G+S216V+ L262E;
S9E+N43R+N76D+Q137H+S141H+R145H+A194P+ Q206L+Y209W+S259D+L262E;
S9E+N43R+N76D+A158E+G160P+S161E+A194P+ Q206L+Y209W+S259D+L262 E+*275aH+*275bH;
S9E+N43R+N76D+G160D+S161E+S163G+A194P+ N204D+V205I+Q206L+Y209W+S212G+S216V+ L262E;
S9E+N43R+N76D+G160D+S161E+A194P+N204D+ V205I+Q206L+Y209W+S212G+S216V+L262E;
S9E+N43R+N76D+G160D+S161E+A194P+N204D+ V205I+Q206L+Y209W+S212G+S216V+L262E+ *275aH+*275bH;
S9E+N43R+N76D+G160D+S161E+A194P+Q206L+ Y209W+S259D+L262E;
S9E+N43R+N76D+G160D+S161E+A194P+Q206L+ Y209W+S259D+L262E+*275aH+*275bH;
S9E+N43R+N76D+Q191N+A194P+Q206L+Y209W+ S259D+L262E;
S9E+N43R+N76D+A194P+G195E+N204D+V205I+ Q206L+Y209W+S212G+S216V+S256D+T260A+ L262 E;
S9E+N43R+N76D+A194P+G195E+N204D+V205I+ Q206L+Y209W+S212G+S216V+S256D+L262E;
S9E+N43R+N76D+A194P+G195E+N204D+V205I+ Q206L+Y209W+S212G+S216V+T260A+L262E;
S9E+N43R+N76D+A194P+G195E+N204D+V205I+ Q206L+Y209W+S212G+S216V+L262E;
S9E+N43R+N76D+A194P+G 195E+N204D+V205I+ Q206L+Y209W+S212G+S216V+L262 E+*275aH+ *275bH ;
S9E+N43R+N76D+A194P+G 195E+Q206L+Y209W+ S259D+L262E+*275aR;
S9E+N43R+N76D+A194P+N204D+V205I+Q206L+ Y209W+S212G+S216V+T255E+S256D+S259D+ N261W+L262E;
S9E+N43R+N76D+A194P+N204D+V205I+Q206L+ Y209W+S212G+S216V+S256D+S259D+T260E+ N261W+L262E;
S9E+N43R+N76D+A194P+N204D+V205I+Q206L+ Y209W+S212G+S216V+S256D+S259D+N261W+ L262 E;
S9E+N43R+N76D+A194P+N204D+V205I+Q206L+ Y209W+S212G+S216V+S256D+T260A+L262E+ *275aH+*275bH;
S9E+N43R+N76D+A194P+N204D+V205I+Q206L+ Y209W+S212G+S216V+S256D+T260A+L262 E+*275aR;
S9E+N43R+N76D+A194P+N204D+V205I+Q206L+ Y209W+S212G+S216V+S256D+L262E;
S9E+N43R+N76D+A194P+N204D+V205I+Q206L+ Y209W+S212G+S216V+S259D+N261W+L262 E;
S9E+N43R+N76D+A194P+N204D+V205I+Q206L+ Y209W+S212G+S216V+T260A+L262E;

S9E+N43R+N76D+A194P+N204D+V205I+Q206L+ Y209W+S212G+S216V+N261W+L262E;
S9E+N43R+N76D+H120V+Q182 E+A194P+V205I+ Q206L+Y209W+S256D+S259D+N261W+L262 E;
S9E+N43R+N76D+V205I+Q206L+Y209W+S259D+ N261W+L262E;
S9E+N43R+N76D+A194P+V205I+Q206L+Y209W+ S259D+N261W+L262E;
S9E+N43R+N76D+Q182E+A194P+V205I+Q206L+ Y209W+S256D+S259D+N261W+L262E;
S9E+N43R+N76D+H 120V+Q182 E+A194P+V205I+ Q206L+Y209W+S256D+N261W+L262 E+*275aH+ *275bH;
S3V+N76D+H120V+Q182E+N185E+S188E+V205I+ Q206L+Y209W+S216V+S256D+N261W+L262E;
S9E+N43R+G61E+N76D+G115W+H120V+A194P+ Q206L+S259D+L262E;
S9E+N43R+N76D+Q182E+A194P+V205I+Q206L+ Y209W+S259D+N261W+L262E;
S9E+N43R+N76D+A194P+V205I+Q206L+Y209W+ S216V+M222S+L262E;
S9E+N43R+N76D+A194P+V205I+Q206L+S256D+ S259D+N261W+L262 E;
S9E+N18S+N43R+N76D+G115W+H120V+A194P+ V205I+Q206L+S259D+L262E;
S9E+N43R+N76D+G115W+H 120V+A194P+V205I+ Q206L+S259D+L262E;
S9E+N43R+N76D+Q182E+A194P+V205I+Q206L+ Y209W+S256D+S259D+N261W+L262E;
S9E+N43R+N76D+S188E+A194P+V205I+Q206L+ Y209W+S216V+L262 E;
S9E+N76D+G115W+G160P+Q182E+V205I+Q206L+ Y209W+S256D+T260E+N261W+L262E S9E+ N43R+N76D+H120T+A194P+Q206L+S256D+ S259D+N261W+L262E;
S9E+N43R+N76D+H 120T+A194P+V205I+Q206L+ Y209W+S216V+L262 E;
S9E+N76D+G160P+Q182 E+V205I+Q206L+Y209W+ S256D+N261W+L262 E;
S9E+N43R+N76D+Q182E+A194P+V205I+Q206L+ S259D+N261W+L262E;
S9 E+N76D+Q182 E+V205I+Q206L+Y209W+S256D+ N261W+L262 E;
S9E+N43R+N76D+Q182E+A194P+V205I+Q206L+ S259D+N261W+L262E+*275aH ;
S9E+N43R+N76D+Q182E+N 185E+S188E+A194P+ Q206L+Y209W+S259D+L262 E;
S9E+N43R+N76D+N 185E+A194P+V205I+Q206L+ Y209W+S216V+L262E;
S9E+N43R+N76D+A194P+V205I+Q206L+Y209W+ S216V+N261M+L262E;
S9 E+N43R+I72A+N76D+A194P+Q206L+S259D+ L262 E;
S9E+N43R+N76D+A194P+V205I+Q206L+S259D+ L262 E;
S9E+N43R+N76D+H 120V+Q182 E+A194P+V205I+ Q206L+Y209W+S256D+S259D+N261W+L262E;
S9E+N43R+N76D+H 120V+Q182 E+A194P+V205I+ Q206L+Y209W+S256D+N261W+L262 E+*275bH;
S3V+N76D+H120V+Q182E+N185E+S188E+V205I+ Q206L+Y209W+S216V+S256D+N261W+L262E;
S9E+N43R+N76D+N117H+H120D+A158E+G160P+ S161E+A194P+Q206L+Y209W+S259D+L 262E;
S9E+N43R+N76D+A194P+N204D+V205I+Q206L+ Y209W+S212G+S216V+L262E;
S9E+N43R+N76D+A194P+V205I+Q206L+Y209W+ S212G+S216V+L262E;
S9E+N43R+N76D+A194P+Q206L+Y209W+S212G+ S216V+L262 E;
S9E+N43R+N76D+A194P+Q206L+Y209W+S212G+ S259D+L262E;
S9E+N43R+N76D+A194P+Q206L+Y209W+S212G+ L262E;
S9E+N43R+N76D+A194P+Q206L+Y209W+T255E+ S256D+S259D+T260E+N261W+L262E;
S9E+N43R+N76D+A194P N204D+V205I+Q206L+ Y209W+S212G+S216V+L262E;
S9E+N43R+N76D+N185E+S188E+Q191N+A194P+ Q206L+Y209W+S259D+L262E;
S9E+N43R+N76D+Q182E+N185E+S188E+Q191N+ A194P+Q206L+Y209W+S259D+L262E S9E N43R N76D N 185E S188E Q191N A194P Q206L Y209W S259D L262E S9E+N43R+N76D+G115W+H 120V+ P129D+A194P+Q206L+Y209W+S259D+L262E;
S9E+N43R+N76D+A158E+G160P+S161E+A194P+ N204D+V205I+Q206L+Y209W+S212G+S216V+ L262E;
S9E+N43R+N76D+A158E+G160P+S161E+A194P+ N204D+V205I+Q206L+Y209W+S212G+S216V+ L262E+*275bH+*275 aH S9E+N43R+N76D+ N117H+H120D+G160D+S161E+A194P+N204D+ V205I+Q206L+Y209W+S212G+S216V S9E+N43R+ N76D+A194P+Q206L+Y209W+S259D+T260A+ L262E;
S9E+N43R+N76D+A194P+Q206L+Y209W+S259D+ N261W+L262E;
S9E+N43R+N76D+A194P+Q206L+Y209W+S259D+ L262E;
S9E+N43R+N76D+A194P+Q206L+Y209W+S259D+ L262E+*275aH+*275bH;
S9E+N43R+N76D+A194P+Q206L+S259D+L262E;
S9E+N43R+N76D+A194P+Q206L+L262E;
S9E+G61E+N76D+N117H+H120D+G160D+S161E+ S163G+Q206L+L262E+*275aH+*275bH;
S9E+G61E+N76D+P129D+Q206L+S256D+T260A+ L262E+*275aH+*275bH;
S9E+G61E+N76D+P129D+Q206L+T260A+L262E;
S9E+G61E+N76D+P129D+Q206L+L262 E+*275aH+ *275bH;
S9E+G61E+N76D+Q137H+S141H+R145H+A158E+ G160P+S161E+Q206L+L262E;
S9E+G61E+N76D+Q137H+S141H+R145H+N204D+ Q206L+Y209W+L262E+*275aR;
S9E+G61E+N76D+Q137H+S141H+R145H+Q206L+ L262E;
S9E+G61E+N76D+A158E+G160P+S161E+Q206L+ L262E;
S9E+G61E+N76D+A158E+G160P+S161E+Q206L+ L262E+*275aH+*275bH;
S9E+G61E+N76D+N204D+Q206L+Y209W+L262E;
S9E+G61E+N76D+N204D+Q206L+Y209W+L262E+ *275aH+*275bH;
S9E+G61E+N76D+Q206L+Y209W+S256D+L262E;
S9E+G61E+N76D+Q206L+S256D+L262E;
S9E+G61E+N76D+Q206L+L262E;
S9E+G61E+N76D+Q206L+L262E+*275aH+*275bH;
S9E+N76D+Q206L+Y209W+N261W+L262E;
S9E+N76D+Q206L+Y209W+L262E; and
S9E+N76D+Q206L+L262E.

16. The variant of claim 15, which is a variant of 309 (SEQ ID NO: 1), comprising or consisting of the set of alterations.

17. The variant of claim 15, which is a variant of subtilisin BPN' (SEQ ID NO: 2), comprising or consisting of the set of alterations.

18. The variant of claim 1, which has at least 25% improved stability compared to a subtilase with SEQ ID NO: 1, when measured using an accelerated storage stability assay.

19. The variant of claim 1, which has an improved wash performance compared to SEQ ID NO: 1.

20. The variant of claim 1, wherein the total number of alterations compared to SEQ ID NO: 1 is between 3 and 20.

21. The variant of claim 1, wherein the variant consists of 260 to 280 amino acids.

22. A detergent composition comprising a variant of claim 1 and one or more detergent components.

23. The detergent composition of claim 22, which comprises one or more additional enzymes selected from the group consisting of amylases, catalases, cellulases, cutinases, haloperoxygenases, lipases, mannanases, pectinases, pectin lyases, peroxidases, proteases, xanthanases, xyloglucanases, and any mixture thereof.

24. The detergent composition of claim 22 in the form of a bar, a homogeneous tablet, a tablet having two or more layers, a pouch having one or more compartments, a regular or compact powder, a granule, a paste, a gel, or a regular, compact or concentrated liquid.

25. A method for producing a subtilase variant of claim 1, comprising
    (a) introducing into a parent subtilase the substitutions X9E+X206L+X262E; and
    (b) recovering the variant.

26. The variant of claim 1, which further comprises one or more alterations selected from the group consisting of S3T, V4I, A15T, S24G, S24R, K27R, *36D, N43A, N43C, N43L, N43R, N43W, V68A, I72A, I72V, S78D, N87R, N87S, *97E, A98S, S99A, S99D, S99A, S99D, S99E, S99G, *99D, S101D, S101E, S101G, S101I, S101K, S101L, S101M, S101N, S101R, S103A, V104F, V104I, V104N, V104Y, S106A, A114V, G115T, G115W, G118R, G118V, H120D, H120I, H120N, H120T, H120V, N123S, S128A, S128L, S128S, P129D, P129N, P129Q, S130A, V147W, V149C, V149N, A158E, G160D, G160P, S161C, S161E, I162L, S163A, S163D, Y167A, R170S, Q182C, Q182E, N185C, N185E, S188C, S188D, S188E), Q191N, A194P, G195E, V199M, N204D, N204V, V205I, Y209W, S212A, S212D, S212G, S212N, S216I, S216T, S216V, L217C, L217D, L217E, L217M, L217Q, L217Y, N218D, N218E, N218T, M222C, M222R, M222S, P225A, A232V, K235L, Q236H, Q245K, Q245R, N252K, T255C, T255E, S256A, S256C, S256D, S256V, S256Y, S259D, T260E, T260P, N261C, N261E, N261F, N261L, N261M, N261V, N261W, N261Y, and T274A, wherein each position corresponds to the position of the polypeptide of SEQ ID NO: 2.

* * * * *

SEQUENCE LISTING

<160> NUMBER OF SEQ ID NOS: 11

<210> SEQ ID NO 1
<211> LENGTH: 269
<212> TYPE: PRT
<213> ORGANISM: Bacillus lentus

<400> SEQUENCE: 1

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60
```

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 2
<211> LENGTH: 275
<212> TYPE: PRT
<213> ORGANISM: Bacillus amyloliquefaciens

<400> SEQUENCE: 2

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ala Gly Gly Ala
            35                  40                  45

Ser Met Val Pro Ser Glu Thr Asn Pro Phe Gln Asp Asn Asn Ser His
        50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
                180                 185                 190

Gly Pro Glu Leu Asp Val Met Ala Pro Gly Val Ser Ile Gln Ser Thr
            195                 200                 205

Leu Pro Gly Asn Lys Tyr Gly Ala Tyr Asn Gly Thr Ser Met Ala Ser
        210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 3
<211> LENGTH: 275
<212> TYPE: PRT
<213> ORGANISM: Bacillus subtilis 168

<400> SEQUENCE: 3

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Asn Val Arg Gly Gly Ala
            35                  40                  45

Ser Phe Val Pro Ser Glu Thr Asn Pro Tyr Gln Asp Gly Ser Ser His
        50                  55                  60

Gly Thr His Val Ala Gly Thr Ile Ala Ala Leu Asn Asn Ser Ile Gly
65                  70                  75                  80

Val Leu Gly Val Ser Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Thr Gly Ser Thr Ala Leu Lys Thr Val Val Asp Lys Ala Val Ser
    130                 135                 140

Ser Gly Ile Val Val Ala Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
            180                 185                 190

Gly Ser Glu Leu Asp Val Met Ala Pro Gly Val Ser Ile Gln Ser Thr
        195                 200                 205

Leu Pro Gly Gly Thr Tyr Gly Ala Tyr Asn Gly Thr Ser Met Ala Thr
    210                 215                 220

Pro His Val Ala Gly Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

Leu Gly Asn Ser Phe Tyr Tyr Gly Lys Gly Leu Ile Asn Val Gln Ala

```
                        260                 265                 270

Ala Ala Gln
        275

<210> SEQ ID NO 4
<211> LENGTH: 274
<212> TYPE: PRT
<213> ORGANISM: Bacillus subtilis DY

<400> SEQUENCE: 4

Ala Gln Thr Val Pro Tyr Gly Ile Pro Leu Ile Lys Ala Asp Lys Val
1               5                   10                  15

Gln Ala Gln Gly Tyr Lys Gly Ala Asn Val Lys Val Gly Ile Ile Asp
            20                  25                  30

Thr Gly Ile Ala Ala Ser His Thr Asp Leu Lys Val Val Gly Gly Ala
        35                  40                  45

Ser Phe Val Ser Gly Glu Ser Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Asn Val Ser Leu Tyr Ala Ile Lys Val Leu Asn
                85                  90                  95

Ser Ser Gly Ser Gly Thr Tyr Ser Ala Ile Val Ser Gly Ile Glu Trp
            100                 105                 110

Ala Thr Gln Asn Gly Leu Asp Val Ile Asn Met Ser Leu Gly Gly Pro
        115                 120                 125

Ser Gly Ser Thr Ala Leu Lys Gln Ala Val Asp Lys Ala Tyr Ala Ser
    130                 135                 140

Gly Ile Val Val Ala Ala Ala Gly Asn Ser Gly Ser Ser Gly Ser
145                 150                 155                 160

Gln Asn Thr Ile Gly Tyr Pro Ala Lys Tyr Asp Ser Val Ile Ala Val
            165                 170                 175

Gly Ala Val Asp Ser Asn Lys Asn Arg Ala Ser Phe Ser Ser Val Gly
        180                 185                 190

Ala Glu Leu Glu Val Met Ala Pro Gly Val Ser Val Tyr Ser Thr Tyr
    195                 200                 205

Pro Ser Asn Thr Tyr Thr Ser Leu Asn Gly Thr Ser Met Ala Ser Pro
210                 215                 220

His Val Ala Gly Ala Ala Ala Leu Ile Leu Ser Lys Tyr Pro Thr Leu
225                 230                 235                 240

Ser Ala Ser Gln Val Arg Asn Arg Leu Ser Ser Thr Ala Thr Asn Leu
            245                 250                 255

Gly Asp Ser Phe Tyr Tyr Gly Lys Gly Leu Ile Asn Val Glu Ala Ala
        260                 265                 270

Ala Gln

<210> SEQ ID NO 5
<211> LENGTH: 274
<212> TYPE: PRT
<213> ORGANISM: Bacillus licheniformis

<400> SEQUENCE: 5

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30
```

```
Thr Gly Ile Gln Ala Ser His Pro Asp Leu Asn Val Gly Gly Ala
            35                  40                  45

Ser Phe Val Ala Gly Glu Ala Tyr Asn Thr Asp Gly Asn Gly His Gly
 50                  55                  60

Thr His Val Ala Gly Thr Val Ala Ala Leu Asp Asn Thr Thr Gly Val
 65                  70                  75                  80

Leu Gly Val Ala Pro Ser Val Ser Leu Tyr Ala Val Lys Val Leu Asn
                 85                  90                  95

Ser Ser Gly Ser Gly Thr Tyr Ser Gly Ile Val Ser Gly Ile Glu Trp
             100                 105                 110

Ala Thr Thr Asn Gly Met Asp Val Ile Asn Met Ser Leu Gly Gly Pro
         115                 120                 125

Ser Gly Ser Thr Ala Met Lys Gln Ala Val Asp Asn Ala Tyr Ala Arg
     130                 135                 140

Gly Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                 165                 170                 175

Gly Ala Val Asp Ser Asn Ser Asn Arg Ala Ser Phe Ser Ser Val Gly
             180                 185                 190

Ala Glu Leu Glu Val Met Ala Pro Gly Ala Gly Val Tyr Ser Thr Tyr
         195                 200                 205

Pro Thr Ser Thr Tyr Ala Thr Leu Asn Gly Thr Ser Met Ala Ser Pro
     210                 215                 220

His Val Ala Gly Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                 245                 250                 255

Gly Ser Ser Phe Tyr Tyr Gly Lys Gly Leu Ile Asn Val Glu Ala Ala
             260                 265                 270

Ala Gln

<210> SEQ ID NO 6
<211> LENGTH: 268
<212> TYPE: PRT
<213> ORGANISM: Bacillus lentus

<400> SEQUENCE: 6

Gln Thr Val Pro Trp Gly Ile Ser Phe Ile Asn Thr Gln Gln Ala His
 1               5                  10                  15

Asn Arg Gly Ile Phe Gly Asn Gly Ala Arg Val Ala Val Leu Asp Thr
             20                  25                  30

Gly Ile Ala Ser His Pro Asp Leu Arg Ile Ala Gly Gly Ala Ser Phe
         35                  40                  45

Ile Ser Ser Glu Pro Ser Tyr His Asp Asn Asn Gly His Gly Thr His
     50                  55                  60

Val Ala Gly Thr Ile Ala Ala Leu Asn Asn Ser Ile Gly Val Leu Gly
 65                  70                  75                  80

Val Arg Pro Ser Ala Asp Leu Tyr Ala Leu Lys Val Leu Asp Arg Asn
                 85                  90                  95

Gly Ser Gly Ser Leu Ala Ser Val Ala Gln Gly Ile Glu Trp Ala Ile
             100                 105                 110

Asn Asn Asn Met His Ile Ile Asn Met Ser Leu Gly Ser Thr Ser Gly
         115                 120                 125
```

```
Ser Ser Thr Leu Glu Leu Ala Val Asn Arg Ala Asn Ala Gly Ile
    130                 135                 140

Leu Leu Val Gly Ala Ala Gly Asn Thr Gly Arg Gln Gly Val Asn Tyr
145                 150                 155                 160

Pro Ala Arg Tyr Ser Gly Val Met Ala Val Ala Val Asp Gln Asn
                165                 170                 175

Gly Gln Arg Ala Ser Phe Ser Thr Tyr Gly Pro Glu Ile Glu Ile Ser
                180                 185                 190

Ala Pro Gly Val Asn Val Asn Ser Thr Tyr Thr Gly Asn Arg Tyr Val
                195                 200                 205

Ser Leu Ser Gly Thr Ser Met Ala Thr Pro His Val Ala Gly Val Ala
    210                 215                 220

Ala Leu Val Lys Ser Arg Tyr Pro Ser Tyr Thr Asn Asn Gln Ile Arg
225                 230                 235                 240

Gln Arg Ile Asn Gln Thr Ala Thr Tyr Leu Gly Ser Pro Ser Leu Tyr
                245                 250                 255

Gly Asn Gly Leu Val His Ala Gly Arg Ala Thr Gln
                260                 265
```

<210> SEQ ID NO 7
<211> LENGTH: 269
<212> TYPE: PRT
<213> ORGANISM: Bacillus alcalophilus PB92

<400> SEQUENCE: 7

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Asn Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
                100                 105                 110

Gly Asn Asn Gly Met His Val Ala Asn Leu Ser Leu Gly Ser Pro Ser
                115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
                195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
```

```
                    225                 230                 235                 240
Arg Asn His Leu Lys Asn Thr Ala Thr Ser Leu Gly Ser Thr Asn Leu
                    245                 250                 255

Tyr Gly Ser Gly Leu Val Asn Ala Glu Ala Ala Thr Arg
                260                 265

<210> SEQ ID NO 8
<211> LENGTH: 268
<212> TYPE: PRT
<213> ORGANISM: Bacillus YaB

<400> SEQUENCE: 8

Gln Thr Val Pro Trp Gly Ile Asn Arg Val Gln Ala Pro Ile Ala Gln
 1               5                  10                  15

Ser Arg Gly Phe Thr Gly Thr Gly Val Arg Val Ala Val Leu Asp Thr
                20                  25                  30

Gly Ile Ser Asn His Ala Asp Leu Arg Ile Arg Gly Gly Ala Ser Phe
            35                  40                  45

Val Pro Gly Glu Pro Asn Ile Ser Asp Gly Asn Gly His Gly Thr Gln
        50                  55                  60

Val Ala Gly Thr Ile Ala Ala Leu Asn Asn Ser Ile Gly Val Leu Gly
 65                  70                  75                  80

Val Ala Pro Asn Val Asp Leu Tyr Gly Val Lys Val Leu Gly Ala Ser
                85                  90                  95

Gly Ser Gly Ser Ile Ser Gly Ile Ala Gln Gly Leu Gln Trp Ala Ala
                100                 105                 110

Asn Asn Gly Met His Ile Ala Asn Met Ser Leu Gly Ser Ser Ala Gly
            115                 120                 125

Ser Ala Thr Met Glu Gln Ala Val Asn Gln Ala Thr Ala Ser Gly Val
        130                 135                 140

Leu Val Val Ala Ala Ser Gly Asn Ser Gly Ala Gly Asn Val Gly Phe
145                 150                 155                 160

Pro Ala Arg Tyr Ala Asn Ala Met Ala Val Gly Ala Thr Asp Gln Asn
                165                 170                 175

Asn Asn Arg Ala Thr Phe Ser Gln Tyr Gly Ala Gly Leu Asp Ile Val
            180                 185                 190

Ala Pro Gly Val Gly Val Gln Ser Thr Val Pro Gly Asn Gly Tyr Ala
        195                 200                 205

Ser Phe Asn Gly Thr Ser Met Ala Thr Pro His Val Ala Gly Val Ala
    210                 215                 220

Ala Leu Val Lys Gln Lys Asn Pro Ser Trp Ser Asn Val Gln Ile Arg
225                 230                 235                 240

Asn His Leu Lys Asn Thr Ala Thr Asn Leu Gly Asn Thr Thr Gln Phe
                245                 250                 255

Gly Ser Gly Leu Val Asn Ala Glu Ala Ala Thr Arg
            260                 265

<210> SEQ ID NO 9
<211> LENGTH: 272
<212> TYPE: PRT
<213> ORGANISM: Bacillus sp. NKS-21

<400> SEQUENCE: 9

Gln Thr Val Pro Trp Gly Ile Pro Tyr Ile Tyr Ser Asp Val Val His
 1               5                  10                  15

Arg Gln Gly Tyr Phe Gly Asn Gly Val Lys Val Ala Val Leu Asp Thr
```

```
                    20                  25                  30
Gly Val Ala Pro His Pro Asp Leu His Ile Arg Gly Val Ser Phe
                35                  40                  45
Ile Ser Thr Glu Asn Thr Tyr Val Asp Tyr Asn Gly His Gly Thr His
         50                  55                  60
Val Ala Gly Thr Val Ala Leu Asn Asn Ser Tyr Gly Val Leu Gly
 65                  70                  75                  80
Val Ala Pro Gly Ala Glu Leu Tyr Ala Val Lys Val Leu Asp Arg Asn
                 85                  90                  95
Gly Ser Gly Ser His Ala Ser Ile Ala Gln Gly Ile Glu Trp Ala Met
                100                 105                 110
Asn Asn Gly Met Asp Ile Ala Asn Met Ser Leu Gly Ser Pro Ser Gly
                115                 120                 125
Ser Thr Thr Leu Gln Leu Ala Ala Asp Arg Ala Arg Asn Ala Gly Val
                130                 135                 140
Leu Leu Ile Gly Ala Ala Gly Asn Ser Gly Gln Gln Gly Gly Ser Asn
145                 150                 155                 160
Asn Met Gly Tyr Pro Ala Arg Tyr Ala Ser Val Met Ala Val Gly Ala
                165                 170                 175
Val Asp Gln Asn Gly Asn Arg Ala Asn Phe Ser Ser Tyr Gly Ser Glu
                180                 185                 190
Leu Glu Ile Met Ala Pro Gly Val Asn Ile Asn Ser Thr Tyr Leu Asn
                195                 200                 205
Asn Gly Tyr Arg Ser Leu Asn Gly Thr Ser Met Ala Ser Pro His Val
                210                 215                 220
Ala Gly Val Ala Ala Leu Val Lys Gln Lys His Pro His Leu Thr Ala
225                 230                 235                 240
Ala Gln Ile Arg Asn Arg Met Asn Gln Thr Ala Ile Pro Leu Gly Asn
                245                 250                 255
Ser Thr Tyr Tyr Gly Asn Gly Leu Val Asp Ala Glu Tyr Ala Ala Gln
                260                 265                 270

<210> SEQ ID NO 10
<211> LENGTH: 269
<212> TYPE: PRT
<213> ORGANISM: Bacillus sp. G-825-6

<400> SEQUENCE: 10

Asn Gln Val Thr Pro Trp Gly Ile Thr Arg Val Gln Ala Pro Thr Ala
 1                   5                  10                  15
Trp Thr Arg Gly Tyr Thr Gly Thr Gly Val Arg Val Ala Val Leu Asp
                 20                  25                  30
Thr Gly Ile Ser Thr His Pro Asp Leu Asn Ile Arg Gly Gly Val Ser
                 35                  40                  45
Phe Val Pro Gly Glu Pro Ser Tyr Gln Asp Gly Asn Gly His Gly Thr
             50                  55                  60
His Val Ala Gly Thr Ile Ala Ala Leu Asn Asn Ser Ile Gly Val Val
 65                  70                  75                  80
Gly Val Ala Pro Asn Ala Glu Leu Tyr Ala Val Lys Val Leu Gly Ala
                 85                  90                  95
Asn Gly Ser Gly Ser Val Ser Ser Ile Ala Gln Gly Leu Gln Trp Thr
                100                 105                 110
Ala Gln Asn Asn Ile His Val Ala Asn Leu Ser Leu Gly Ser Pro Val
                115                 120                 125
```

```
Gly Ser Gln Thr Leu Glu Leu Ala Val Asn Gln Ala Thr Asn Ala Gly
    130                 135                 140

Val Leu Val Val Ala Ala Thr Gly Asn Asn Gly Ser Gly Thr Val Ser
145                 150                 155                 160

Tyr Pro Ala Arg Tyr Ala Asn Ala Leu Ala Val Gly Ala Thr Asp Gln
                165                 170                 175

Asn Asn Asn Arg Ala Ser Phe Ser Gln Tyr Gly Thr Gly Leu Asn Ile
            180                 185                 190

Val Ala Pro Gly Val Gly Ile Gln Ser Thr Tyr Pro Gly Asn Arg Tyr
        195                 200                 205

Ala Ser Leu Ser Gly Thr Ser Met Ala Thr Pro His Val Ala Gly Val
    210                 215                 220

Ala Ala Leu Val Lys Gln Lys Asn Pro Ser Trp Ser Asn Thr Gln Ile
225                 230                 235                 240

Arg Gln His Leu Thr Ser Thr Ala Thr Ser Leu Gly Asn Ser Asn Gln
                245                 250                 255

Phe Gly Ser Gly Leu Val Asn Ala Glu Ala Ala Thr Arg
            260                 265

<210> SEQ ID NO 11
<211> LENGTH: 279
<212> TYPE: PRT
<213> ORGANISM: Thermoactinomyces vulgaris

<400> SEQUENCE: 11

Tyr Thr Pro Asn Asp Pro Tyr Phe Ser Ser Arg Gln Tyr Gly Pro Gln
1               5                   10                  15

Lys Ile Gln Ala Pro Gln Ala Trp Asp Ile Ala Glu Gly Ser Gly Ala
                20                  25                  30

Lys Ile Ala Ile Val Asp Thr Gly Val Gln Ser Asn His Pro Asp Leu
            35                  40                  45

Ala Gly Lys Val Val Gly Gly Trp Asp Phe Val Asp Asn Asp Ser Thr
        50                  55                  60

Pro Gln Asn Gly Asn Gly His Gly Thr His Cys Ala Gly Ile Ala Ala
65                  70                  75                  80

Ala Val Thr Asn Asn Ser Thr Gly Ile Ala Gly Thr Ala Pro Lys Ala
                85                  90                  95

Ser Ile Leu Ala Val Arg Val Leu Asp Asn Ser Gly Ser Gly Thr Trp
            100                 105                 110

Thr Ala Val Ala Asn Gly Ile Thr Tyr Ala Ala Asp Gln Gly Ala Lys
        115                 120                 125

Val Ile Ser Leu Ser Leu Gly Gly Thr Val Gly Asn Ser Gly Leu Gln
    130                 135                 140

Gln Ala Val Asn Tyr Ala Trp Asn Lys Gly Ser Val Val Val Ala Ala
145                 150                 155                 160

Ala Gly Asn Ala Gly Asn Thr Ala Pro Asn Tyr Pro Ala Tyr Tyr Ser
                165                 170                 175

Asn Ala Ile Ala Val Ala Ser Thr Asp Gln Asn Asp Asn Lys Ser Ser
            180                 185                 190

Phe Ser Thr Tyr Gly Ser Val Val Asp Val Ala Ala Pro Gly Ser Trp
        195                 200                 205

Ile Tyr Ser Thr Tyr Pro Thr Ser Thr Tyr Ala Ser Leu Ser Gly Thr
    210                 215                 220

Ser Met Ala Thr Pro His Val Ala Gly Val Ala Gly Leu Leu Ala Ser
225                 230                 235                 240
```

```
Gln Gly Arg Ser Ala Ser Asn Ile Arg Ala Ala Ile Glu Asn Thr Ala
                245                 250                 255

Asp Lys Ile Ser Gly Thr Gly Thr Tyr Trp Ala Lys Gly Arg Val Asn
                260                 265                 270

Ala Tyr Lys Ala Val Gln Tyr
                275
```